(12) United States Patent
Wei

(10) Patent No.: US 12,391,799 B2
(45) Date of Patent: *Aug. 19, 2025

(54) PEPTOID POLYMERS AND METHODS OF USE

(71) Applicant: X-Therma, Inc., Richmond, CA (US)

(72) Inventor: Xiaoxi Wei, El Cerrito, CA (US)

(73) Assignee: X-THERMA, INC., Richmond, CA (US)

(*) Notice: Subject to any disclaimer, the term of this patent is extended or adjusted under 35 U.S.C. 154(b) by 73 days.

This patent is subject to a terminal disclaimer.

(21) Appl. No.: 18/161,773

(22) Filed: Jan. 30, 2023

(65) Prior Publication Data
US 2024/0084074 A1    Mar. 14, 2024

Related U.S. Application Data

(63) Continuation of application No. 16/583,885, filed on Sep. 26, 2019, now Pat. No. 11,608,414, which is a continuation of application No. PCT/US2018/027160, filed on Apr. 11, 2018.

(60) Provisional application No. 62/484,714, filed on Apr. 12, 2017.

(51) Int. Cl.
| | |
|---|---|
| *C07K 7/08* | (2006.01) |
| *A23B 2/762* | (2025.01) |
| *A23B 2/85* | (2025.01) |
| *A23L 13/40* | (2023.01) |
| *A61K 8/64* | (2006.01) |
| *A61K 8/88* | (2006.01) |
| *C08G 69/10* | (2006.01) |
| *C09K 3/18* | (2006.01) |

(52) U.S. Cl.
CPC .............. *C08G 69/10* (2013.01); *A23B 2/762* (2025.01); *A23B 2/85* (2025.01); *A23L 13/422* (2016.08); *A61K 8/64* (2013.01); *A61K 8/88* (2013.01); *C07K 7/08* (2013.01); *C09K 3/18* (2013.01); *A61K 2800/54* (2013.01)

(58) Field of Classification Search
CPC ........... C08G 69/10; A23B 2/762; A23B 2/85; A23L 13/422; A61K 8/64; A61K 8/88; A61K 2800/54; A61K 8/65; A61K 38/00; C07K 7/08; C07K 14/001; C07K 7/02; C09K 3/18; A61Q 19/00
See application file for complete search history.

(56) References Cited

U.S. PATENT DOCUMENTS

| | | | |
|---|---|---|---|
| 7,834,144 B2 | 11/2010 | Peretz et al. | |
| 9,364,449 B2 | 6/2016 | Sadowski et al. | |
| 9,986,733 B2 | 6/2018 | Wei | |
| 10,694,739 B2 | 6/2020 | Wei | |
| 11,510,407 B2 | 11/2022 | Wei | |
| 11,564,388 B2 | 1/2023 | Wei | |
| 11,608,414 B2 * | 3/2023 | Wei | C07K 7/02 |
| 12,137,682 B2 | 11/2024 | Wei | |
| 12,207,647 B2 | 1/2025 | Wei | |
| 2006/0160735 A1 | 7/2006 | Shuey et al. | |
| 2008/0081789 A1 | 4/2008 | Shuey et al. | |
| 2012/0237552 A1 | 9/2012 | Moreno et al. | |

FOREIGN PATENT DOCUMENTS

| | | |
|---|---|---|
| CN | 116284240 A | 6/2023 |
| JP | 2009507833 A | 2/2009 |
| WO | 2007030804 A1 | 3/2007 |
| WO | 2010017412 A1 | 2/2010 |
| WO | 2014104981 A1 | 7/2014 |
| WO | 2017017445 A1 | 2/2017 |
| WO | 2017066454 A2 | 4/2017 |
| WO | 2018191371 A1 | 10/2018 |
| WO | 2018191411 A1 | 10/2018 |

OTHER PUBLICATIONS

Andreev et al., "Cyclization Improves Membrane Permeation by Antimicrobial Peptoids," Langmuir, vol. 32, No. 48, 2016, pp. 12905-12913.

Bolt et al., "Enlarging the Chemical Space of Anti-Leishmanials: a Structure-Activity Relationship Study of Peptoids Against Leishmania Mexicana, a Causative Agent of Cutaneous Leishmaniasis," Med. Chem. Commun, vol. 7, 2016, pp. 799-805.

Bolt et al., "Exploring the Links Between Peptoid Antibacterial Activity and Toxicity," Med. Chem. Commun, vol. 8, No. 5, 2017, pp. 886-896.

Chen et al., "Engineered Biomimetic Polymers as Tunable Agents for Controlling CaC03 Mineralization," Journal of the American Chemical Society, vol. 133, No. 14, 2011, pp. 5214-5217.

Chongsiriwatana et al., "Functional Synergy between Antimicrobial Peptoids and Peptides against Gram-Negative Bacteria," Antimicrobial Agents and Chemotherapy, vol. 55, No. 11, 2011, 16 pages.

Chongsiriwatana et al., "Short Alkylated Peptoid Mimics of Antimicrobial Lipopeptides," Antimicrobial Agents and Chemotherapy, vol. 55, No. 1, 2010, pp. 417-420.

(Continued)

*Primary Examiner* — Sudhakar Katakam
(74) *Attorney, Agent, or Firm* — Kilpatrick Townsend & Stockton LLP

(57) ABSTRACT

The present invention provides peptoid polymers and salts thereof that comprise hydrophobic and polar peptoid monomers and are capable of reducing or inhibiting the formation of ice crystals at sub 0° C. temperatures. Also provided are peptoid-peptide hybrids and salts thereof comprising the peptoid polymers provided herein. The peptoid polymers, peptoid-peptide hybrids, and salts thereof provided herein are useful for making cryoprotectant solutions. The peptoid polymers, peptoid-peptide hybrids, salts thereof, and cryoprotectant solutions provided herein are useful for making antifreeze solutions, frozen food products, and cosmetic care products. Also provided herein are methods for preserving a tissue, an organ, a cell, or a biological macromolecule using the compositions described herein.

13 Claims, 15 Drawing Sheets

(56) References Cited

OTHER PUBLICATIONS

Czyzewski et al., "In Vivo, In Vitro, and In Silica Characterization of Peptoids as Antimicrobial Agents," PLOS One, vol. 11, No. 2, 2016, pp. 1-17.

Application No. EP18785013.6, Extended European Search Report, Mailed On Dec. 8, 2020, 10 pages.

Ford, "The Design, Synthesis and Evaluation of Peptoid Heparin Inhibitors," UC Riverside Electronic Theses and Dissertations, retrieved online at https://escholarship.org/uc/item/5g32g729, 2011, pp. 1-238.

Ganesh et al., "Ethyl({[Acryloyl(Furan-2-Ylmethyl)Amino]Acetyl}Amino)Acetate," Molbank, vol. 1, Jan. 9, 2017, pp. 1-4.

Govindaraju et al., "Two-Dimensional Nanoarchitectonics: Organic and Hybrid Materials," Nanoscale, vol. 4, No. 20, 2012, pp. 6102-6117.

Hebert, "Peptoid Based Slide Coatings for Disease Detection via ELISA Microarray Analysis," Thesis and Dissertations 463 https://sch olarworks. uark. ed u/cg i/viewcontent. cg i? article=1462 &context=etd, 2012, 81 pages.

Hebert et al., "Tunable Peptoid Microspheres: Effects of Side Chain Chemistry and Sequence," Organic & Biomolecular Chemistry, vol. 11, No. 27, 2013, pp. 4459-4464.

Hebert et al., "Uniform and Robust Peptoid Microsphere Coatings," Coatings, vol. 3, No. 2, 2013, pp. 98-107.

Huang et al., "A Comparison of Linear and Cyclic Peptoid Oligomers as Potent Antimicrobial Agents," ChemMedChem, vol. 7, No. 1, 2012, pp. 114-122.

Huang et al., "Biomimetic Peptoid Oligomers as Dual-Action Antifreeze Agents," Proceedings of the National Academy of Sciences, vol. 109, No. 49, Dec. 4, 2012, p. 19922-19927.

Huang et al., "Peptoid Transporters: Effects of Cationic, Amphipathic Structure on Their Cellular Uptake," Molecular Biosystems, vol. 8, No. 10, 2012, pp. 2626-2628.

Jahnsen et al., "Antimicrobial Activity of Peptidomimetics Against Multidrug-Resistant *Escherichia coli*: A Comparative Study of Different Backbones," Journal of Medicinal Chemistry, vol. 55, No. 16, 2012, pp. 7253-7261.

Jin et al., "Highly Stable And Self-Repairing Membrane-Mimetic 2D Nanomaterials Assembled From Lipid-Like Peptoids," Nature Communications, vol. 7, Jul. 12, 2016, pp. 1-8.

Jun et al., "Peptoid Nanosheets as Soluble, Two-Dimensional Templates for Calcium Carbonate Mineralization," Chem. Comm., vol. 51, 2015, pp. 10218-10221.

Kang et al., "Precisely Tuneable Energy Transfer System Using Peptoid Helix-Based Molecular Scaffold," Scientific Reports, vol. 7, 2017, pp. 4786-4795.

Kapoor et al., "Efficacy of Antimicrobial Peptides against *Mycobacterium tuberculosis*," Antimicrobial Agents and Chemotherapy, vol. 55, No. 6, 2011, pp. 3058-3062.

Knight et al., "Sequence Programmable Peptoid Polymers for Diverse Materials Applications," Advanced Materials, vol. 27, No. 38, Oct. 1, 2015, pp. 5665-5691.

Kudirka et al., "Folding of a Single-Chain, Information-Rich Polypeptoid Sequence into a Highly Ordered Nanosheet," Biopolymers, vol. 96, No. 5, 2011, pp. 586-595.

Lau et al., "Molecular Design of Antifouling Polymer Brushes Using Sequence-Specific Peptoids," Adv. Mater. Interfaces, vol. 2, No. 1400225, 2015, pp. 1-10.

Lunt et al., "Investigation of Peptoid Thin Films and Their Potential Use in a Biosensor," Electrical Engineering and Computer Sciences, University of California at Berkeley, Technical Report No. USB/EECS-2013-111 https://digitalassets.lib.berkeley.edu/techreports/ucb/text/EECS-2013-111.pdf, 2013.

Mannige et al., "Peptoid Nanosheets Exhibit a New Secondary-Structure Motif," Nature, vol. 526, No. 7573, 2015, pp. 415-420.

Murphy et al., "A Combinatorial Approach to the Discovery of Efficient Cationic Peptoid Reagents for Gene Delivery," Proceedings of the National Academy of Sciences of the United States of America, vol. 95, No. 4, Feb. 1998, pp. 1517-1522.

Olivier et al., "Antibody-Mimetic Peptoid Nanosheets for Molecular Recognition," ACS Nano, vol. 7, No. 10, Sep. 9, 2013, pp. 9276-9286.

Olsen, "Beta-peptoid 'Foldamers'—Why the additional methylene unit?," Biopolymers, vol. 96, No. 5, Dec. 23, 2010, pp. 561-566.

Application No. PCT/US2018/027160, International Preliminary Report on Patentability, Mailed On Oct. 24, 2019, 20 pages.

Application No. PCT/US2018/027160, International Search Report and Written Opinion Received, Mailed On Jun. 11, 2018, 23 pages.

Peschko et al., "Dendrimer-Type Peptoid-Decorated Hexaphenylxylenes and Tetraphenylmethanes: Synthesis and Structure in Solution and in the Gas Phase," Chemistry A European Journal, vol. 20, No. 49, 2014, pp. 16273-16278.

Proulx et al., "On-Resin N-Terminal Peptoid Degradation: Toward Mild Sequencing Conditions," Biopolymer, vol. 106, No. 5, 2016, pp. 726-736.

Rosales et al., "Determination of the Persistence Length of Helical and Non-Helical Polypeptoids in Solution," Soft Matter, vol. 8, No. 13, 2012, pp. 3673-3680.

Sanii et al., "Structure-Determining Step in the Hierarchical Assembly of Peptoid Nanosheets," ACS Nano, vol. 8, No. 11, 2014, pp. 11674-11684.

Sun et al., "Nanoscale Phase Separation in Sequence-Defined Peptoid Diblock Copolymers," Journal of the American Chemical Society, vol. 135, No. 38, 2013, pp. 14119-14124.

Szekely et al., "From Glycopeptides to Glycopeptoids," Microreview, European Journal of Organic Chemistry, vol. 2014, No. 26, Sep. 2014, pp. 5641-5657.

Tran et al., "Solid-Phase Submonomer Synthesis of Peptoid Polymers and their Self-Assembly into Highly-Ordered Nanosheets," Journal of Visualized Experiments, vol. 57, No. 3373, 2011, 10 pages.

Turner et al., "Rationally Designed Peptoids Modulate Aggregation of Amyloid-Beta 40," ACS Chemical Neuroscience, vol. 5, No. 7, Apr. 1, 2014, pp. 552-558.

Yam et al., "A Universal Method for Detection of Amyloidogenic Misfolded Proteins," Biochemistry, vol. 50, No. 20, 2011, pp. 4322-4329.

Yang et al., "Synthesis of N-Alkyl Urea Peptoid Oligomers," University of Cincinnati, Department of Chemistry, Online Available at https://etd.ohiolink.edu/pg_10?0::NO:10:P10_ACCESSION_NUM:ucin1378197097, 2013, pp. 1-114.

Zuckerman, "Protein Mimicry with Bioinspired Peptoid Polymers," Proceedings of the 22nd American Peptide Symposium, 2011, pp. 174-175.

\* cited by examiner

Water    Cmpd. 1    EG    Cmpd. 10

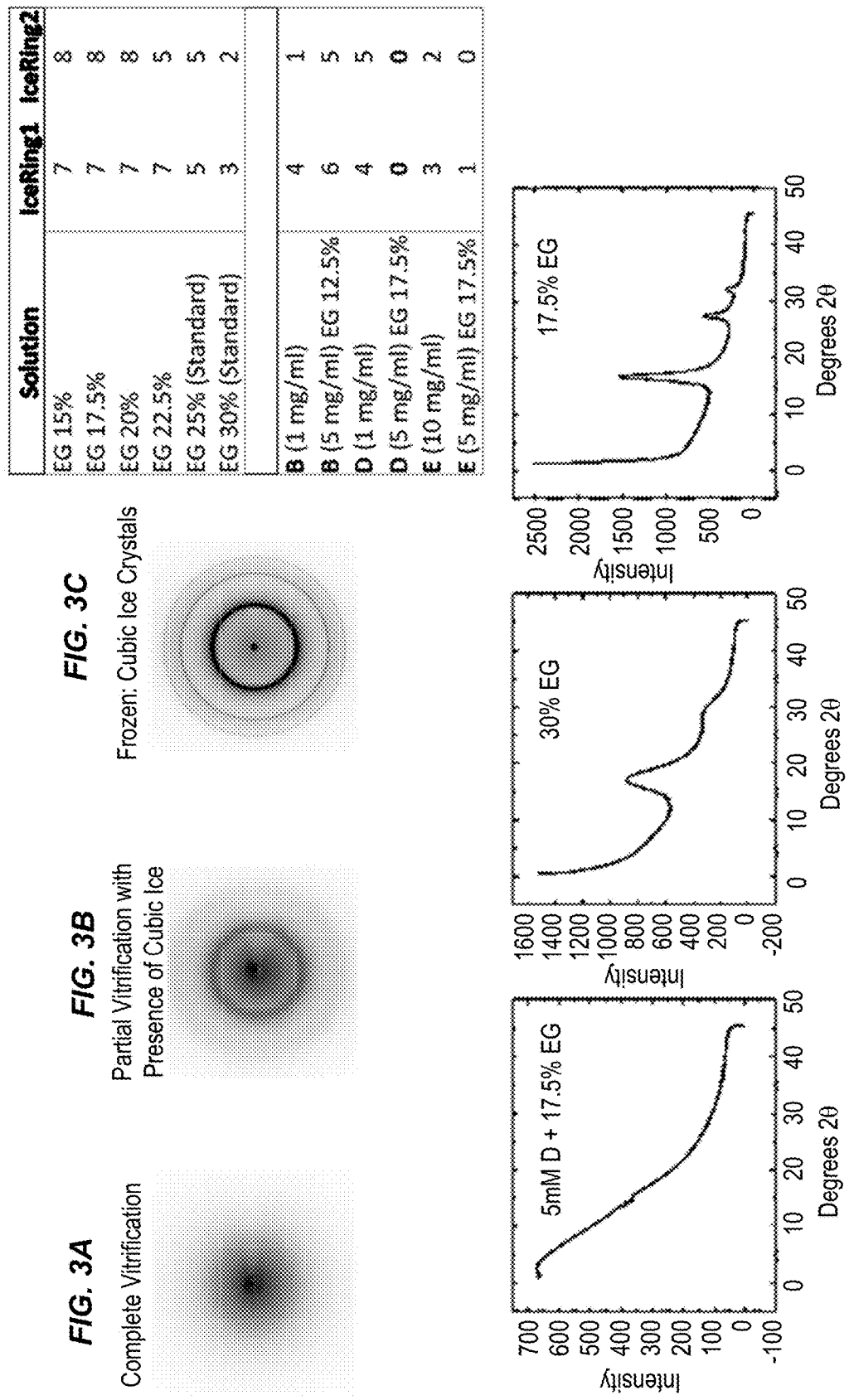
FIG. 3A Complete Vitrification
FIG. 3B Partial Vitrification with Presence of Cubic Ice
FIG. 3C Frozen: Cubic Ice Crystals
FIG. 3D (d) X-ray diffraction of ice formation
| Solution | IceRing1 | IceRing2 |
|---|---|---|
| EG 15% | 7 | 8 |
| EG 17.5% | 7 | 8 |
| EG 20% | 7 | 8 |
| EG 22.5% | 7 | 5 |
| EG 25% (Standard) | 5 | 5 |
| EG 30% (Standard) | 3 | 2 |
| B (1 mg/ml) | 4 | 1 |
| B (5 mg/ml) EG 12.5% | 6 | 5 |
| D (1 mg/ml) | 4 | 5 |
| D (5 mg/ml) EG 17.5% | 0 | 0 |
| E (10 mg/ml) | 3 | 2 |
| E (5 mg/ml) EG 17.5% | 1 | 0 |

*FIG. 4A*
Compound 10
5 mg/mL
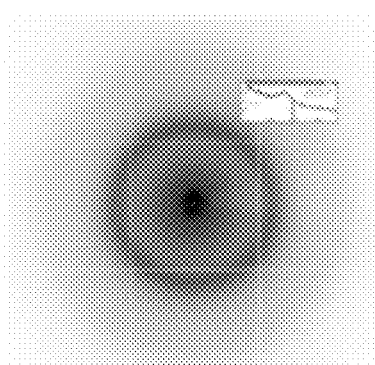
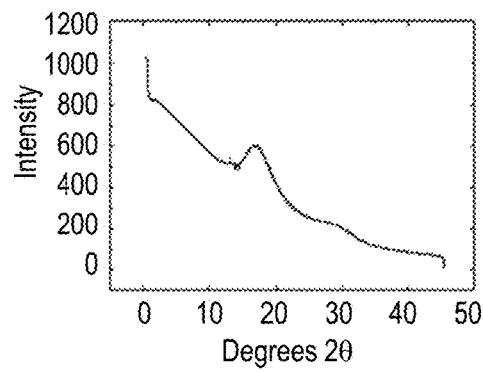
*FIG. 4B*
Compound 12
5 mg/mL
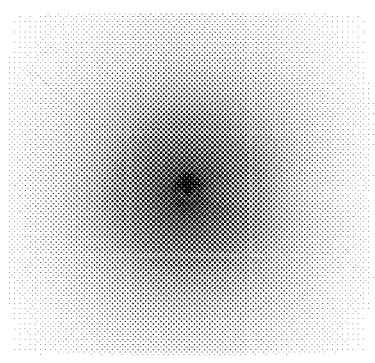
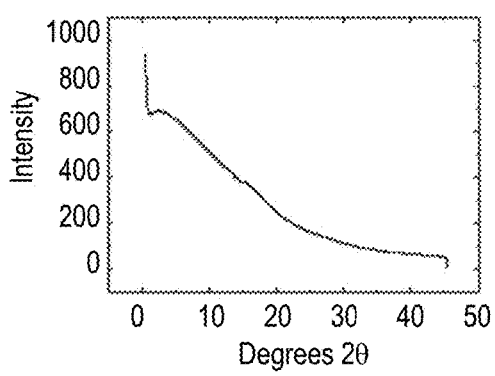
*FIG. 4C*
Compound 8
5 mg/mL
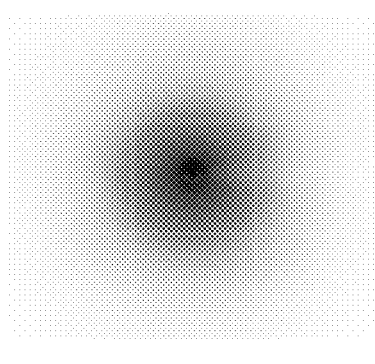
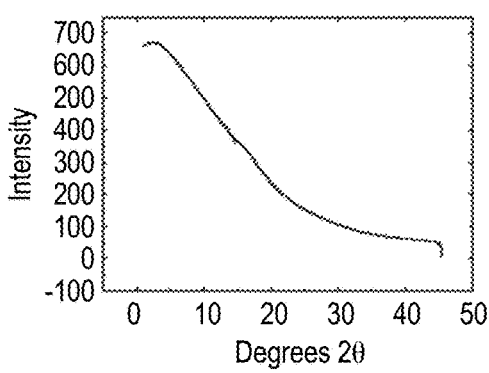
*FIG. 4D*
Compound 13
5 mg/mL
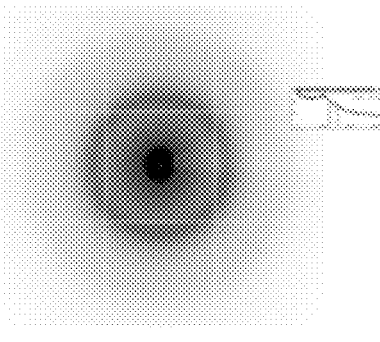
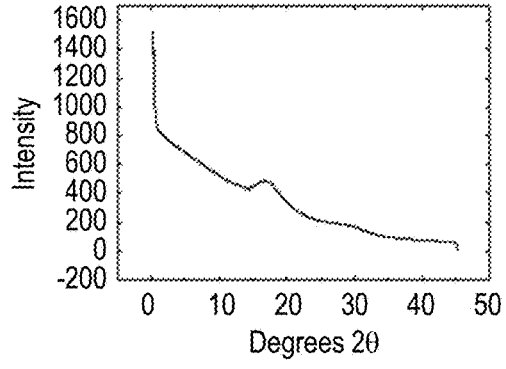

*Compound 11
5 mg/mL*

*Compound 58
5 mg/mL*

*Control
15% EG*

FIG. 5A
Compound 10
1 mg/mL
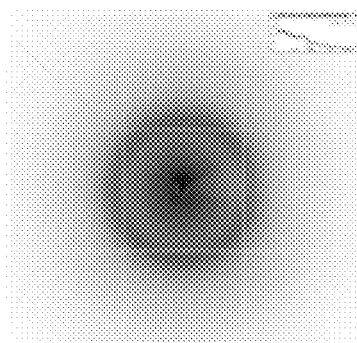
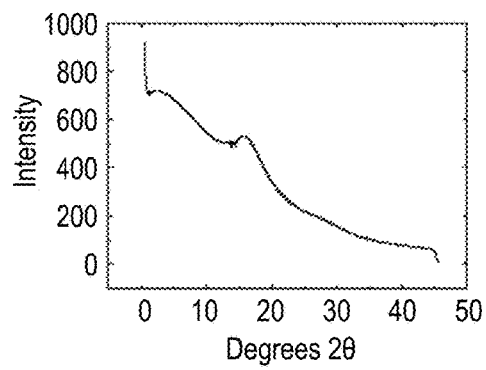
FIG. 5B
Compound 12
1 mg/mL
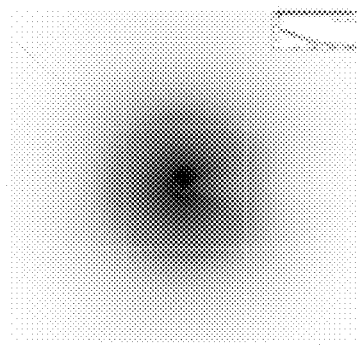
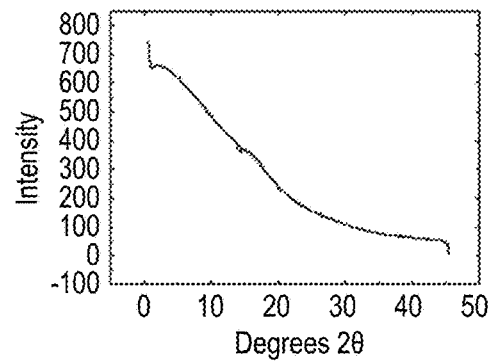
FIG. 5C
Compound 8
1 mg/mL
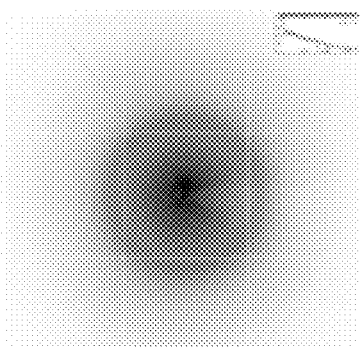
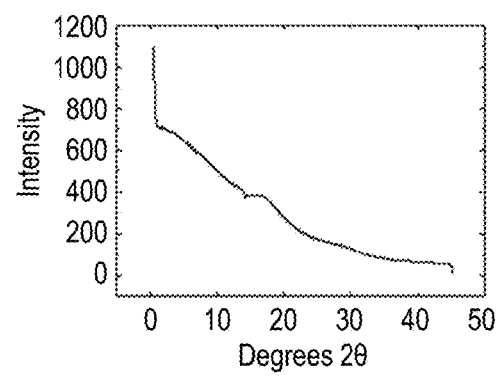
FIG. 5D
Compound 13
1 mg/mL
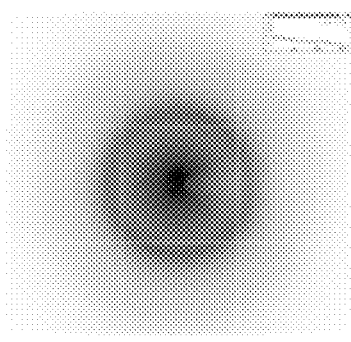
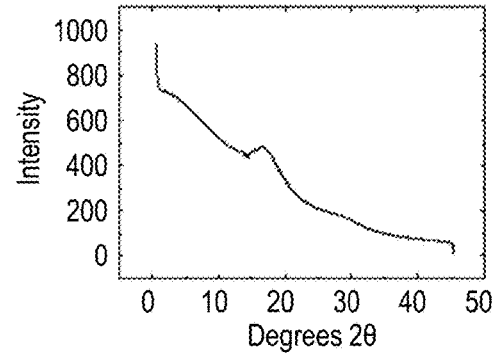

FIG. 5E
*Compound 11*
*1 mg/mL*
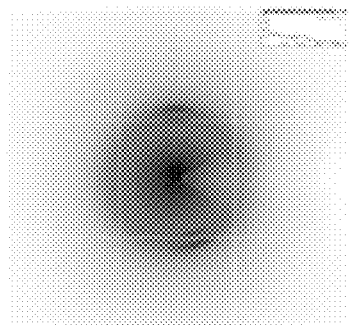 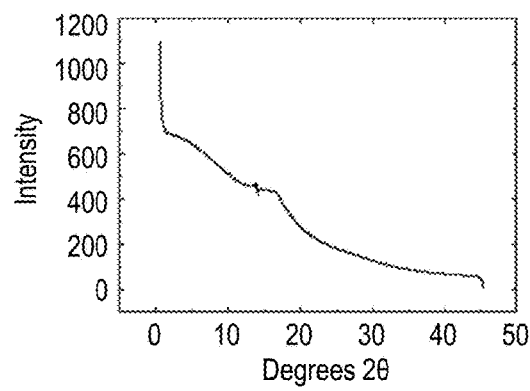
FIG. 5F
*Compound 58*
*1 mg/mL*
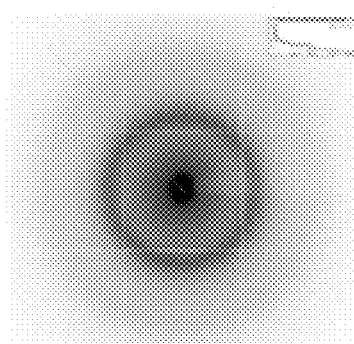 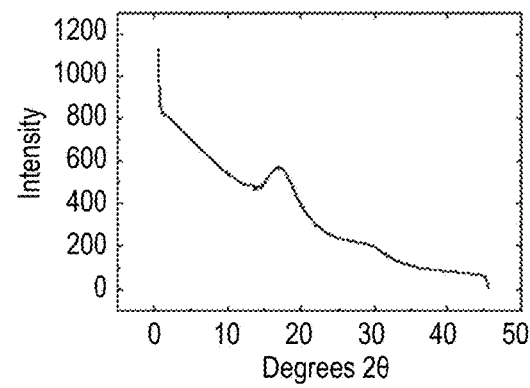
FIG. 5G
*Control*
*17.5% EG*
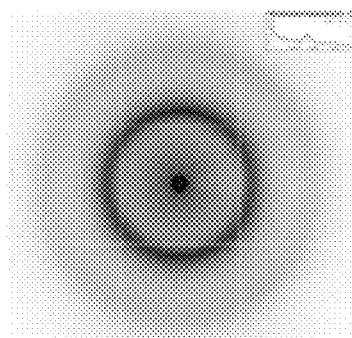 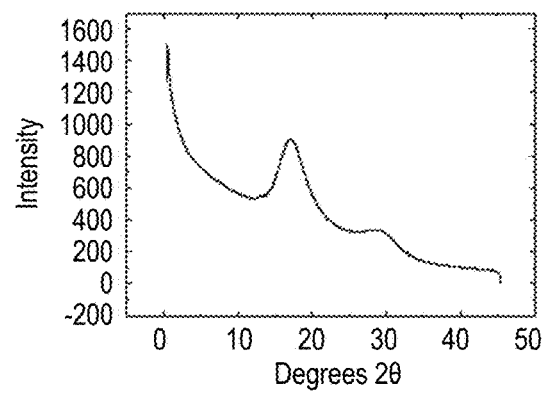

PEPTOID POLYMERS AND METHODS OF USE

CROSS-REFERENCE TO RELATED APPLICATIONS

This application is a continuation of U.S. patent application Ser. No. 16/583,885 filed on Sep. 26, 2019, which is a continuation of International Application No. PCT/US2018/027160 filed on Apr. 11, 2018, which claims priority to U.S. Provisional Application No. 62/484,714 filed on Apr. 12, 2017, the disclosures of which are herein incorporated by reference in their entirety for all purposes.

STATEMENT REGARDING FEDERALLY SPONSORED RESEARCH OR DEVELOPMENT

This invention was made with Government support under Contract No. W81XWH16C0066 awarded by the Department of Defense, Defense Health Agency. The Government has certain rights in the invention.

BACKGROUND OF THE INVENTION

Cryoprotective agents (CPAs) are compounds that when present in solution can reduce or inhibit ice crystal formation in solutions exposed to sub 0° C. temperatures. Current CPAs include small molecules (often referred to as penetrating CPAs), synthetic polymers, and antifreeze proteins.

Organ transplantation is currently the best treatment for end-stage organ failure in terms of survival, quality of life, and cost effectiveness. Unfortunately, a steep gap exists between the supply and demand of organs for transplantation, and this gap is one of the major medical obstacles that forces patients of debilitating diseases to suffer a low quality of life over a long period wait time. The apparent lack of organs is due to considerable waste resulting from the absence of a reliable preservation method. In fact, over 50% of lungs, pancreases, and hearts remain unharvested from deceased donors.

In order to properly preserve organs, they must be flushed with a preservation solution to remove blood and stabilize the organs. Even once stabilized in the preservation solution, there is only a limited time available for organ allocation, transportation, and transplantation after removal from the donor (~6-12 hours). This small timeframe results in most organs going to local patients because remote patient matches often cannot be confirmed in the limited time available. As a result of this shortage and in spite of laws which exist in almost all countries prohibiting the sale of one's organs, illicit organ trade and human trafficking has risen to satisfy demand.

Current penetrating CPAs used in organ preservation include ethylene glycol, 1,2-propanediol, dimethyl sulfoxide, formamide, glycerol, sucrose, lactose, and D-mannitol, generally among others. In order to reduce or inhibit ice crystal growth at organ preservation temperatures, the effective concentration of the penetrating CPAs must be very high (≥60% is often required). At such high concentrations these compounds can be toxic to the tissues they are attempting to preserve, and the massive removal of CPAs upon warming before transplantation can lead to irreversible cell death.

Other CPAs used to reduce or inhibit ice crystal formation include synthetic polymers and antifreeze proteins. Similar to the penetrating CPAs, each of these have their drawbacks. Synthetic polymers, for example, are not capable of permeating the cellular membrane. As such, synthetic polymer CPAs can only control extracellular ice formation. In order to effectively preserve the biological sample, ice crystal formation must be controlled both inside and outside the cell. Naturally-occurring antifreeze proteins, such as those isolated from fish, plants, or insects, are highly effective at preventing ice formation, but current antifreeze proteins that are available are of low purity and are extremely expensive. Additionally, the use of antifreeze proteins to preserve a biological sample introduces a potential source of immunogenicity.

As such, there is a need in the art for novel non-toxic compounds that effectively reduce or inhibit ice crystal formation at sub 0° C. and cryogenic temperatures. The present disclosure satisfies this need and provides other advantages as well.

BRIEF SUMMARY OF THE INVENTION

In one aspect, the present invention provides a peptoid polymer or a salt thereof comprising subunits comprising one or more first hydrophobic peptoid monomers H and one or more first polar peptoid monomers P arranged such that the peptoid polymer has the sequence $[H_aP_b]_n$ or $[P_bH_a]_n$, wherein the subscript a, representing the number of consecutive first hydrophobic peptoid monomers within a subunit, is between 1 and 10; the subscript b, representing the number of consecutive first polar peptoid monomers within a subunit, is between 1 and 10; and the subscript n, representing the number of subunits within the peptoid polymer, is between 2 and 50.

In some embodiments, the peptoid polymer or salt thereof further comprises substituents X and Y such that the peptoid polymer has the sequence $X-[H_aP_b]_n-Y$ or $X-[P_bH_a]_n-Y$, wherein X and Y are independently selected from the group consisting of H, optionally substituted $C_{1-8}$ alkyl, optionally substituted $C_{1-8}$ acyl, optionally substituted $C_{1-8}$ alkylamino, —OH, —SH, —NH$_2$, carboxy, optionally substituted $C_{1-8}$ hydroxyalkyl, optionally substituted $C_{1-8}$ alkylamino, optionally substituted $C_{2-8}$ alkylthio, optionally substituted $C_{1-8}$ carboxyalkyl, and halogen, or alternatively X and Y are taken together to form a covalent bond.

In some embodiments, the subunits further comprise a second hydrophobic peptoid monomer and/or a second polar peptoid monomer such that the peptoid polymer has the sequence $[H_aP_bH_cP_d]_n$ or $[P_bH_aP_dH_c]_n$, wherein the subscript c, representing the number of consecutive second hydrophobic peptoid monomers within a subunit, is between 0 and 10; the subscript d, representing the number of consecutive second polar peptoid monomers within a subunit, is between 0 and 10; and both c and d are not 0.

In some embodiments, the peptoid polymer or salt thereof further comprises substituents X and Y such that the peptoid polymer has the sequence $X-[H_aP_bH_cP_d]_n-Y$ or $X-[P_bH_aP_dH_c]_n-Y$, wherein X and Y are independently selected from the group consisting of H, optionally substituted $C_{1-8}$ alkyl, optionally substituted $C_{1-8}$ acyl, optionally substituted $C_{1-8}$ alkylamino, —OH, —SH, —NH$_2$, carboxy, optionally substituted $C_{1-8}$ hydroxyalkyl, optionally substituted $C_{1-8}$ alkylamino, optionally substituted $C_{2-8}$ alkylthio, optionally substituted $C_{1-8}$ carboxyalkyl, and halogen, or alternatively X and Y are taken together to form a covalent bond.

In some embodiments, the peptoid polymer or salt thereof further comprises a sequence Z that comprises one or more hydrophobic peptoid monomers and/or one or more polar peptoid monomers, wherein Z is located before the first subunit, after the last subunit, and/or between one or more subunits. In some instances, Z comprises one or more hydrophobic peptoid monomers. In other instances, Z comprises one or more polar peptoid monomers. In some other instances, Z comprises one or more hydrophobic peptoid monomers and one or more polar peptoid monomers.

In some embodiments, n is between 2 and 10. In other embodiments, a is between 1 and 5. In some other embodiments, b is between 1 and 5. In some instances, a is between 1 and 3 and b is between 1 and 3. In some embodiments, c is between 0 and 5. In other embodiments, d is between 0 and 5.

In another aspect, the present invention provides a peptoid polymer or a salt thereof comprising: (a) subunits comprising two first hydrophobic peptoid monomers H and two first polar peptoid monomers P, and (b) two second hydrophobic peptoid monomers located at the C-terminal end of the peptoid polymer, arranged such that the peptoid polymer has the sequence $[H_2P_2]_nH_2$ or $[P_2H_2]_nH_2$, wherein the subscript n, representing the number of subunits within the peptoid polymer, is between 1 and 50. In some embodiments, n is between 1 and 10. In some embodiments, the peptoid polymer or salt thereof comprises Compound 81.

In some embodiments, the peptoid polymer or salt thereof further comprises substituents X and Y such that the peptoid polymer has the sequence X—$[H_2P_2]_nH_2$—Y or X—$[P_2H_2]_nH_2$—Y, wherein X and Y are independently selected from the group consisting of H, optionally substituted $C_{1-8}$ alkyl, optionally substituted $C_{1-8}$ acyl, optionally substituted $C_{1-8}$ alkylamino, —OH, —SH, —NH$_2$, carboxy, optionally substituted $C_{1-8}$ hydroxyalkyl, optionally substituted $C_{1-8}$ alkylamino, optionally substituted $C_{2-8}$ alkylthio, optionally substituted $C_{1-8}$ carboxyalkyl, and halogen, or alternatively X and Y are taken together to form a covalent bond.

In some embodiments, the first and/or second hydrophobic peptoid monomers are independently selected from the group consisting of

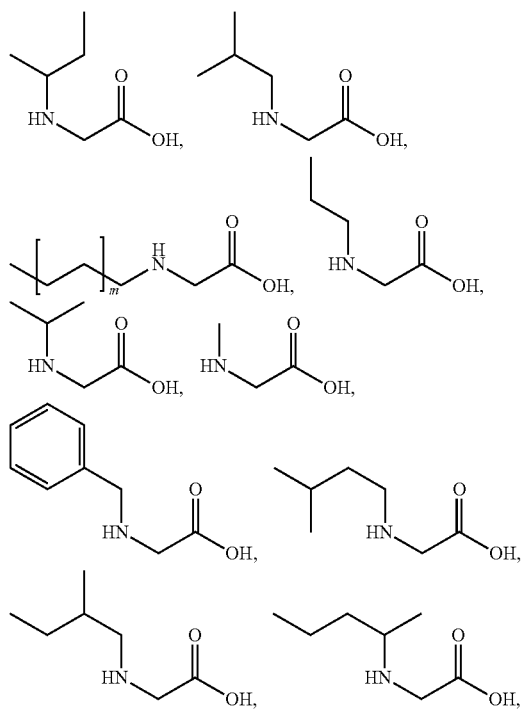

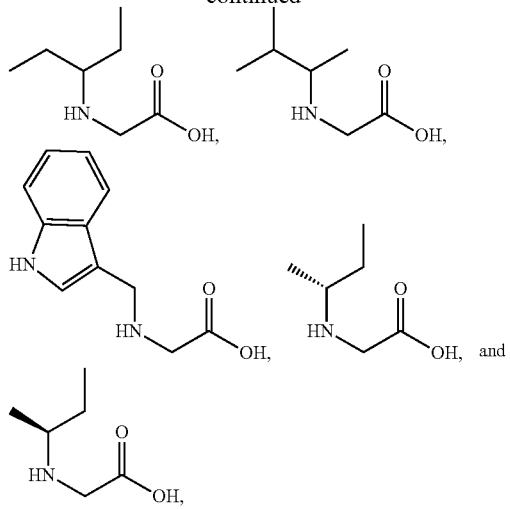

wherein the subscript m is the number of repeat units and is between 1 and 10.

In some embodiments, none of the polar peptoid monomers comprise a side chain that comprises an optionally substituted $C_{1-18}$ hydroxyalkyl group.

In some embodiments, each of the first and/or second polar peptoid monomers comprise a side chain that is independently selected from the group consisting of ($C_{1-6}$ alkoxy)($C_{1-6}$ alkylene), (oligo[ethylene glycol]), (4- to 10-membered heterocycloalkyl)($C_{1-6}$ alkylene), and (5- to 10-membered heteroaryl)($C_{1-6}$ alkylene). In some embodiments, (4- to 10-membered heterocycloalkyl)($C_{1-6}$ alkylene) comprises a 4-6 membered heterocyclic ring, wherein at least one member is selected from the group consisting of O and N. In some embodiments, (4- to 10-membered heterocycloalkyl)($C_{1-6}$ alkylene) comprises a tetrahydrofuranyl or oxopyrrolidinyl moiety. In some instances, the peptoid polymer comprises

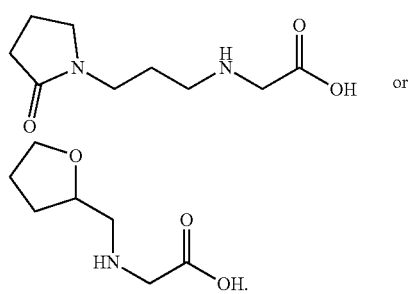

In particular instances, all of the polar peptoid monomers are

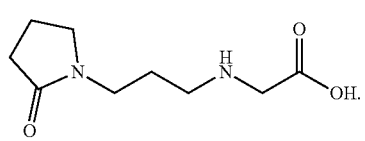 [SMILES: O=C(O)CNCCCN1CCCC1=O]

In some embodiments, the peptoid polymer comprises Compound 63, Compound 76, Compound 86, or Compound 87.

In some embodiments, (5- to 10-membered heteroaryl)($C_{1-6}$ alkylene) comprises a 5-6 membered aromatic ring, wherein at least one ring member is selected from the group consisting of O and N. In some embodiments, (5- to 10-membered heteroaryl)(C$_{1-6}$ alkylene) comprises a furanyl moiety. In some instances, the peptoid polymer comprises

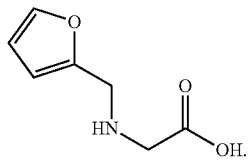 [SMILES: O=C(O)CNCc1ccco1]

In particular instances, the peptoid polymer comprises Compound 73.

In some embodiments, the side chain comprises a methoxyethyl group. In some instances, the peptoid polymer comprises

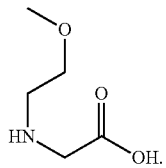

In particular instances, the peptoid polymer comprises Compound 62.

In some embodiments, the side chain comprises an oligo (ethylene glycol) moiety. In some embodiments, the oligo (ethylene glycol) moiety is a 2-(2-(2-methoxyethoxy) ethoxy)ethyl moiety. In some instances, the peptoid polymer comprises

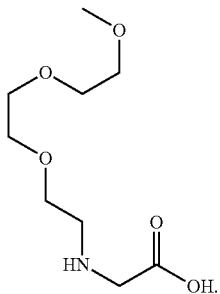

In particular instances, the peptoid polymer comprises Compound 67.

In some embodiments, the peptoid polymer or salt thereof comprises a polar peptoid monomer having a side chain that comprises a hydroxyl group. In other embodiments, the first and/or second polar peptoid monomers are independently selected from the group consisting of

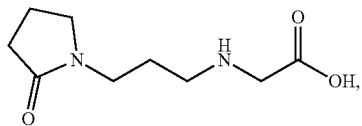

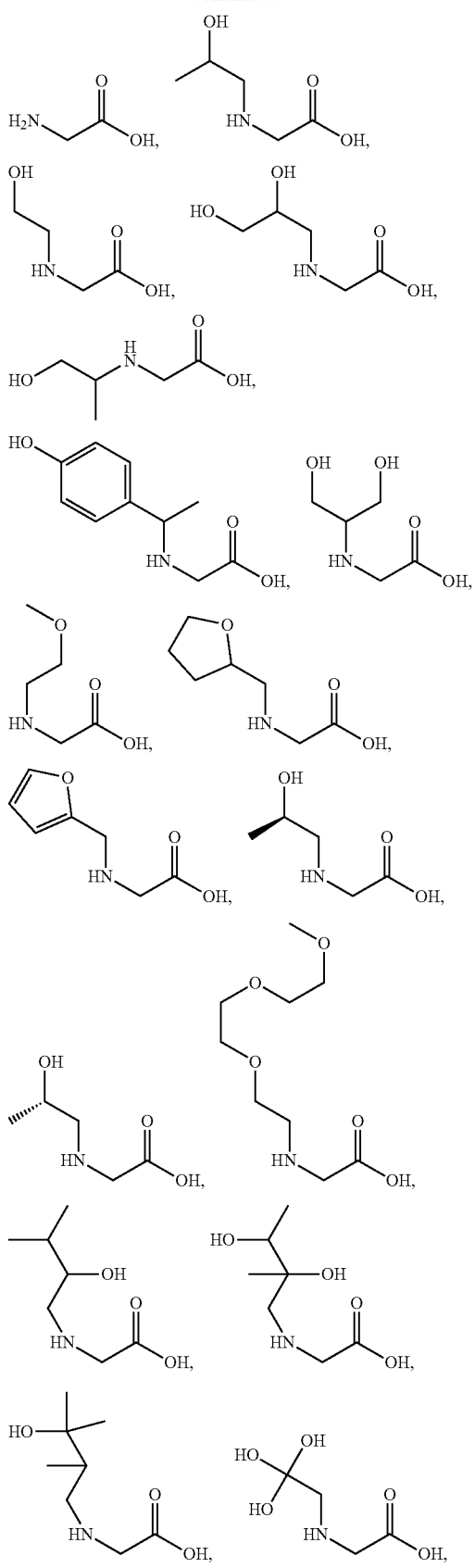

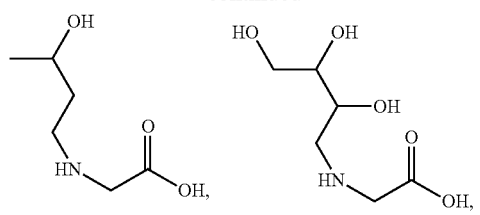
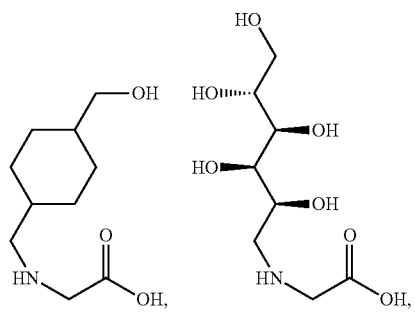
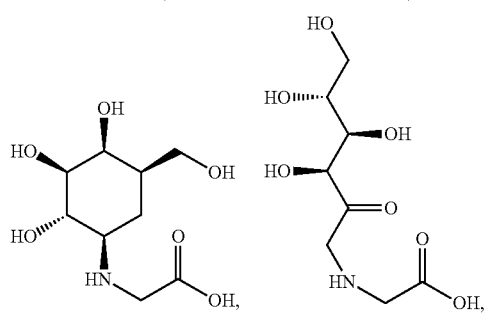
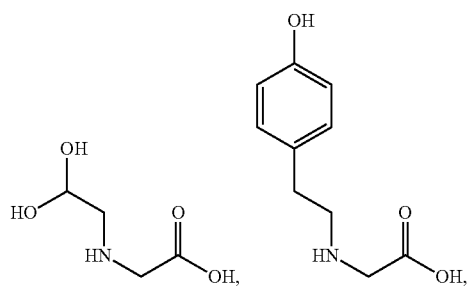
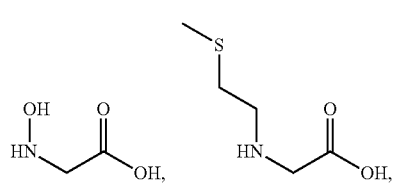
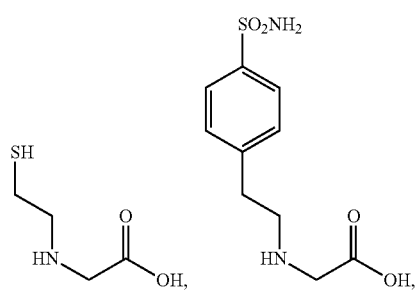
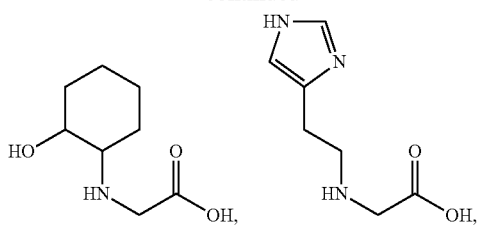
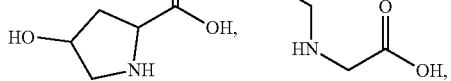
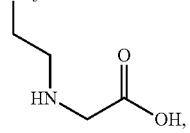
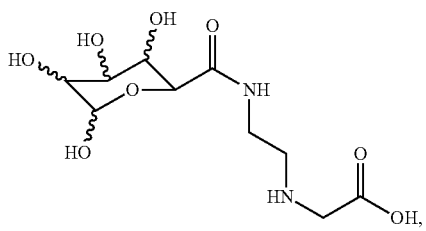
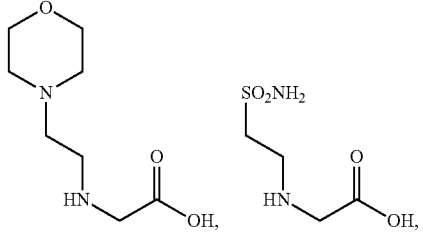
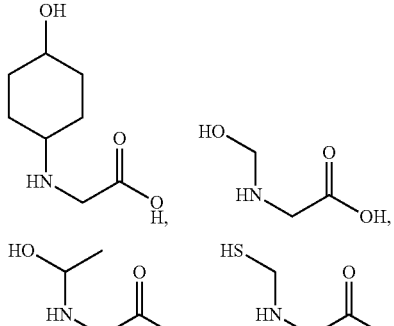
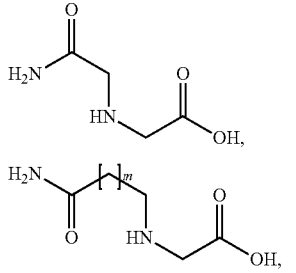

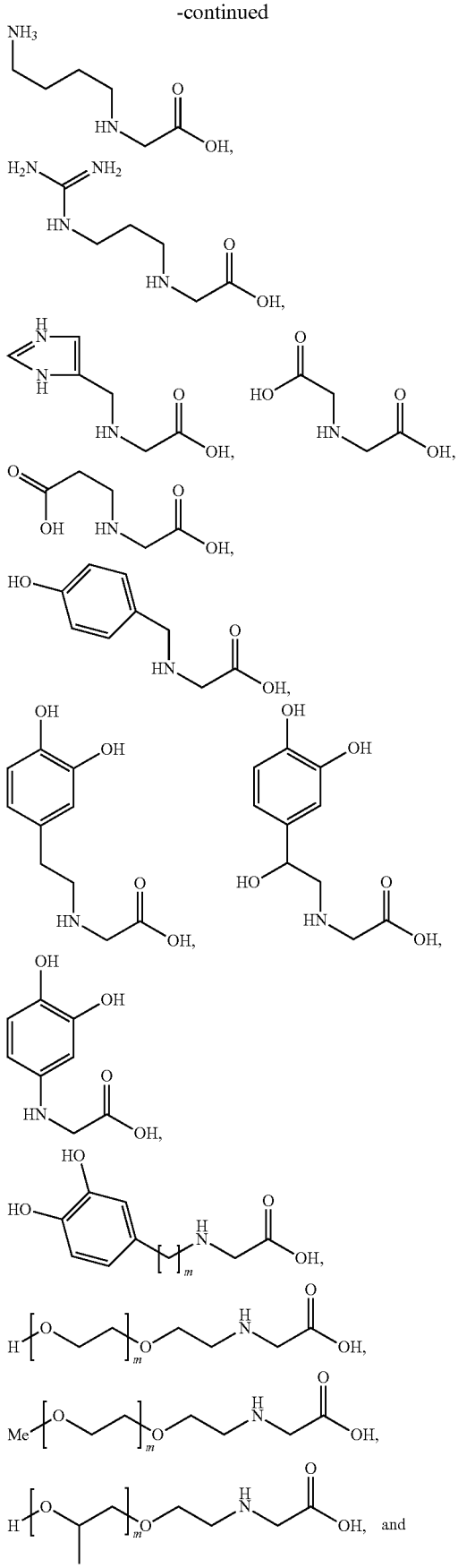

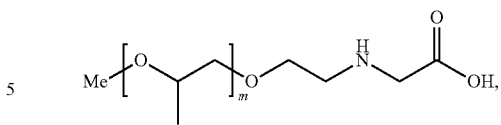

wherein the subscript m is the number of repeat units and is between 1 and 10.

In another aspect, the present invention provides a peptoid polymer or a salt thereof comprising one or more hydrophobic peptoid monomers and one or more polar peptoid monomers, wherein each of the one or more polar peptoid monomers comprise a side chain that is independently selected from the group consisting of $(C_{1-6}$ alkoxy)$(C_{1-6}$ alkylene), (oligo[ethylene glycol]), (4- to 10-membered heterocycloalkyl)$(C_{1-6}$ alkylene), and (5- to 10-membered heteroaryl)$(C_{1-6}$ alkylene).

In some embodiments, each of the one or more hydrophobic peptoid monomers is independently selected from the group consisting of

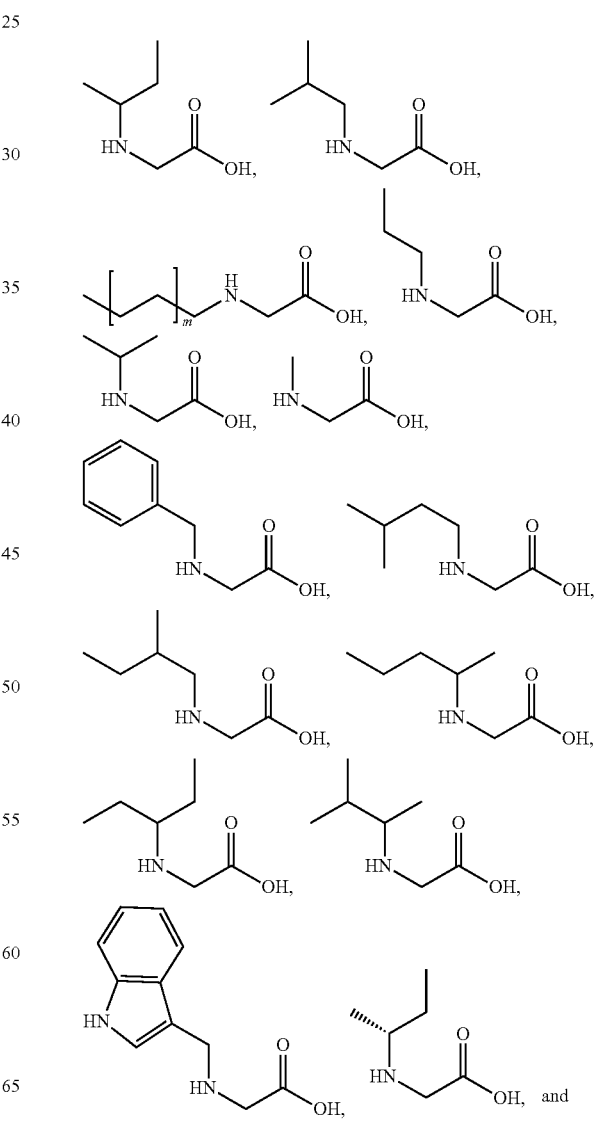

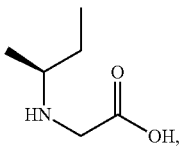

wherein the subscript m is the number of repeat units and is between 1 and 10.

In some embodiments, (4- to 10-membered heterocycloalkyl)($C_{1-6}$ alkylene) comprises a 4-6 membered heterocyclic ring, wherein at least one member is selected from the group consisting of O and N. In some embodiments, (4- to 10-membered heterocycloalkyl)($C_{1-6}$ alkylene) comprises a tetrahydrofuranyl or oxopyrrolidinyl moiety. In some instances, the peptoid polymer comprises

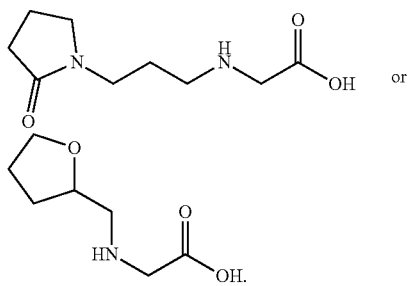

In particular instances, all of the polar peptoid monomers are

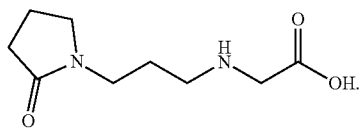 [SMILES: O=C(O)CNCCCN1CCCC1=O]

In some embodiments, the peptoid polymer comprises Compound 63, Compound 76, Compound 86, or Compound 87.

In some embodiments, (5- to 10-membered heteroaryl)($C_{1-6}$ alkylene) comprises a 5-6 membered aromatic ring, wherein at least one ring member is selected from the group consisting of O and N. In some embodiments, (5- to 10-membered heteroaryl)($C_{1-6}$ alkylene) comprises a furanyl moiety. In some instances, the peptoid polymer comprises

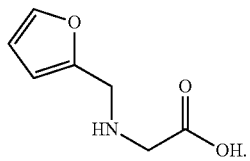 [SMILES: O=C(O)CNCc1ccco1]

In particular instances, the peptoid polymer comprises Compound 73.

In some embodiments, the side chain comprises a methoxyethyl group. In some instances, the peptoid polymer comprises

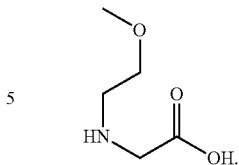

In particular instances, the peptoid polymer comprises Compound 62.

In some embodiments, the side chain comprises an oligo(ethylene glycol) moiety. In some embodiments, the oligo(ethylene glycol) moiety is a 2-(2-(2-methoxyethoxy)ethoxy)ethyl moiety. In some instances, the peptoid polymer comprises

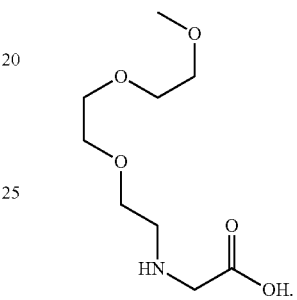

In particular instances, the peptoid polymer comprises Compound 67.

In some embodiments, the peptoid polymer or salt thereof further comprises substituents X and Y located at the N-terminal and C-terminal ends of the peptoid polymer, respectively, wherein X and Y are independently selected from the group consisting of H, optionally substituted $C_{1-8}$ alkyl, optionally substituted $C_{1-8}$ acyl, optionally substituted $C_{1-8}$ alkylamino, —OH, —SH, —NH$_2$, carboxy, optionally substituted $C_{1-8}$ hydroxyalkyl, optionally substituted $C_{1-8}$ alkylamino, optionally substituted $C_{2-8}$ alkylthio, optionally substituted $C_{1-8}$ carboxyalkyl, and halogen, or alternatively X and Y are taken together to form a covalent bond.

In some embodiments, about 10 percent of the peptoid monomers are hydrophobic. In some embodiments, about 20 percent of the peptoid monomers are hydrophobic. In some embodiments, about 30 percent of the peptoid monomers are hydrophobic. In some embodiments, about 40 percent of the peptoid monomers are hydrophobic. In some embodiments, about 50 percent of the peptoid monomers are hydrophobic. In some embodiments, about 60 percent of the peptoid monomers are hydrophobic. In some embodiments, about 70 percent of the peptoid monomers are hydrophobic. In some embodiments, about 80 percent of the peptoid monomers are hydrophobic. In some embodiments, about 90 percent of the peptoid monomers are hydrophobic.

In some embodiments, the peptoid polymer forms a helical structure. In other embodiments, the peptoid polymer or salt thereof reduces or inhibits ice crystal formation at a temperature within about 0° C. to about −20° C. In some embodiments, the peptoid polymer or salt thereof reduces or inhibits ice crystal formation at a temperature within about −20° C. to about −40° C. In other embodiments, the peptoid polymer or salt thereof reduces or inhibits ice crystal formation at a temperature of about −20° C. In some other embodiments, the peptoid polymer or salt thereof reduces or inhibits ice crystal formation at a temperature within about −40° C. to about −200° C. In some embodiments, the peptoid polymer salt is selected from the group consisting of a hydrochloride salt, acetate salt, sulfate salt, phosphate salt, maleate salt, citrate salt, mesylate salt, nitrate salt, tartrate salt, gluconate salt, and a combination thereof. In some embodiments, the peptoid polymer is not a peptoid polymer set forth in Tables 2-9.

In another aspect, the present invention provides a peptoid-peptide hybrid or salt thereof comprising a peptoid polymer of the present invention and one or more amino acids, wherein the one or more amino acids are located at one or both ends of the peptoid polymer and/or between one or more subunits. In some embodiments, the peptoid-peptide hybrid is not Nep-Nep-Xaa-Xaa-Xaa-Xaa-Nep-Nep-Nep-Nep-Nme-Nme, Nme-Nme-Xaa-Nme-Nme-Nme-Nme-Nhp-Nhp-Nsb-Xaa-Nme-Nme-Xaa-Nme-Nme-Nme, Nme-Nme-Xaa-Nme-Nme-Nme-Nme-Nme-Nme-Nme-Xaa-Xaa, or Arg-Nsb-Nsb-Nhp-Nhp-Nsb-Nsb-Nhp-Nhp-Nsb-Nsb. In other embodiments, the one or more amino acids are selected from the group consisting of alanine, cysteine, aspartic acid, glutamic acid, phenylalanine, glycine, histidine, isoleucine, arginine, lysine, leucine, methionine, asparagine, proline, glutamine, serine, threonine, valine, tryptophan, tyrosine, and a combination thereof. In particular embodiments, the one or more amino acids are selected from the group consisting of isoleucine, leucine, serine, threonine, alanine, valine, arginine, and a combination thereof. In some embodiments, the peptoid-peptide hybrid salt is selected from the group consisting of a hydrochloride salt, acetate salt, sulfate salt, phosphate salt, maleate salt, citrate salt, mesylate salt, nitrate salt, tartrate salt, gluconate salt, and a combination thereof.

In another aspect, the present invention provides a cryoprotectant solution comprising a peptoid polymer or salt thereof of the present invention, a peptoid-peptide hybrid or salt thereof of the present invention, or a combination thereof. In some embodiments, the cryoprotectant solution further comprises a compound selected from the group consisting of an ionic species, a penetrating cryoprotectant, a non-penetrating cryoprotectant, an antioxidant, a cell membrane stabilizing compound, an aquaporin or other channel forming compound, an alcohol, a sugar, a sugar derivative, a nonionic surfactant, a protein, dimethyl sulfoxide (DMSO), polyethylene glycol (PEG), polypropylene glycol (PPG), Ficoll©, polyvinylpyrrolidone, polyvinyl alcohol, hyaluronan, formamide, a natural or synthetic hydrogel, and a combination thereof.

In some instances, the cryoprotectant solution further comprises an alcohol selected from the group consisting of propylene glycol, ethylene glycol, glycerol, methanol, butylene glycol, adonitol, ethanol, trimethylene glycol, diethylene glycol, polyethylene oxide, erythritol, sorbitol, xythyritol, polypropylene glycol, 2-methyl-2,4-pentanediol (MPD), mannitol, inositol, dithioritol, 1,2-propanediol, and a combination thereof.

In some instances, the cryoprotectant solution further comprises a sugar that is selected from the group consisting of a monosaccharide, a disaccharide, a polysaccharide, and a combination thereof. In some instances, the sugar is a monosaccharide selected from the group consisting of glucose, galactose, arabinose, fructose, xylose, mannose, 3-O-methyl-D-glucopyranose, and a combination thereof. In other instances, the sugar is a disaccharide selected from the group consisting of sucrose, trehalose, lactose, maltose, and a combination thereof. In still other instances, the sugar is a polysaccharide selected from the group consisting of raffinose, dextran, and a combination thereof.

In other instances, the cryoprotectant solution further comprises a PEG or PPG that has an average molecular weight less than about 3,000 g/mol. In particular instances, the PEG or PPG has an average molecular weight between about 200 g/mol and 400 g/mol.

In some instances, the cryoprotectant solution further comprises a protein selected from the group consisting of bovine serum albumin, human serum albumin, gelatin, and a combination thereof. In other instances, the cryoprotectant solution further comprises a natural or synthetic hydrogel that comprises chitosan, hyaluronic acid, or a combination thereof. In yet other instances, the cryoprotectant solution further comprises a nonionic surfactant selected from the group consisting of polyoxyethylene lauryl ether, polysorbate 80, and a combination thereof.

In another aspect, the present invention provides a method for preserving a tissue, an organ, or a cell. In some embodiments, the method comprises contacting the tissue, organ, or cell with a peptoid polymer or salt thereof of the present invention, a peptoid-peptide hybrid or salt thereof of the present invention, a cryoprotectant solution of the present invention, or a combination thereof. In some embodiments, the tissue is a bioengineered tissue. In other embodiments, the tissue, organ, or cell is selected from the group consisting of heart, liver, lung, kidney, pancreas, intestine, thymus, cornea, nerve cells, blood platelets, sperm cells, oocytes, genitourinary cells, embryonic cells, stem cells, human pluripotent stem cells, hematopoietic stem cells, lymphocytes, granulocytes, immune system cells, bone cells, primary cells, organoids, and a combination thereof.

In some embodiments, the peptoid polymer or salt thereof, peptoid-peptide hybrid or salt thereof, cryoprotectant solution, or combination thereof is present in an amount sufficient to reduce or inhibit ice crystal formation at a temperature within about 0° C. to about −20° C. In other embodiments, the peptoid polymer or salt thereof, peptoid-peptide hybrid or salt thereof, cryoprotectant solution, or combination thereof is present in an amount sufficient to reduce or inhibit ice crystal formation at a temperature within about −20° C. to about −40° C. In some embodiments, the peptoid polymer or salt thereof, peptoid-peptide hybrid or salt thereof, cryoprotectant solution, or combination thereof is present in an amount sufficient to reduce or inhibit ice crystal formation at about −20° C. In other embodiments, the peptoid polymer or salt thereof, peptoid-peptide hybrid or salt thereof, cryoprotectant solution, or combination thereof is present in an amount sufficient to reduce or inhibit ice crystal formation at a temperature within about −40° C. to about −200° C. (e.g., −196° C.). In certain embodiments, the concentration of the peptoid polymer or salt thereof and/or peptoid-peptide hybrid or salt thereof in the cryoprotectant solution is between about 100 nM and about 1,000 mM. In particular embodiments, the concentration of the peptoid polymer or salt thereof and/or peptoid-peptide hybrid or salt thereof in the cryoprotectant solution is between about 1 and 100 mM (e.g., about 1, 2, 3, 4, 5, 6, 7, 8, 9, 10, 20, 30, 40, 50, 60, 70, 80, 90, or 100 mM).

In yet another aspect, the present invention provides a method for preserving a biological macromolecule. In some embodiments, the method comprises contacting the biological macromolecule with a peptoid polymer or salt thereof of the present invention, a peptoid-peptide hybrid or salt thereof of the present invention, a cryoprotectant solution of the present invention, or a combination thereof. In some embodiments, the biological macromolecule is selected from the group consisting of a nucleic acid, an amino acid, a protein, an isolated protein, a peptide, a lipid, a composite structure, and a combination thereof.

In another aspect, the present invention provides a cosmetic care product comprising a peptoid polymer or salt thereof of the present invention, a peptoid-peptide hybrid or salt thereof of the present invention, a cryoprotectant solution of the present invention, or a combination thereof.

In another aspect, the present invention provides an antifreeze product such as a deicing or ice-inhibiting product comprising a peptoid polymer or salt thereof of the present invention, a peptoid-peptide hybrid or salt thereof of the present invention, a cryoprotectant solution of the present invention, or a combination thereof. In some embodiments, the antifreeze product is used to prevent, inhibit, or delay the formation of ice on or within objects including, but not limited to, aircraft or parts thereof, gas pipelines, windows, electrical equipment, drones, cables (e.g., power lines), mechanical equipment (e.g., car engines, gear systems, brake systems, etc.), and the like.

In still another aspect, the present invention provides a frozen food product comprising a peptoid polymer or salt thereof of the present invention, a peptoid-peptide hybrid or salt thereof of the present invention, a cryoprotectant solution of the present invention, or a combination thereof. In some embodiments, the frozen food product is selected from the group consisting of ice cream, yogurt, seafood, fruit, and meat products.

Other objects, features, and advantages of the present invention will be apparent to one of skill in the art from the following detailed description and figures.

BRIEF DESCRIPTION OF THE DRAWINGS

FIG. 2A illustrates the assay in which Compounds 1 (1 eq.) and 10 (1 eq.) were dissolved in MilliQ water and subjected to subzero temperatures. Comparison was made to water alone and a solution of ethylene glycol (EG) (18 eq.). FIG. 2B displays normalized results of the assay depicted in FIG. 2A.

FIGS. 3A-3D show x-ray diffraction (XRD) crystallography data. FIG. 3A shows XRD data for a solution containing 5 mM Compound 12 and 17.5% (v/v) ethylene glycol (EG). FIG. 3B shows XRD data for a solution containing 30% (v/v) EG. FIG. 3C shows XRD data for a solution containing 17.5% (v/v) EG. FIG. 3D shows ice ring scores for a number of solutions containing EG, Compound 2 (labeled as "B"), Compound 12 (labeled as "D"), and/or Compound 8 (labeled as "E"). For each different solution, two separate ice ring scores were determined.

FIGS. 4A-4G show x-ray diffraction (XRD) crystallography data for solutions containing 5 mg/mL of Compound 10, Compound 12, Compound 8, Compound 13, Compound 11, and Compound 58, compared to an ethylene glycol (EG) control. Each solution also contained 300 mM NaCl, 100 mM HEPES, 15% (v/v) ethylene glycol, and pH was adjusted to 7.2. FIG. 4A: Compound 10 XRD crystallography pattern (left) and spectrum plot (right). FIG. 4B: Compound 12 XRD crystallography pattern (left) and spectrum plot (right). FIG. 4C: Compound 8 XRD crystallography pattern (left) and spectrum plot (right). FIG. 4D: Compound 13 XRD crystallography pattern (left) and spectrum plot (right). FIG. 4E: Compound 11 XRD crystallography pattern (left) and spectrum plot (right). FIG. 4F: Compound 58 XRD crystallography pattern (left) and spectrum plot (right). FIG. 4G: EG control XRD crystallography pattern (left) and spectrum plot (right). For XRD spectrum plots, intensity was plotted as a function of angle (2θ degrees).

FIGS. 5A-5G show x-ray diffraction (XRD) crystallography data for solutions containing 1 mg/mL of Compound 10, Compound 12, Compound 8, Compound 13, Compound 11, and Compound 58, compared to an ethylene glycol (EG) control. Each solution also contained 300 mM NaCl, 100 mM HEPES, 17.5% (v/v) ethylene glycol, and pH was adjusted to 7.2. FIG. 5A: Compound 10 XRD crystallography pattern (left) and spectrum plot (right). FIG. 5B: Compound 12 XRD crystallography pattern (left) and spectrum plot (right). FIG. 5C: Compound 8 XRD crystallography pattern (left) and spectrum plot (right). FIG. 5D: Compound 13 XRD crystallography pattern (left) and spectrum plot (right). FIG. 5E: Compound 11 XRD crystallography pattern (left) and spectrum plot (right). FIG. 5F: Compound 58 XRD crystallography pattern (left) and spectrum plot (right). FIG. 5G: EG control XRD crystallography pattern (left) and spectrum plot (right). For XRD spectrum plots, intensity was plotted as a function of angle (2θ degrees).

FIG. 6A shows that during rapid freezing in liquid nitrogen, the solution containing Compound 12 vitrified while the control solution completely froze. FIG. 6B shows that during rewarming at 37° C., the solution containing Compound 12 unfroze (within two seconds) while the control stayed frozen. FIG. 6C shows that after overnight in a −20° C. freezer, the Compound 12 solution remained unfrozen, unlike the control.

DETAILED DESCRIPTION OF THE INVENTION

I. Introduction

Figure 1:
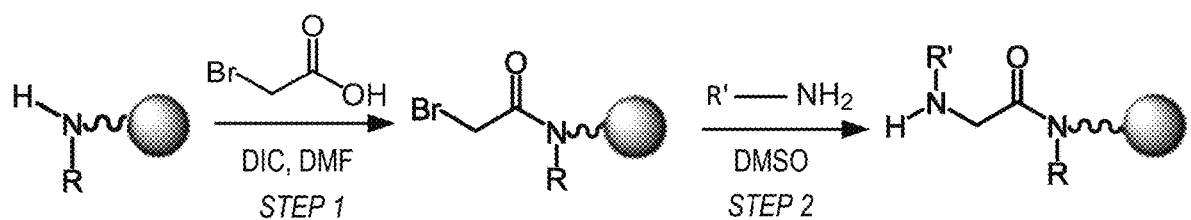
FIG. 1 illustrates a general protocol for the synthesis of peptoid oligomers using the "submonomer" approach.

The banking of cells and tissues at low temperatures using cryopreservation is critical for many biological products and applications, but remains a significant problem that has yet to allow the successful full recovery or viable therapeutic cells, tissues, and organs. Cryopreservation is typically performed with cryoprotective agents (CPAs), which are critical chemical additives such as dimethyl sulfoxide (DMSO), bovine serum albumin (BSA), and others. The CPAs are used to improve the post-thaw viability of cryopreserved biological systems by preventing ice crystal nucleation and growth. However, these agents exhibit various levels of cytotoxicity at their effective concentrations and thus limit the success of cryopreservation, biobanking, and advanced regenerative medicine. This lack of an effective and safe CPA contributes to the widespread use of toxic CPAs. Beyond biological products and applications, preventing ice formation remains a physical and chemical problem for a large number of industries and technology sectors.

The present invention is based, in part, on the surprising discovery that N-substituted biomimetic amino acid polymers (peptoids) and peptoid-peptide hybrids have ice crystallization inhibition properties. Furthermore, the present invention is based, in part, on the discovery that particular combinations of hydrophobic and polar peptoid monomers are useful for augmenting the ice crystallization inhibition properties of the compositions disclosed herein. Provided herein are polymers for reducing or inhibiting ice crystal formation at sub 0° C. and cryogenic temperatures. These polymers are useful in making cryoprotectant solutions. Also provided herein are methods for preserving a tissue, organ, or cell using cryoprotectant solutions comprising use of the peptoid polymers, peptoid-peptide hybrids, and/or salts thereof described herein. Additionally, cosmetic care, deicing, and frozen food products with antifreeze properties comprising the peptoid polymers, peptoid-peptide hybrids, and/or salts thereof described herein are provided. Upon reading the detailed description, a person of ordinary skill in the art will recognize there are other advantages that flow from the teachings provided herein.

II. Abbreviations and Definitions

The abbreviations used herein are conventional, unless otherwise defined. The following abbreviations are used to refer to particular monomer units of the peptoid polymer: Nsb (2-(sec-butylamino)acetic acid), Nib (2-(isobutylamino)acetic acid), Nbu (2-butylamino)acetic acid), Npr (2-propylamino)acetic acid), Nip (2-(isopropylamino)acetic acid), Nme (2-(methylamino)acetic acid), Nhp (2-((2-hydroxypropyl)amino)acetic acid), Nhe (2-((2-hydroxyethyl)amino)acetic acid), Ndp (2-((2,3-dihydroxypropryl)amino) acetic acid, Nyp (2-((1-hydroxypropan-2-yl)amino) acetic acid), Nep (2-((1-(4-hydroxyphenyl)ethyl)amino) acetic acid, Ndh (2-((1,3,-dihydrooxypropan-2-yl)amino)acetic acid, Nop (2-((3-(2-oxopyrrolindin-1-yl)propyl)amino)acetic acid, Nmo (2-(2-methoxyethylamino)acetic acid), Ntf (2-((tetrahydrofuran-2-yl)methylamino)acetic acid), Nff (2-(furan-2-ylmethylamino)acetic acid), Nmb (2-(2-methylbutylamino)acetic acid), Nrh (2-(R)-(2-hydroxypropylamino)acetic acid), Nsh (2-(S)-(2-hydroxypropylamino) acetic acid), N3p (2-(2-(2-(2-methoxyethoxy)ethoxy) ethylamino)acetic acid, Nbr ((2-(R)-sec-butylamino)acetic acid), and Nbs ((2-(S)-sec-butylamino)acetic acid). The following abbreviations are used to refer to chemical compounds: DMF (N, N'-dimethylformamide), DIEA (diisopropylethylamine), DIC (N, N'-diisopropylcarbodiimide), ACN (acetonitrile), DCM (methylene chloride), HFIP (hexafluoroisopropyl alcohol); Fmoc (9-fluorenylmethoxycarbonyl).

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The term "about" as used herein to modify a numerical value indicates a defined range around that value. If "X" were the value, "about X" would indicate a value from 0.9X to 1.1X, and more preferably, a value from 0.95X to 1.05X. Any reference to "about X" specifically indicates at least the values X, 0.95X, 0.96X, 0.97X, 0.98X, 0.99X, 1.01X, 1.02X, 1.03X, 1.04X, and 1.05X. Thus, "about X" is intended to teach and provide written description support for a claim limitation of, e.g., "0.98X."

The term "alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 30 carbons atoms, such as, but not limited to heptyl, octyl, nonyl, decyl, etc. Alkyl groups can be substituted or unsubstituted. Alkyl groups can be optionally substituted with one or more moieties selected from halo, hydroxy, amino, thiol, alkylamino, alkoxy, haloalkyl, carboxy, amido, nitro, oxo, thioxo, and cyano.

The term "alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be substituted or unsubstituted. Alkenyl groups can be optionally substituted with one or more moieties selected from halo, hydroxy, amino, thiol, alkylamino, alkoxy, haloalkyl, carboxy, amido, nitro, oxo, thioxo, and cyano.

The term "alkynyl" refers to either a straight chain or branched hydrocarbon having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can be substituted or unsubstituted. Alkynyl groups can be optionally substituted with one or more moieties selected from halo, hydroxy, amino, thiol, alkylamino, alkoxy, haloalkyl, carboxy, amido, nitro, oxo, thioxo, and cyano.

The term "alkylene" refers to a straight or branched, saturated, aliphatic radical having the number of carbon atoms indicated, and linking at least two other groups, i.e., a divalent hydrocarbon radical. The two moieties linked to the alkylene can be linked to the same atom or different atoms of the alkylene group. For instance, a straight chain alkylene can be the bivalent radical of —$(CH_2)_n$—, where n is any number of suitable carbon atoms. Representative alkylene groups include, but are not limited to, methylene, ethylene, propylene, isopropylene, butylene, isobutylene, sec-butylene, pentylene and hexylene. Alkylene groups can be substituted or unsubstituted. Alkylene groups can be optionally substituted with one or more moieties selected from halo, hydroxy, amino, thiol, alkylamino, alkoxy, haloalkyl, carboxy, amido, nitro, oxo, thioxo, and cyano.

The term "alkenylene" refers to an alkenyl group, as defined above, linking at least two other groups, i.e., a divalent hydrocarbon radical. The two moieties linked to the alkenylene can be linked to the same atom or different atoms of the alkenylene. Alkenylene groups include, but are not limited to, ethenylene, propenylene, isopropenylene, butenylene, isobutenylene, sec-butenylene, pentenylene and hexenylene. Alkenylene groups can be substituted or unsubstituted. Alkenylene groups can be optionally substituted with one or more moieties selected from halo, hydroxy, amino, thiol, alkylamino, alkoxy, haloalkyl, carboxy, amido, nitro, oxo, thioxo, and cyano.

The term "alkynylene" refers to an alkynyl group, as defined above, linking at least two other groups, i.e., a divalent hydrocarbon radical. The two moieties linked to the alkynylene can be linked to the same atom or different atoms of the alkynylene. Alkynylene groups include, but are not limited to, ethynylene, propynylene, isopropynylene, butynylene, sec-butynylene, pentynylene and hexynylene. Alkynylene groups can be substituted or unsubstituted. Alkynylene groups can be optionally substituted with one or more moieties selected from halo, hydroxy, amino, thiol, alkylamino, alkoxy, haloalkyl, carboxy, amido, nitro, oxo, thioxo, and cyano.

The term "halogen" or "halo" refers to fluorine, chlorine, bromine and iodine.

The term "amine" or "amino" refers to an —$N(R)_2$ group where the R groups can be hydrogen, alkyl, alkenyl, alkynyl, cycloalkyl, heterocycloalkyl, aryl, or heteroaryl, among others. The R groups can be the same or different. The amino groups can be primary (each R is hydrogen), secondary (one R is hydrogen) or tertiary (each R is other than hydrogen). The alkyl, alkenyl, alkynyl, cycloalkyl, heterocycloalkyl, aryl, or heteroaryl groups can be optionally substituted with one or more moieties selected from halo, hydroxy, amino, thiol, alkylamino, alkoxy, haloalkyl, carboxy, amido, nitro, oxo, thioxo, and cyano.

The term "hydroxyl" or "hydroxy" refers to an —OH group. The hydroxyl can be at any suitable carbon atom.

The term "thiol" refers to an —SH group. The thiol group can be at any suitable carbon atom.

The term "oxo" refers to a double bonded O group (=O, —C(O)—). The oxo group can be at any suitable carbon atom.

The term "thioxo" refers to a double bonded S group (=S). The thioxo group can be at any suitable carbon atom.

The term "nitro" refers to a —$NO_2$ group. The nitro group can be at any suitable carbon atom.

The term "carboxy" refers to a carboxylic acid group of the formula —C(O)OH or —$CO_2H$.

The term "cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to, cyclopropyl, cyclobutyl, cyclopentyl, and cyclohexyl. Cycloalkyl groups can be substituted or unsubstituted. Cycloalkyl groups can be optionally substituted with one or more moieties selected from alkyl, alkenyl, alkynyl, halo, hydroxy, amino, alkylamino, alkoxy, haloalkyl, carboxy, amido, thiol, nitro, oxo, thioxo, and cyano. For example, cycloalkyl groups can be substituted with $C_{1-6}$ alkyl or oxo (=O), among many others.

The term "heterocycloalkyl" refers to a saturated ring system having from 3 to 12 ring members and from 1 to 4 heteroatoms of N, O, or S. Additional heteroatoms can also be useful, including, but not limited to, B, Al, Si, and P. The heteroatoms can also be oxidized to form moieties including, but not limited to, —S(O)— and —$S(O)_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline. Heterocycloalkyl groups can be unsubstituted or substituted. Heterocycloalkyl groups can be optionally substituted with one or more moieties selected from alkyl, alkenyl, alkynyl, halo, hydroxy, amino, thiol, alkylamino, alkoxy, haloalkyl, carboxy, amido, nitro, oxo, thioxo, and cyano. For example, heterocycloalkyl groups can be substituted with $C_{1-6}$ alkyl or oxo (=O), among many others.

The heterocycloalkyl groups can be linked via any position on the ring. For example, aziridine can be 1- or 2-aziridine, azetidine can be 1- or 2-azetidine, pyrrolidine can be 1-, 2-, or 3-pyrrolidine, piperidine can be 1-, 2-, 3-, or 4-piperidine, pyrazolidine can be 1-, 2-, 3-, or 4-pyrazolidine, imidazolidine can be 1-, 2-, 3-, or 4-imidazolidine, piperazine can be 1-, 2-, 3-, or 4-piperazine, tetrahydrofuran can be 1- or 2-tetrahydrofuran, oxazolidine can be 2-, 3-, 4-, or 5-oxazolidine, isoxazolidine can be 2-, 3-, 4-, or 5-isoxazolidine, thiazolidine can be 2-, 3-, 4-, or 5-thiazolidine, isothiazolidine can be 2-, 3-, 4-, or 5-isothiazolidine, and morpholine can be 2-, 3-, or 4-morpholine.

When heterocycloalkyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxazolidine, thiazolidine, isothiazolidine, morpholine, thiomorpholine, dioxane, and dithiane. Heterocycloalkyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

The term "aryl" refers to an aromatic ring system having any suitable number of ring atoms and any suitable number of rings. Aryl groups can include any suitable number of ring atoms, such as, 6, 7, 8, 9, 10, 11, 12, 13, 14, 15, or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted. Aryl groups can be optionally substituted with one or more moieties selected from alkyl, alkenyl, alkynyl, halo, hydroxy, amino, thiol, alkylamino, alkoxy, haloalkyl, carboxy, amido, nitro, oxo, thioxo, and cyano.

The term "heteroaryl" refers to a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si, and P. The heteroatoms can also be oxidized to form moieties including, but not limited to, —S(O)— and —S(O)$_2$—. Heteroaryl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted. Heteroaryl groups can be optionally substituted with one or more moieties selected from alkyl, alkenyl, alkynyl, halo, hydroxy, amino, thiol, alkylamino, alkoxy, haloalkyl, carboxy, amido, nitro, oxo, thioxo, and cyano.

The heteroaryl groups can be linked via any position on the ring. For example, pyrrole includes 1-, 2-, and 3-pyrrole, pyridine includes 2-, 3-, and 4-pyridine, imidazole includes 1-, 2-, 4-, and 5-imidazole, pyrazole includes 1-, 3-, 4-, and 5-pyrazole, triazole includes 1-, 4-, and 5-triazole, tetrazole includes 1- and 5-tetrazole, pyrimidine includes 2-, 4-, 5-, and 6-pyrimidine, pyridazine includes 3- and 4-pyridazine, 1,2,3-triazine includes 4- and 5-triazine, 1,2,4-triazine includes 3-, 5-, and 6-triazine, 1,3,5-triazine includes 2-triazine, thiophene includes 2- and 3-thiophene, furan includes 2- and 3-furan, thiazole includes 2-, 4-, and 5-thiazole, isothiazole includes 3-, 4-, and 5-isothiazole, oxazole includes 2-, 4-, and 5-oxazole, isoxazole includes 3-, 4-, and 5-isoxazole, indole includes 1-, 2-, and 3-indole, isoindole includes 1- and 2-isoindole, quinoline includes 2-, 3-, and 4-quinoline, isoquinoline includes 1-, 3-, and 4-isoquinoline, quinazoline includes 2- and 4-quinoazoline, cinnoline includes 3- and 4-cinnoline, benzothiophene includes 2- and 3-benzothiophene, and benzofuran includes 2- and 3-benzofuran.

Some heteroaryl groups include those having from 5 to 10 ring members and from 1 to 3 ring atoms including N, O, or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring atoms including N, O, or S, such as pyrrole, pyridine, imidazole, pyrazole, pyrazine, pyrimidine, pyridazine, thiophene, furan, thiazole, isothiazole, oxazole, and isoxazole.

The term "(cycloalkyl)alkyl" refers to a radical having an alkyl component and a cycloalkyl component, where the alkyl component links the cycloalkyl component to the point of attachment. The alkyl component is as defined above, except that the alkyl component is at least divalent, an alkylene, to link to the cycloalkyl component and to the point of attachment. The alkyl component can include any number of carbons, such as $C_{1-6}$, $C_{1-2}$, $C_{1-3}$, $C_{1-4}$, $C_{1-5}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The cycloalkyl component is as defined within. Exemplary (cycloalkyl)alkyl groups include, but are not limited to, methyl-cyclopropyl, methyl-cyclobutyl, methyl-cyclopentyl, and methyl-cyclohexyl.

The term "(heterocycloalkyl)alkyl" refers to a radical having an alkyl component and a heterocycloalkyl component, where the alkyl component links the heterocycloalkyl component to the point of attachment. The alkyl component is as defined above, except that the alkyl component is at least divalent, an alkylene, to link to the heterocycloalkyl component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The heterocycloalkyl component is as defined above. (Heterocycloalkyl)alkyl groups can be substituted or unsubstituted.

The term "arylalkyl" refers to a radical having an alkyl component and an aryl component, where the alkyl component links the aryl component to the point of attachment. The alkyl component is as defined above, except that the alkyl component is at least divalent, an alkylene, to link to the aryl component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The aryl component is as defined above. Examples of arylalkyl groups include, but are not limited to, benzyl and ethyl-benzene. Arylalkyl groups can be substituted or unsubstituted.

The term "heteroarylalkyl" refers to a radical having an alkyl component and a heteroaryl component, where the alkyl component links the heteroaryl component to the point of attachment. The alkyl component is as defined above, except that the alkyl component is at least divalent, an alkylene, to link to the heteroaryl component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The heteroaryl component is as defined within. Heteroarylalkyl groups can be substituted or unsubstituted.

The term "carboxyalkyl" refers to a carboxy group linked to an alkyl, as described above, and generally having the formula $—C_{1-8}$ alkyl-C(O)OH. Any suitable alkyl chain is useful. Carboxyalkyl groups can be optionally substituted with one or more moieties selected from halo, hydroxy, amino, thiol, alkylamino, alkoxy, haloalkyl, carboxy, amido, nitro, oxo, thioxo, and cyano.

The term "acyl" refers to an alkyl that contains an oxo substituted carbon at the point of attachment (—C(O)—$C_{1-8}$ alkyl). Any suitable alkyl chain can be used. Acyl groups can be optionally substituted with one or more moieties selected from halo, hydroxy, amino, thiol, alkylamino, alkoxy, haloalkyl, carboxy, amido, nitro, oxo, thioxo, and cyano.

The term "hydroxyalkyl" refers to an alkyl group, as defined above, where at least one of the hydrogen atoms is replaced with a hydroxy group. As for the alkyl group, hydroxyalkyl groups can have any suitable number of carbon atoms, such as $C_{1-6}$. Exemplary hydroxyalkyl groups include, but are not limited to, hydroxy-methyl, hydroxy-ethyl (where the hydroxy is in the 1- or 2-position), hydroxypropyl (where the hydroxy is in the 1-, 2- or 3-position), hydroxybutyl (where the hydroxy is in the 1-, 2-, 3- or 4-position), hydroxypentyl (where the hydroxy is in the 1-, 2-, 3-, 4- or 5-position), hydroxyhexyl (where the hydroxy is in the 1-, 2-, 3-, 4-, 5- or 6-position), 1,2-dihydroxyethyl, and the like. Hydroxyalkyl groups can be optionally substituted with one or more moieties selected from halo, thiol, amino, alkylamino, alkoxy, haloalkyl, carboxy, amido, nitro, oxo, thioxo, and cyano. One of skill in the art will appreciate that other hydroxyalkyl groups are useful in the present invention.

The term "alkoxy" refers to an alkyl group having at least one bridging oxygen atom. The bridging oxygen atom can be anywhere within the alkyl chain (alkyl-O-alkyl) or the bridging oxygen atom can connect the alkyl group to the point of attachment (alkyl-O—). In some embodiments, the bridging oxygen atom is not present as a terminal hydroxy group (i.e., —OH). In some instances, the alkoxy contains 1, 2, 3, 4, or 5 bridging oxygen atoms. As for alkyl groups, alkoxy groups can have any suitable number of carbon atoms, such as $C_{1-2}$, $C_{1-4}$, and $C_{1-6}$. Alkoxy groups include, for example, methoxy, ethoxy, propoxy, iso-propoxy, methyloxy-ethyloxy-ethyl ($C_1$—O—$C_2$—O—$C_2$—), etc. One example of an alkoxy group is polyethylene glycol (PEG) wherein the polyethylene glycol chain can include between 2 to 20 ethylene glycol monomers. Alkoxy groups can be optionally substituted with one or more moieties selected from halo, hydroxy, amino, thiol, alkylamino, haloalkyl, carboxy, amido, nitro, oxo, thioxo, and cyano. Alkoxy groups can be substituted or unsubstituted.

The term "alkylamino" refers to an alkyl group as defined within, having one or more amino groups. The amino groups can be primary, secondary or tertiary. Alkylamino groups useful in the present invention include, but are not limited to, ethyl amine, propyl amine, isopropyl amine, ethylene diamine, and ethanolamine. The amino group can link the alkylamino to the point of attachment with the rest of the compound, be at any position of the alkyl group, or link together at least two carbon atoms of the alkyl group. Alkylamino groups can be optionally substituted with one or more moieties selected from halo, hydroxy, thiol, alkylamino, alkoxy, haloalkyl, carboxy, amido, nitro, oxo, thioxo, and cyano. One of skill in the art will appreciate that other alkylaminos are useful in the present invention.

The term "alkylthio" refers to an alkyl group as defined within, having one or more thiol groups. Alkylthio groups useful in the present invention include, but are not limited to, ethyl thiol, propyl thiol, and isopropyl thiol. The thiol group can link the alkylthio to the point of attachment with the rest of the compound, be at any position of the alkyl group, or link together at least two carbon atoms of the alkyl group. Alkylthio groups can be optionally substituted with one or more moieties selected from halo, hydroxy, amino, alkylamino, alkoxy, haloalkyl, carboxy, amido, nitro, oxo, thioxo, and cyano. One of skill in the art will appreciate that other alkylthio are useful in the present invention.

The term "oxyethyl" refers to a divalent radical having the formula —OCH$_2$CH$_2$—.

The term "wavy line" signifies the point of attachment of a substituent to the remainder of a molecule. When the wavy line is not depicted as being specifically appended to a specific ring atom, the point of attachment can be to any suitable atom of the substituent. For example, the wavy line in the following structure:

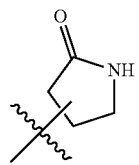

is intended to include, as the point of attachment, any of the substitutable atoms.

The term "regenerative medicine" refers to a branch of medicine that deals with the process of replacing, engineering, or regenerating human cells, tissues, or organs to restore or establish normal function. In some embodiments, regenerative medicine includes growing tissues and organs in the laboratory and safely implanting them when the body cannot heal itself.

The term "bioengineered tissue" refers to one or more synthetically created cells, tissues, or organs created for the purposes of regenerative medicine. In some embodiments, bioengineered tissue refers to cells, tissues, or organs that were developed in the laboratory. In some embodiments, bioengineered tissues refers to laboratory derived heart, liver, lung, kidney, pancreas, intestine, thymus, cornea, stem cells (e.g., human pluripotent stem cells, hematopoietic stem cells), lymphocytes, granulocytes, immune system cells, bone cells, primary cells, organoids, embryonic cells, genitourinary cells (e.g., sperm cells, oocytes, corpus cavernosum cells (e.g., smooth muscle corpus cavernosum cells, epithelial corpus cavernosum cells), urinary bladder cells, urethral cells, ureter cells, kidney cells, testicular cells), blood platelets, nerve cells, or a combination thereof.

The term "cryoprotectant solution" refers to a solution used to reduce or prevent freezing damage caused by ice crystal formation. In some embodiments, the cryoprotectant solution comprises one or more peptoid polymers and/or salts thereof described herein. In other embodiments, the cryoprotectant solution comprises one or more peptoid polymers and/or salts thereof described herein and one or more peptoid-peptide hybrids and/or salts thereof described herein. In some embodiments, the cryoprotectant solution protects a biological sample from freezing damage. In some embodiments, the cryoprotectant solution protects a non-biological sample from ice crystal formation. In some embodiments, the cryoprotectant solution preserves a biological sample for an amount of time longer than if the biological sample were not exposed to reduced temperatures.

The terms "vitrify" and "vitrification" mean the transformation of a substance into a glass (i.e., a non-crystalline amorphous solid). In the context of water, vitrification refers to the transformation of water into a glass without the formation of ice crystals, as opposed to ordinary freezing, which results in ice crystal formation. Vitrification is often achieved through very rapid cooling and/or the introduction of agents that suppress ice crystal formation. On the other hand, "devitrify" and "devitrification" refer to the process of crystallization in a previously crystal-free (amorphous) glass. In the context of water ice, devitrification can mean the formation of ice crystals as the previously non-crystalline amorphous solid undergoes melting.

The term "peptoid monomer" means a molecule, comprising side chains $R^1$ and $R^2$, according to formula (I):

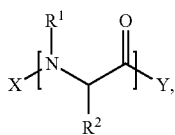

(I)

and includes stereoisomers and tautomers thereof. In some embodiments, $R^1$ is selected from the group consisting of H, hydroxyl, optionally substituted $C_{1-18}$ alkyl, optionally substituted $C_{2-18}$ alkenyl, optionally substituted $C_{2-18}$ alkynyl, optionally substituted $C_{1-18}$ hydroxyalkyl, optionally substituted alkoxy, optionally substituted $C_{1-18}$ alkylamino, optionally substituted $C_{1-18}$ alkylthio, optionally substituted carboxyalkyl, $C_{3-10}$ cycloalkyl, heterocycloalkyl, aryl, heteroaryl, ($C_{3-10}$ cycloalkyl)alkyl, (heterocycloalkyl)alkyl, arylalkyl, and heteroarylalkyl, wherein any of the cycloalkyl, heterocycloalkyl, aryl, and heteroaryl groups is optionally substituted with one or more $R^3$ groups. In particular embodiments, $R^3$ is selected from the group consisting of halogen, oxo, thioxo, —OH, —SH, sulfonamide, amino, $C_{1-8}$ alkyl, $C_{1-8}$ hydroxyalkyl, $C_{1-8}$ alkylamino, and $C_{1-8}$ alkylthio. Furthermore, $R^1$ can comprise the side chain of any of the amino acids alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), or tyrosine (Tyr).

$R^1$ and $R^2$ are independently selected. In some embodiments, $R^2$ is H. In other embodiments, $R^2$ is selected from the group consisting of hydroxyl, optionally substituted $C_{1-18}$ alkyl, optionally substituted $C_{2-18}$ alkenyl, optionally substituted $C_{2-18}$ alkynyl, optionally substituted $C_{1-18}$ hydroxyalkyl, optionally substituted alkoxy, optionally substituted $C_{1-18}$ alkylamino, optionally substituted $C_{1-18}$ alkylthio, optionally substituted carboxyalkyl, $C_{3-10}$ cycloalkyl, heterocycloalkyl, aryl, heteroaryl, ($C_{3-10}$ cycloalkyl)alkyl, (heterocycloalkyl)alkyl, arylalkyl, and heteroarylalkyl, wherein any of the cycloalkyl, heterocycloalkyl, aryl, and heteroaryl groups is optionally substituted with one or more $R^3$ groups. In particular embodiments, $R^3$ is selected from the group consisting of halogen, oxo, thioxo, —OH, —SH, sulfonamide, amino, $C_{1-8}$ alkyl, $C_{1-8}$ hydroxyalkyl, $C_{1-8}$ alkylamino, and $C_{1-8}$ alkylthio. Furthermore, $R^2$ can comprise the side chain of any of the amino acids alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), or tyrosine (Tyr).

In some embodiments, R1 and/or R2 comprises the structure:

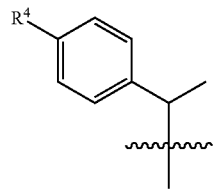

wherein $R^4$ is selected from the group consisting of H, $C_{1-8}$ alkyl, hydroxyl, sulfonamide, thiol, nitro, amine, oxo, and thioxo.

In some embodiments, the peptoid monomer is selected from the group of peptoid monomers set forth in Table 1. A person of skill in the art will recognize that the bounds of this invention are not limited to the monomers listed in Table 1, and that any useful N-substituted substituent can be used as an N-substituted peptoid monomer.

X and Y are independently selected from the group consisting of H, optionally substituted $C_{1-8}$ alkyl, optionally substituted $C_{1-8}$ acyl, optionally substituted $C_{1-8}$ alkylamino, —OH, —SH, —NH$_2$, carboxy, optionally substituted $C_{1-8}$ hydroxyalkyl, optionally substituted $C_{1-8}$ alkylamino, optionally substituted $C_{2-8}$ alkylthio, optionally substituted $C_{1-8}$ carboxyalkyl, and halogen. In some embodiments, X is an acetyl group. In some embodiments, Y is carboxy. Alternatively, X and Y are taken together to form a covalent bond. When the peptoid monomer is present as part of a polymer, X and/or Y can represent covalent bonds to other peptoid monomers.

Whenever any peptoid monomer herein does not indicate stereochemistry, any stereoisomer may be used. In some embodiments, a mixture of the two stereoisomers are chosen. In embodiments comprising a mixture of stereoisomers, the ratio of R to S stereoisomers of the monomer in the peptoid polymer can range from about 95:5 to about 90:10, from about 90:10 to about 85:15, from about 85:15 to about 80:20, from about 80:20 to about 75:25, from about 75:25 to about 70:30, from about 70:30 to about 65:35, from about 65:35 to about 60:40, from about 60:40 to about 55:45, from about 55:45 to about 50:50, from about 50:50 to about 45:55, from about 45:55 to about 40:60, from about 40:60 to about 35:65, from about 35:65 to about 30:70, from about 30:70 to about 25:75, from about 25:75 to about 20:80, from about 20:80 to about 15:85, from about 15:85 to about 10:90, or from about 10:90 to about 5:95. In some embodiments, only the R stereoisomer of the monomer is chosen. In some embodiments, only the S stereoisomer of the monomer is chosen.

Whenever a particular stereochemistry is shown with a wedge or a dashed line, the monomer is substantially free of other stereoisomers. In some embodiments, substantially free means at least 70% pure. In some embodiments, substantially free means at least 80% pure. In some embodiments, substantially free means at least 90% pure. In some embodiments, substantially free means at least 95% pure. In some embodiments, substantially free means at least 99% pure. In some embodiments, substantially free means at least 99.9% pure.

In some embodiments, one or more $R^1$ and/or $R^2$ side chains have a structure according to $R^{1a}$:

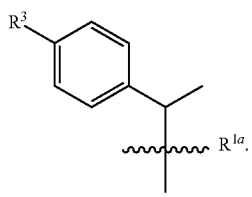

In some embodiments, each $R^{1a}$ group is independently selected from

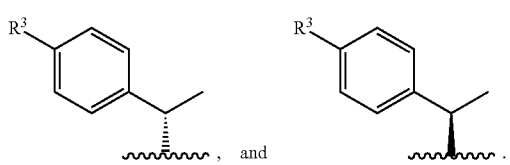

In some embodiments, a mixture of the two stereoisomers are chosen. In some embodiments, only the R stereoisomer of the monomer is chosen. In some embodiments, only the S stereoisomer of this monomer is chosen.

In some embodiments, one or more $R^1$ and/or $R^2$ side chains have a structure according to $R^{1b}$:

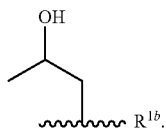

In some embodiments, each $R^{1b}$ group is independently selected from

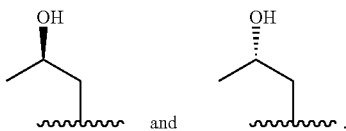

In some embodiments, a mixture of the two stereoisomers are chosen. In some embodiments, only the R stereoisomer of the monomer is chosen. In some embodiments, only the S stereoisomer of this monomer is chosen.

In some embodiments, one or more $R^1$ and/or $R^2$ side chains have a structure according to $R^{1c}$:

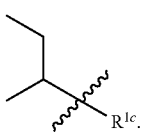

In some embodiments, each $R^{1c}$ group is independently selected from

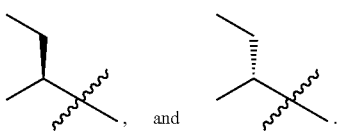

In some embodiments, a mixture of the two stereoisomers are chosen. In some embodiments, only the R stereoisomer of the monomer is chosen. In some embodiments, only the S stereoisomer of this monomer is chosen.

In some embodiments, one or more $R^1$ and/or $R^2$ side chains have a structure according to $R^{1d}$:

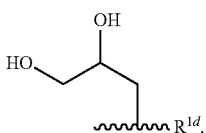

In some embodiments, each $R^{1d}$ group is independently selected from

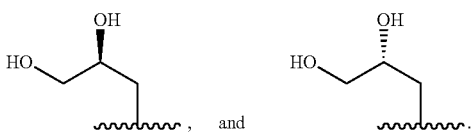 [SMILES: *C[C@H](O)CO ; *C[C@@H](O)CO]

In some embodiments, a mixture of the two stereoisomers are chosen. In some embodiments, only the R stereoisomer of the monomer is chosen. In some embodiments, only the S stereoisomer of this monomer is chosen.

In some embodiments, one or more $R^1$ and/or $R^2$ side chains have a structure according to $R^{1e}$:

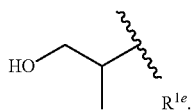

In some embodiments, each $R^{1e}$ group is independently selected from

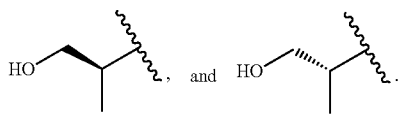

In some embodiments, a mixture of the two stereoisomers are chosen. In some embodiments, only the R stereoisomer of the monomer is chosen. In some embodiments, only the S stereoisomer of this monomer is chosen.

The terms "polar peptoid monomer" and "peptoid monomer having a polar side chain" are used interchangeably to refer to peptoid monomers in which the substituent "$R^1$" is a polar side chain, or both $R^1$ and the substituent "$R^2$" are polar side chains. Commonly, a polar side chain comprises a hydroxyl group and/or an atom (e.g., sulfur, nitrogen, oxygen) that can participate in hydrogen bonding. In some instances, a polar side chain includes atoms or groups that are more hydrophobic than polar in nature (e.g., aromatic rings). In these instances, the side chain also includes atoms or groups such that the entire side chain is more polar than hydrophobic. As a non-limiting example, a polar side chain can contain an aromatic ring to which one or more hydroxyl groups are attached.

Examples of polar peptoid monomers include, but are not limited to,

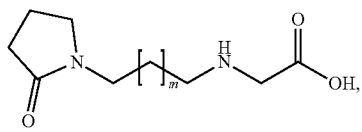

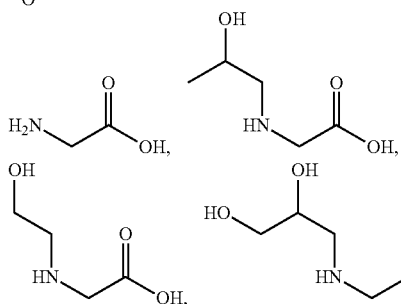

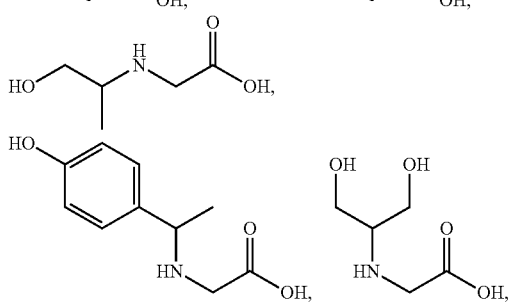

-continued

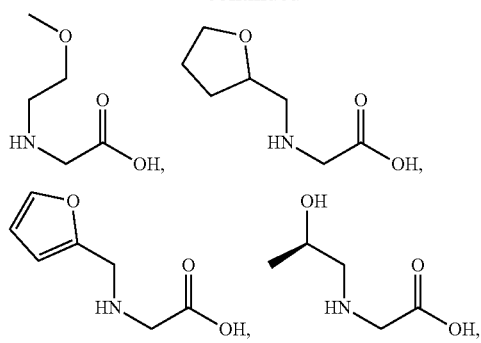

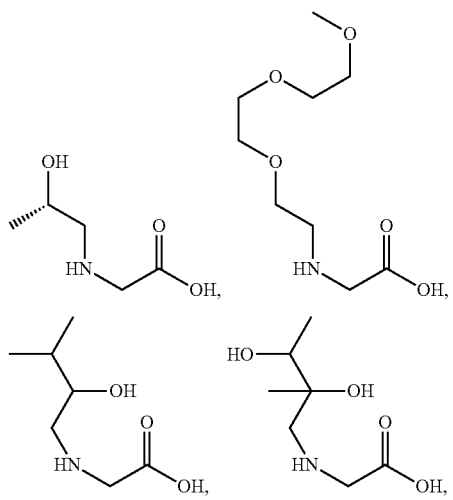

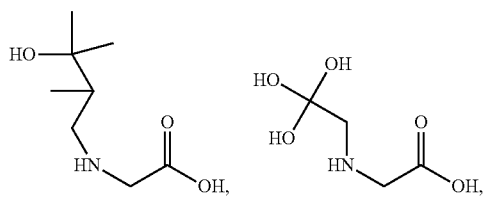

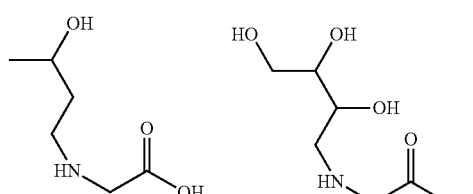

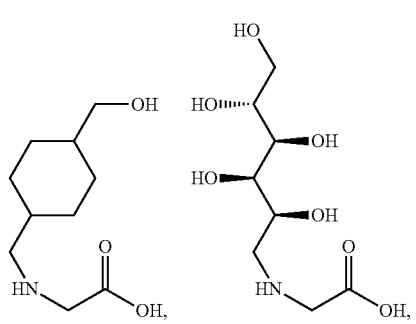

-continued
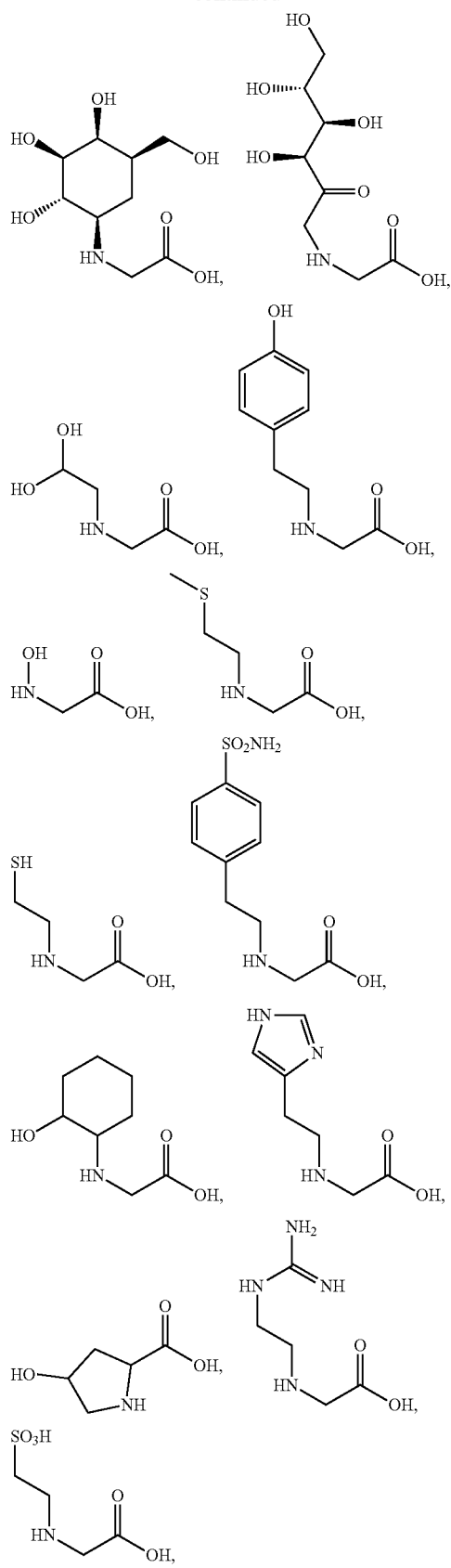
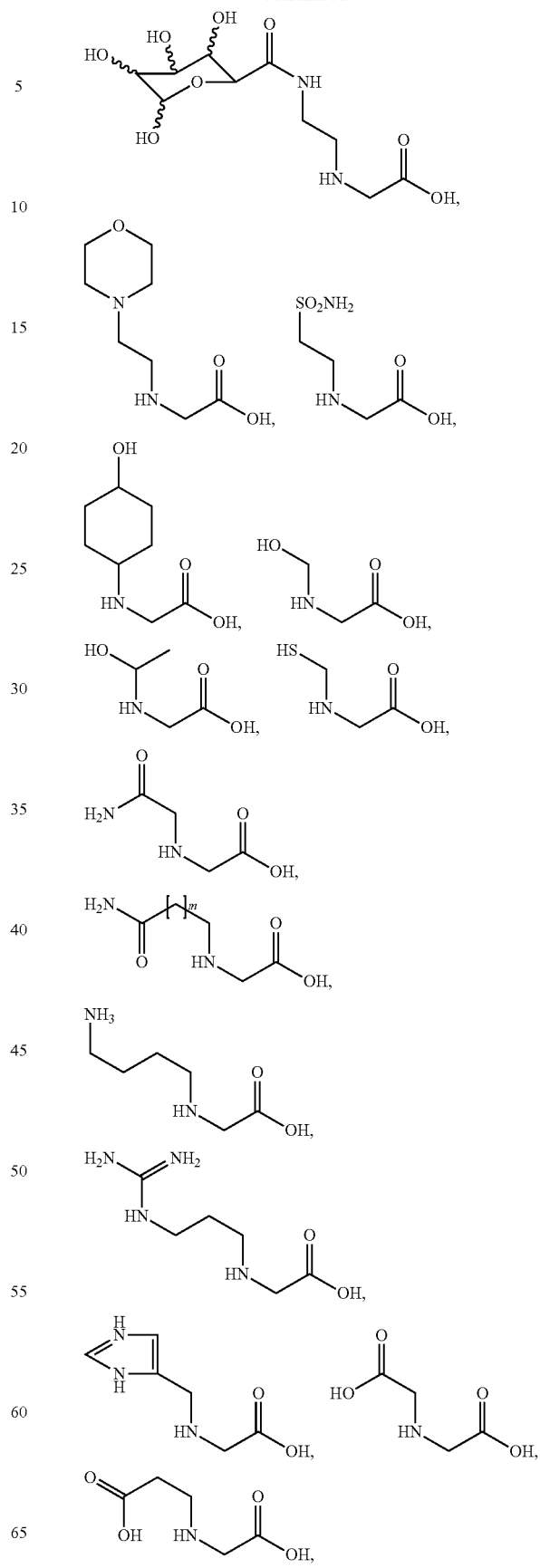

-continued

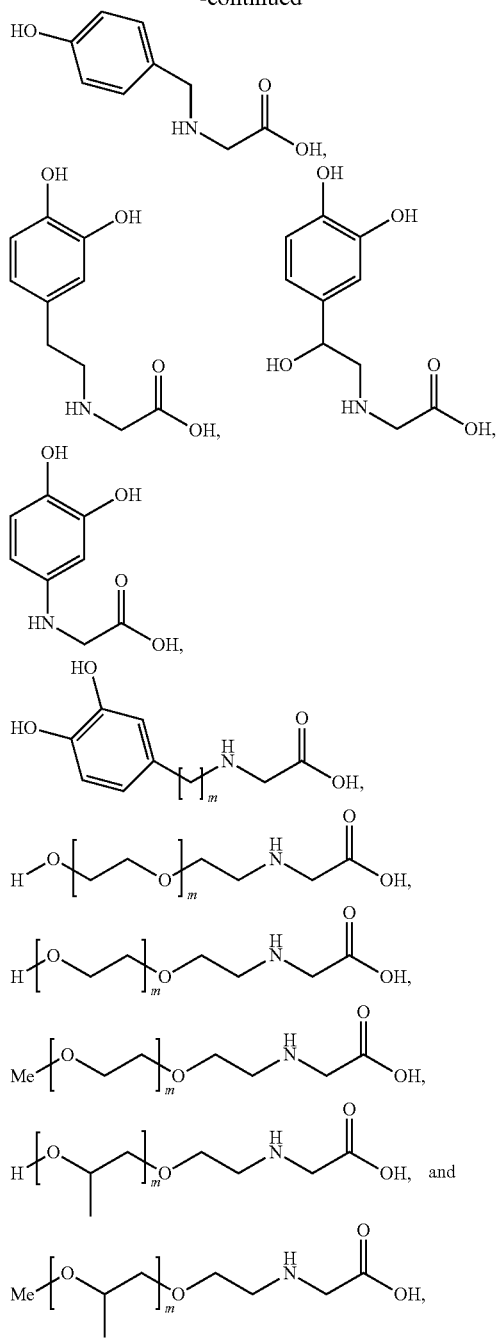

wherein the subscript m is the number of repeat units and is between 1 and 10.

In some embodiments, a peptoid polymer or salt thereof of the present invention comprises one or more polar peptoid monomers selected from the group consisting of Nop, Nhp, Nhe, Ndp, Nyp, Nep, Ndh, and a combination thereof.

The terms "hydrophobic peptoid monomer" and "peptoid monomer having a hydrophobic side chain" are used interchangeably to refer to peptoid monomers in which the substituent "$R^1$" is a hydrophobic side chain (e.g., not polar), or both $R^1$ and the substituent "$R^2$" are hydrophobic side chains. Commonly, a hydrophobic side chain comprises an unsubstituted alkyl, unsubstituted cycloalkyl, or an unsubstituted aromatic group.

Examples of hydrophobic peptoid monomers include, but are not limited to

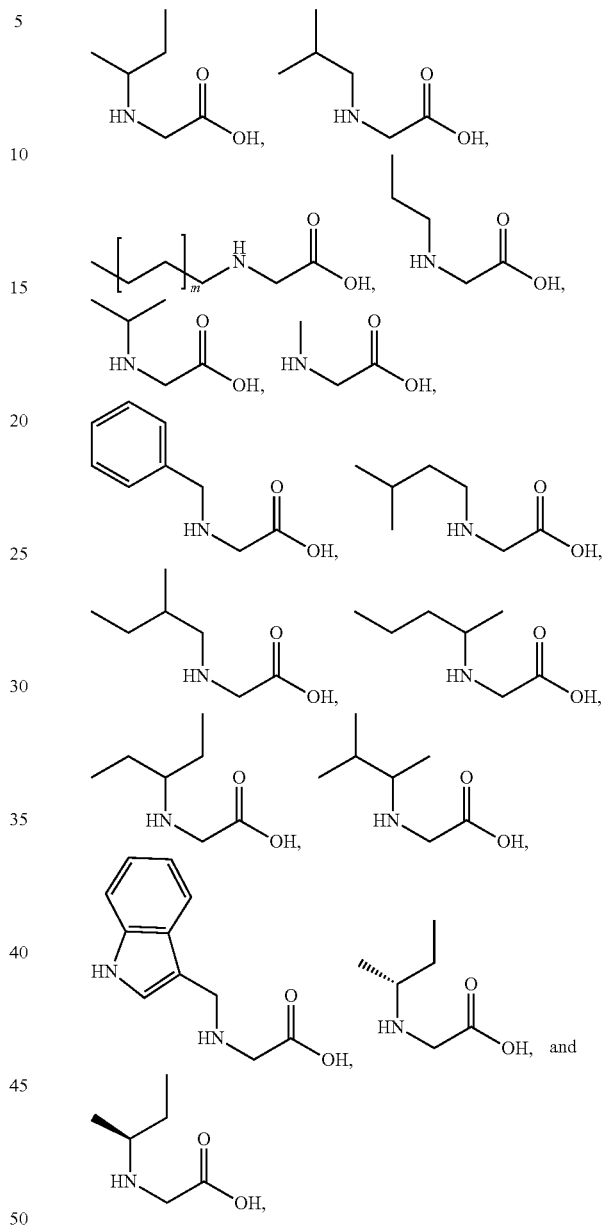

wherein the subscript m is the number of repeat units and is between 1 and 10.

In some embodiments, a peptoid polymer or salt thereof of the present invention comprises one or more hydrophobic peptoid monomers selected from the group consisting of Nsb, Nib, Nbu, Npr, Nip, Nme, and a combination thereof.

The term "peptoid polymer" or "peptoid" refers to a polyamide of between about 2 and 1,000 (e.g., between about 2 and 1,000, 2 and 950, 2 and 900, 2 and 850, 2 and 800, 2 and 750, 2 and 700, 2 and 650, 2 and 600, 2 and 550, 2 and 500, 2 and 450, 2 and 400, 2 and 350, 2 and 300, 2 and 250, 2 and 200, 2 and 150, 2 and 100, 2 and 90, 2 and 80, 2 and 70, 2 and 60, 2 and 50, 2 and 40, 2 and 30, 2 and 20, 2 and 10, 2 and 9, 2 and 8, 2 and 7, 2 and 6, 2 and 5, 2 and 4, or 2 and 3) peptoid monomers. In particular instances, a peptoid is a synthetic analog of a peptide wherein the side chains that would otherwise be attached to the α-carbon atoms are instead attached to the amide nitrogen atoms. Peptoids are synthetic polymers with controlled sequences and lengths that can be made by automated solid-phase organic synthesis to include a wide variety of side-chains having different chemical functions. The term includes free amine forms as well as salt forms.

The term "peptoid-peptide hybrid" refers to an oligomer that is composed of both peptoid monomer units and alpha amino acids (i.e., peptide units). The term includes free amine forms as well as salt forms.

The terms "polypeptide," "peptide," and "protein" are used interchangeably herein to refer to a polymer of amino acid residues, or an assembly of multiple polymers of amino acid residues.

The term "amino acid" includes but is not limited to naturally-occurring α-amino acids and their stereoisomers. "Stereoisomers" of amino acids refers to mirror image isomers of the amino acids, such as L-amino acids or D-amino acids. For example, a stereoisomer of a naturally-occurring amino acid refers to the mirror image isomer of the naturally-occurring amino acid (i.e., the D-amino acid).

Naturally-occurring amino acids are those encoded by the genetic code, as well as those amino acids that are later modified (e.g., hydroxyproline, γ-carboxyglutamate, and O-phosphoserine). Naturally-occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of a naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Amino acids may be referred to herein by either their commonly known three letter symbols or by the one-letter symbols recommended by the IUPAC-IUB Biochemical Nomenclature Commission. For example, an L-amino acid may be represented herein by its commonly known three letter symbol (e.g., Arg for L-arginine) or by an upper-case one-letter amino acid symbol (e.g., R for L-arginine). A D-amino acid may be represented herein by its commonly known three letter symbol (e.g., D-Arg for D-arginine) or by a lower-case one-letter amino acid symbol (e.g., r for D-arginine).

III. Detailed Description of the Embodiments

A. Peptoid Polymers

In one aspect, the present invention provides a peptoid polymer or a salt thereof comprising subunits comprising one or more first hydrophobic peptoid monomers H and one or more first polar peptoid monomers P arranged such that the peptoid polymer has the sequence $[H_aP_b]_n$ or $[P_bH_a]_n$, wherein the subscript a represents the number of consecutive first hydrophobic peptoid monomers within a subunit, the subscript b represents the number of consecutive first polar peptoid monomers within a subunit, and the subscript n represents the number of subunits within the peptoid polymer. In some embodiments, a is between 1 and 10 (e.g., a is 1, 2, 3, 4, 5, 6, 7, 8, 9, or 10). In other embodiments, b is between 1 and 10 (e.g., b is 1, 2, 3, 4, 5, 6, 7, 8, 9, or 10). In some instances, a is between 1 and 5. In other instances, b is between 1 and 5. In particular instances, a is between 1 and 3 and b is between 1 and 3.

In some embodiments, the subunits further comprise a second hydrophobic peptoid monomer and/or a second polar peptoid monomer such that the peptoid polymer has the sequence $[H_aP_bH_cP_d]_n$ or $[P_bH_aP_dH_c]_n$, wherein the subscript c represents the number of consecutive second hydrophobic peptoid monomers within a subunit and the subscript d represents the number of consecutive second polar peptoid monomers within a subunit. In some embodiments, c is between 0 and 10 (e.g., c is 0, 1, 2, 3, 4, 5, 6, 7, 8, 9, or 10). In other embodiments, d is between 0 and 10 (e.g., d is 0, 1, 2, 3, 4, 5, 6, 7, 8, 9, or 10). In particular embodiments, both c and d are not 0. In some instances, c is between 0 and 5. In other instances, d is between 0 and 5.

As non-limiting examples, a subunit of a peptoid polymer of the present invention can comprise the sequence HP, PH, HHPP, PPHH, HPHP, PHPH, HPPH, PHHP, HHP, PHH, HPP, PPH, HPPP, PPPH, HHPPHH, PPHHPP, HHHPPP, PPPHHH, HHHH, PHHH, HHHPPPHHH, or PPPHHHPPP. When a is 1 and b is 1, the subunit can comprise the sequence HP or PH. When a is 2 and b is 2, the subunit can comprise the sequence HHPP or PPHH. When a is 1 and b is 2, the subunit can comprise the sequence HPP or PPH. When a is 2 and b is 1, the subunit can comprise the sequence HHP or PHH. When a is 1 and b is 3, the subunit can comprise the sequence HPPP or PPPH. When a is 3 and b is 1, the subunit can comprise the sequence HHHP or PHHH. When a is 3 and b is 3, the subunit can comprise the sequence HHHPPP or PPPHHH.

As further non-limiting examples, when a, b, c, and d are 1, the subunit can comprise the sequence HPHP or PHPH, although these sequences can also be represented by the formulas $[H_1P_1]_2$ and $[P_1H_1]_2$, respectively, where n is 2. When a is 1, b is 2, c is 1, and d is 0, the subunit can comprise the sequence HPPH. When a is 2, b is 1, c is 0, and d is 1 the subunit can comprise the sequence PHHP (i.e., $P_1H_2P_1H_0$). When a, b, and c are 2 and d is 0, the subunit can comprise the sequence HHPPHH. When a, b, and d are 2 and c is 0, the subunit can comprise the sequence PPHHPP (i.e., $P_2H_2P_2H_0$). When a, b, and c are 3 and d is 0, the subunit can comprise the sequence HHHPPPHHH. When a, b, and d are 3 and c is 0, the subunit can comprise the sequence PPPHHHPPP (i.e., $P_3H_3P_3H_0$).

When more than one hydrophobic peptoid monomer is present in a peptoid polymer or salt thereof, all of the hydrophobic peptoid monomers can be the same, they can all be different, or a combination thereof. Similarly, when more than one polar peptoid monomer is present in a peptoid polymer or salt thereof, all of the polar peptoid monomers can be the same, they can all be different, or a combination thereof.

In some embodiments, the peptoid polymer or salt thereof further comprises substituents X and Y such that the peptoid polymer has the sequence $X—[H_aP_b]_n—Y$, $X—[P_bH_a]_n—Y$, $X—[H_aP_bH_cP_d]_n—Y$, or $X—[P_bH_aP_dH_c]_n—Y$. In some embodiments, X and Y are independently selected from the group consisting of H, optionally substituted $C_{1-8}$ alkyl, optionally substituted $C_{1-8}$ acyl, optionally substituted $C_{1-8}$ alkylamino, —OH, —SH, —NH$_2$, acetyl, carboxy, optionally substituted $C_{1-8}$ hydroxyalkyl, optionally substituted $C_{1-8}$ alkylamino, optionally substituted $C_{2-8}$ alkylthio, optionally substituted $C_{1-8}$ carboxyalkyl, and halogen. Alternatively, X and Y are taken together to form a covalent bond. The formation of a covalent bond between X and Y results in a circularized form of the peptoid polymer.

In some embodiments, X and Y are H, optionally substituted $C_{1-8}$ alkylamino, —OH, —SH, acetyl, carboxy, optionally substituted $C_{1-8}$ hydroxyalkyl, optionally substituted $C_{1-8}$ alkylamino, optionally substituted $C_{2-8}$ alkylthio, optionally substituted $C_{1-8}$ carboxyalkyl, or halogen. In other embodiments, X or Y is a secondary amine or a tertiary amine.

In some embodiments, the peptoid polymer or salt thereof further comprises a sequence Z that comprises one or more hydrophobic peptoid monomers and/or one or more polar peptoid monomers. Z can be located before the first subunit, after the last subunit, and/or between one or more subunits. In some instances, Z comprises one or more hydrophobic peptoid monomers. In other instances, Z comprises one or more polar peptoid monomers. In particular instances, Z comprises one or more hydrophobic peptoid monomers and one or more polar peptoid monomers. Z can comprise a number of contiguous hydrophobic peptoid monomers, followed by a number of contiguous polar peptoid monomers, or vice versa. Alternatively, Z can comprise a number of contiguous hydrophobic peptoid monomers followed by a number of contiguous polar peptoid monomers, followed by additional hydrophobic peptoid monomers, and so on. When more than one hydrophobic peptoid monomer is present in sequence Z, all of the hydrophobic peptoid monomers can be of the same type, they can each be different, or a combination thereof. Similarly, when more than one polar peptoid monomer is present in sequence Z, all of the polar peptoid monomers can be of the same type, they can each be different, or a combination thereof. In some embodiments, a peptoid polymer or salt thereof of the present invention comprises more than 1 (e.g., 2, 3, 4, 5, or more) instances of a sequence Z. In such cases, all instances of Z can be the same, they can each be different, or a combination thereof. In particular embodiments, a sequence Z comprises 1, 2, 3, 4, or more hydrophobic peptoid monomers. In yet other embodiments, a sequence Z comprises 1, 2, 3, 4, or more polar peptoid monomers.

In some embodiments, n is between 2 and 50 (e.g., n is 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50). In some instances, n is between 2 and 10 (e.g., n is 2, 3, 4, 5, 6, 7, 8, 9, or 10). In some embodiments, n is between 3 and 25. In some embodiments, n is between 5 and 25. In some embodiments, n is between 8 and 50. In some embodiments, n is between 8 and 25. In some embodiments, n is between 8 and 20. In some embodiments, n can be from about 10 to about 28, from about 12 to about 26, from about 14 to about 24, from about 16 to about 22, or from about 18 to about 20. In some embodiments, n can be from about 8 to about 50, from about 8 to about 45, from about 8 to about 40, from about 8 to about 35, from about 8 to about 30, from about 10 to about 25, from about 10 to about 20, or from about 10 to about 15.

In another aspect, the present invention provides a peptoid polymer or a salt thereof comprising: (a) subunits comprising two first hydrophobic peptoid monomers H and two first polar peptoid monomers P, and (b) two second hydrophobic peptoid monomers located at the C-terminal end of the peptoid polymer, arranged such that the peptoid polymer has the sequence $[H_2P_2]_nH_2$ or $[P_2H_2]_nH_2$, wherein the subscript n, representing the number of subunits within the peptoid polymer, is between 1 and 50.

In still another aspect, the present invention provides a peptoid polymer or a salt thereof comprising: (a) subunits comprising two first hydrophobic peptoid monomers H and two first polar peptoid monomers P, and (b) two second polar peptoid monomers located at the C-terminal end of the peptoid polymer, arranged such that the peptoid polymer has the sequence $[H_2P_2]_nP_2$ or $[P_2H_2]_nP_2$, wherein the subscript n, representing the number of subunits within the peptoid polymer, is between 1 and 50.

In varying embodiments, all of the hydrophobic peptoid monomers can be the same, they can all be different, or a combination thereof. Similarly, all of the polar peptoid monomers can be the same, they can all be different, or a combination thereof.

In some embodiments, the peptoid polymer or salt thereof further comprises substituents X and Y such that the peptoid polymer has the sequence X—$[H_2P_2]_nH_2$—Y, X—$[P_2H_2]_nH_2$—Y, X—$[H_2P_2]_nP_2$—Y, or X—$[P_2H_2]_nP_2$—Y. In some embodiments, X and Y are independently selected from the group consisting of H, optionally substituted $C_{1-8}$ alkyl, optionally substituted $C_{1-8}$ acyl, optionally substituted $C_{1-8}$ alkylamino, —OH, —SH, —NH$_2$, acetyl, carboxy, optionally substituted $C_{1-8}$ hydroxyalkyl, optionally substituted $C_{1-8}$ alkylamino, optionally substituted $C_{2-8}$ alkylthio, optionally substituted $C_{1-8}$ carboxyalkyl, and halogen. Alternatively, X and Y are taken together to form a covalent bond. The formation of a covalent bond between X and Y results in a circularized form of the peptoid polymer.

In some embodiments, X and Y are H, optionally substituted $C_{1-8}$ alkylamino, —OH, —SH, acetyl, carboxy, optionally substituted $C_{1-8}$ hydroxyalkyl, optionally substituted $C_{1-8}$ alkylamino, optionally substituted $C_{2-8}$ alkylthio, optionally substituted $C_{1-8}$ carboxyalkyl, or halogen. In other embodiments, X or Y is a secondary amine or a tertiary amine.

In some embodiments, n is between 1 and 50 (e.g., n is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50). In some instances, n is between 1 and 10 (e.g., n is 1, 2, 3, 4, 5, 6, 7, 8, 9, or 10). In some embodiments, n is between 1 and 25. In some embodiments, n is between 3 and 25. In some embodiments, n is between 5 and 25. In some embodiments, n is between 8 and 50. In some embodiments, n is between 8 and 25. In some embodiments, n is between 8 and 20. In some embodiments, n can be from about 10 to about 28, from about 12 to about 26, from about 14 to about 24, from about 16 to about 22, or from about 18 to about 20. In some embodiments, n can be from about 8 to about 50, from about 8 to about 45, from about 8 to about 40, from about 8 to about 35, from about 8 to about 30, from about 10 to about 25, from about 10 to about 20, or from about 10 to about 15.

In some embodiments, the peptoid polymer or salt thereof comprises Compound 62, Compound 63, Compound 67, Compound 73, Compound 76, Compound 86, or Compound 87 (i.e., when n is 2). In some instances, the peptoid polymer comprises Compound 76. In other embodiments, the peptoid polymer or salt thereof comprises Compound 81 (i.e., when n is 1).

In some embodiments, the first and/or second hydrophobic peptoid monomers are independently selected from the group consisting of

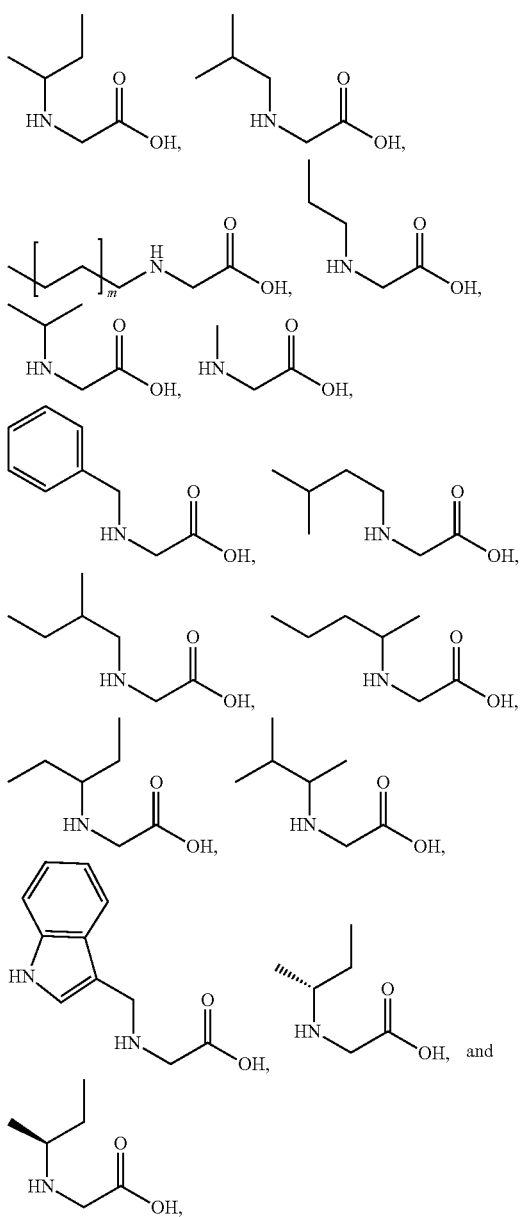

wherein the subscript m is the number of repeat units and is between 1 and 10 (e.g., m is 1, 2, 3, 4, 5, 6, 7, 8, 9, or 10). In some embodiments, the repeating unit, m, can be between 1 and 2, 1 and 3, 1 and 4, 1 and 5, 1 and 6, 1 and 7, 1 and 8, 1 and 9, or 1 and 10.

In some embodiments, at least 1, 2, 3, 4, 5, 6, 7, 8, 9, 10, 11, 12, 13, 14, 15, 16, 17, 18, 19, 20, or more hydrophobic peptoid monomers in the peptoid polymer or salt thereof have a side chain (e.g., $R^1$) that comprises an independently selected alkyl group where the alkyl group has 1, 2, 3, 4, 5, 6, 7, 8, 9, 10, 11, 12, 13, 14, 15, 16, 17, 18, or more carbon atoms. In particular embodiments, the alkyl group has 5 carbon atoms. In some instances, the 5-carbon alkyl group is a pentyl group. In other instances, the 5-carbon alkyl group is a substituted butyl group (e.g., 1-methylbutyl, 2-methylbutyl, 3-methylbutyl, and the like). In yet other instances, the 5-carbon alkyl group is a substituted propyl group (e.g., 1-ethylpropyl, 1,2-dimethylpropyl, and the like).

In some embodiments, the first and/or second polar peptoid monomers are independently selected from the group consisting of

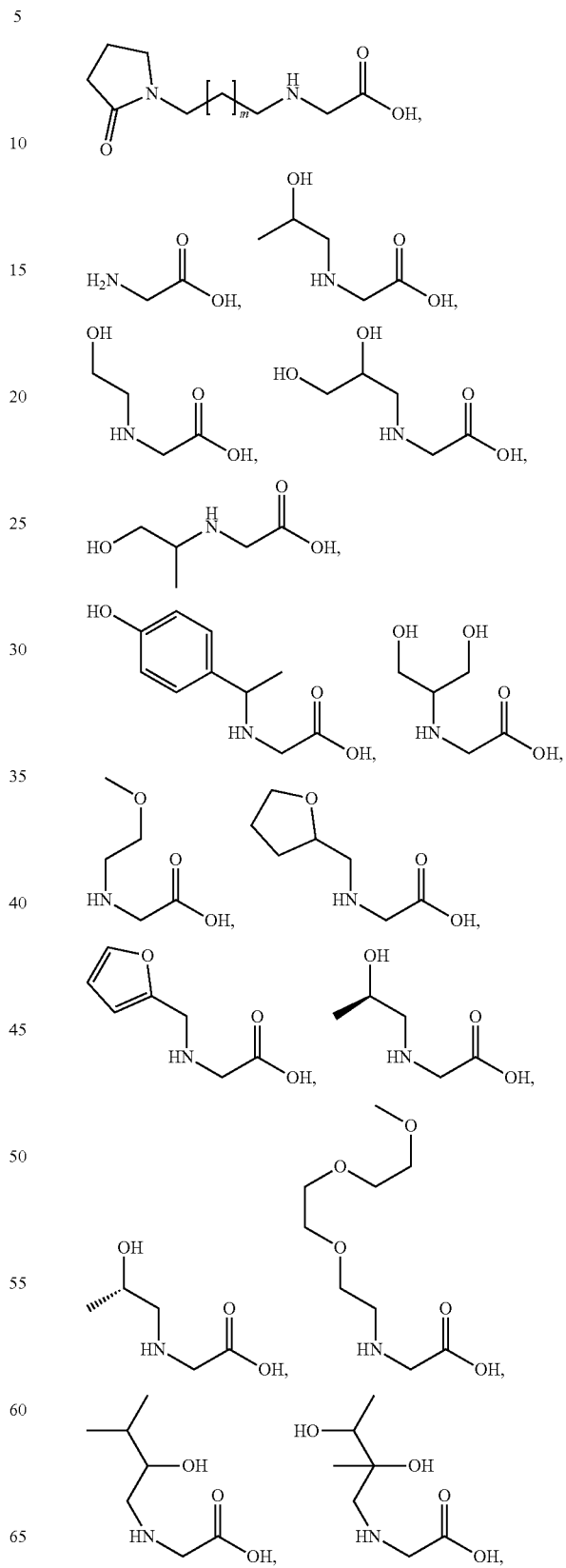

-continued
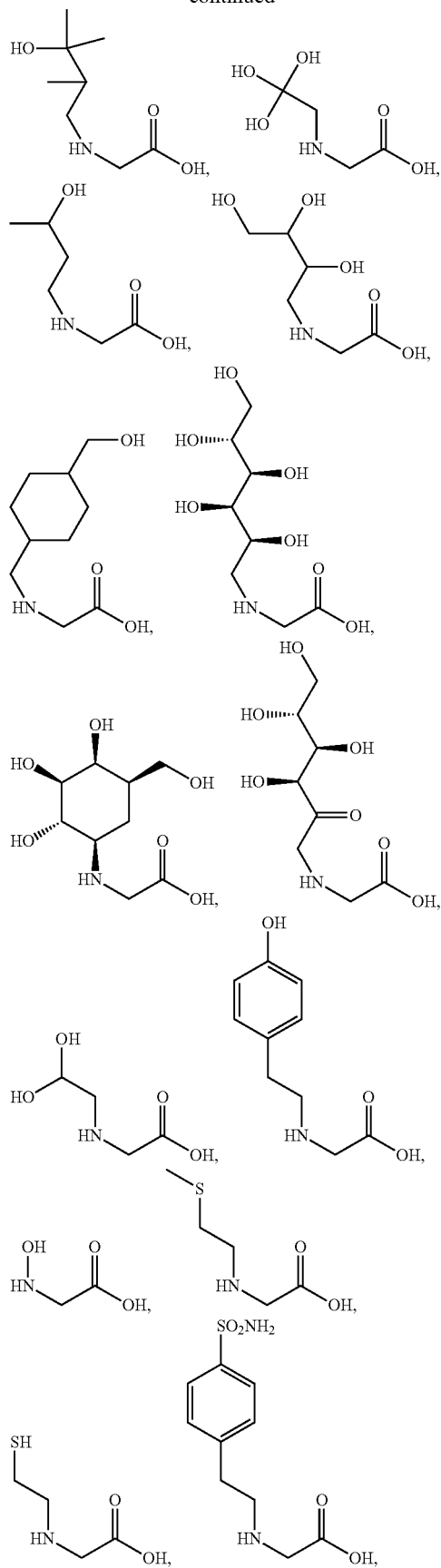
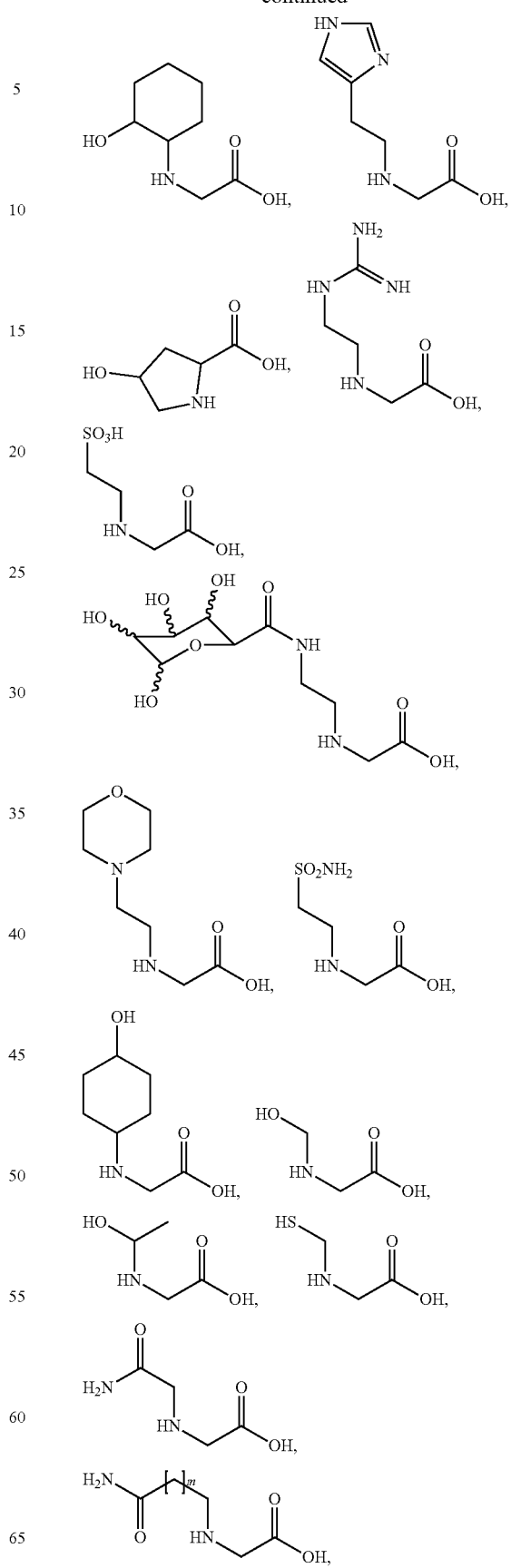

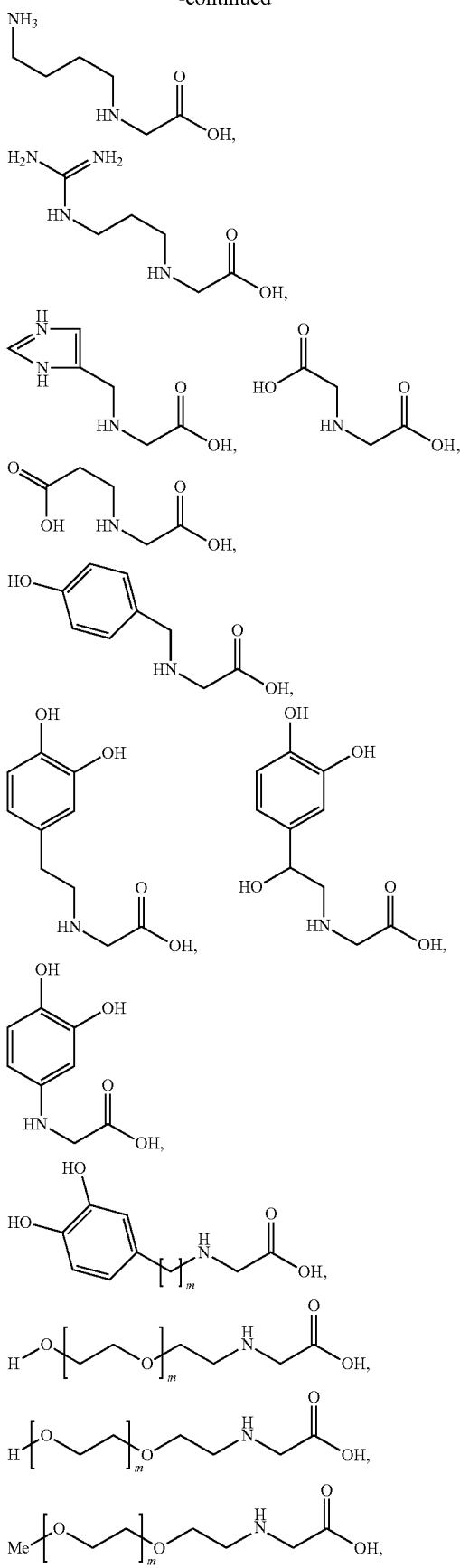
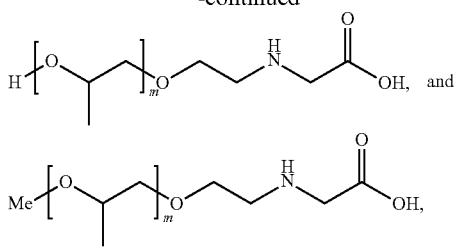

wherein the subscript m is the number of repeat units and is between 1 and 10 (e.g., m is 1, 2, 3, 4, 5, 6, 7, 8, 9, or 10). In some embodiments, the repeating unit, m, can be between 1 and 2, 1 and 3, 1 and 4, 1 and 5, 1 and 6, 1 and 7, 1 and 8, 1 and 9, or 1 and 10.

In some embodiments, the first and/or second polar peptoid monomer has a side chain (e.g., $R^1$) that comprises a hydroxyl group. In other embodiments, at least 1, 2, 3, 4, 5, 6, 7, 8, 9, 10, 11, 12, 13, 14, 15, 16, 17, 18, 19, 20, or more polar peptoid monomers in the peptoid polymer or salt thereof have a side chain (e.g., $R^1$) that comprises an independently selected $C_{1-18}$ hydroxyalkyl group (e.g., an independently selected $C_{1-6}$ hydroxyalkyl group). In some instances, each $C_{1-18}$ hydroxyalkyl group is a $C_{1-6}$ hydroxyalkyl group. In particular instances, each $C_{1-6}$ hydroxyalkyl group is the same $C_{1-6}$ hydroxyalkyl group. In some embodiments, at least 1, 2, 3, 4, 5, 6, 7, 8, 9, 10, 11, 12, 13, 14, 15, 16, 17, 18, 19, 20, or more polar peptoid monomers in the peptoid polymer or salt thereof have a side chain (e.g., $R^1$) that comprises an independently selected hydroxyalkyl group where the length of the alkyl in the hydroxyalkyl group is selected from 1, 2, 3, 4, 5, 6, 7, 8, 9, 10, 11, 12, 13, 14, 15, 16, 17, 18, or more carbon atoms. In particular embodiments, the hydroxyalkyl group contains 1, 2, 3, 4, 5, 6, 7, or 8 hydroxy substitutions.

In some embodiments, none of the polar peptoid monomers comprise a side chain (e.g., $R^1$) that comprises an optionally substituted $C_{1-18}$ hydroxyalkyl group.

In some embodiments, the side chain (e.g., $R^1$) of a polar peptoid monomer comprises a (4- to 10-membered heterocycloalkyl)($C_{1-6}$ alkylene) group or a (5- to 10-membered heteroaryl)($C_{1-6}$ alkylene) group. The alkylene moiety can be, for example, a straight-chain alkylene moiety such as methylene, ethylene, n-propylene (i.e., —CH$_2$CH$_2$CH$_2$—), or n-butylene (i.e., —CH$_2$CH$_2$CH$_2$CH$_2$—). The alkylene linker can also be a branched, as in the case of sec-butylene (i.e., —CH(CH$_3$)CH$_2$CH$_2$—) or iso-butylene (i.e., —CH$_2$CH(CH$_3$)CH$_2$—). In some embodiments, the alkylene moiety is methylene (i.e., —CH$_2$—). In some embodiments, the alkylene moiety is n-propylene. In some embodiments, at least one member of the 4-, 5-, 6-, 7-, 8-, 9-, or 10-membered ring is O. In other embodiments, at least one member of the 4-, 5-, 6-, 7-, 8-, 9-, or 10-membered ring is N.

The heterocycloalkyl moiety can be, but is not limited to, a 4- to 8-membered ring, a 4- to 6-membered ring, or a 5- to 6-membered ring. The heterocycloalkyl moiety can be, for example, azetidinyl, pyrrolidinyl, piperidinyl, azepanyl, azocanyl, pyrazolidinyl, imidazolidinyl, piperazinyl, tetrahydrofuranyl, tetrahydropyranyl, oxepanyl, tetrahydrothiophenyl, tetrahydrothiopyranyl, oxazolidinyl, isoxazolidinyl, thiazolidinyl, isothiazolidinyl, or morpholinyl. In some embodiments, the heterocycloalkyl moiety is selected from pyrrolidin-1-yl, pyrrolidin-2-yl, pyrrolidin-3-yl, tetrahydrofuran-2-yl, and tetrahydrofuran-3-yl. In some embodiments, the heterocycloalkyl moiety is pyrrolidin-1-yl. In some embodiments, the heterocycloalkyl moiety is tetrahydrofuran-2-yl. In some embodiments, one or more carbon ring members in pyrrolidinyl or tetrahydrofuranyl is substituted with oxo.

In some embodiments, the peptoid polymer comprises

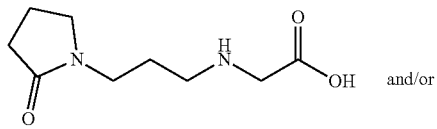 and/or

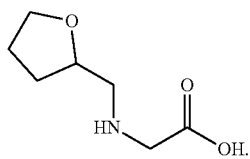

In some instances, the peptoid polymer comprises Compound 63, Compound 76, Compound 86, and/or Compound 87. In some embodiments, all of the polar peptoid monomers are

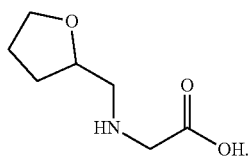 [SMILES: O=C(O)CNCC1CCCO1]

In other embodiments, all of the polar peptoid monomers are

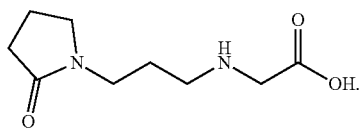 [SMILES: O=C(O)CNCCCN1CCCC1=O]

In some instances, the peptoid polymer is Compound 76, Compound 86, or Compound 87.

The heteroaryl moiety can be, but is not limited to, a 5- to 10-membered ring, a 5- to 9-membered ring, or a 5- to 6-membered ring. The heteroaryl moiety can be, for example, indolyl, quinolinyl, quinoxalinyl, quinazolinyl, phthalazinyl, cinnolinyl, benzofuranyl, pyrrolyl, pyridinyl, imidazolyl, pyrazolyl, pyrazinyl, pyrimidinyl, pyridazinyl, thiophenyl, or furanyl. In some embodiments, the heteroaryl moiety is selected from furan-2-yl, furan-3-yl, thiophen-2-yl, thiophen-3-yl, pyrrol-1-yl, pyrrol-2-yl, and pyrrol-3-yl.

In some embodiments, the side chain (e.g., $R^1$) comprises an (2-oxopyrrolidin-1-yl)($C_{1-4}$ alkylene) group. In some embodiments, the side chain (e.g., $R^1$) comprises a (tetrahydrofuran-2-yl)($C_{1-4}$ alkylene) group. In some embodiments, the side chain (e.g., $R^1$) comprises a (furan-2-yl)($C_{1-4}$ alkylene) group.

In some embodiments, the peptoid polymer comprises

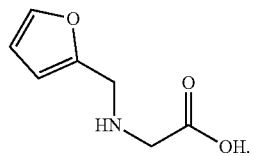 [SMILES: O=C(O)CNCc1ccco1]

In particular embodiments, all of the polar peptoid monomers are

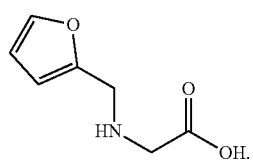 [SMILES: O=C(O)CNCc1ccco1]

In some instances, the peptoid polymer is Compound 73.

In some embodiments, the side chain (e.g., $R^1$) of a polar peptoid monomer comprises a 2- to 20-membered alkoxy group. The side chain (e.g., $R^1$) can comprise, for example, a 2-12 membered alkoxy group having from 1-4 oxygen atoms, or 2-6 membered alkoxy having 1 or 2 oxygen atoms. In some embodiments, the side chain (e.g., $R^1$) comprises —$CH_2CH_2OR'$, wherein R' is $C_{1-6}$ alkyl. In some embodiments, the side chain (e.g., $R^1$) comprises —$CH_2CH_2O(CH_2CH_2O)_nR'$, wherein R' is $C_{1-6}$ alkyl and subscript n is 1, 2, or 3.

In some embodiments, the side chain (e.g., $R^1$) comprises a ($C_{1-6}$ alkoxy)($C_{1-6}$ alkylene) group. In some embodiments, the side chain (e.g., $R^1$) comprises an (oligo[ethylene glycol]) or (oligo[propylene glycol]) group. In some embodiments, the side chain (e.g., $R^1$) comprises a methoxyethyl group. In some embodiments, the peptoid polymer comprises

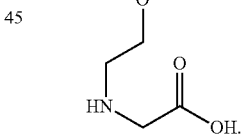

In particular embodiments, all of the polar peptoid monomers are

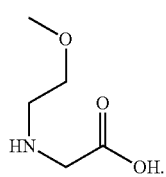

In some instances, the peptoid polymer is Compound 62.

In some embodiments, the oligo(ethylene glycol) moiety is a 2-(2-(2-methoxyethoxy)ethoxy)ethyl moiety. In some embodiments, the peptoid polymer comprises

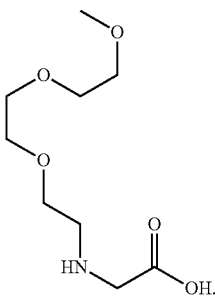

In particular embodiments, all of the polar peptoid monomers are

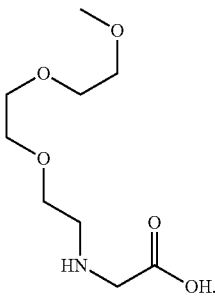

In some instances, the peptoid polymer is Compound 67.

In yet another aspect, the present invention provides a peptoid polymer or a salt thereof comprising one or more hydrophobic peptoid monomers and one or more polar peptoid monomers. In some embodiments, none of the polar peptoid monomers comprise a side chain (e.g., $R^1$) that comprises an optionally substituted $C_{1-18}$ hydroxyalkyl group. In some embodiments, the side chain (e.g., $R^1$) of a polar peptoid monomer comprises a (4- to 10-membered heterocycloalkyl)($C_{1-6}$ alkylene) group. In other embodiments, the side chain (e.g., $R^1$) of a polar peptoid monomer comprises a (5- to 10-membered heteroaryl)($C_{1-6}$ alkylene) group. In some embodiments, the side chain (e.g., $R^1$) of a polar peptoid monomer comprises a 2- to 20-membered alkoxy group. The side chain (e.g., $R^1$) can comprise, for example, 2-12 membered alkoxy having from 1-4 oxygen atoms, or 2-6 membered alkoxy having 1 or 2 oxygen atoms. In some embodiments, the side chain (e.g., $R^1$) comprises —CH$_2$CH$_2$OR', wherein R' is $C_{1-6}$ alkyl. In some embodiments, the side chain (e.g., $R^1$) comprises —CH$_2$CH$_2$O(CH$_2$CH$_2$O)$_n$R', wherein R' is $C_{1-6}$ alkyl and subscript n is 1, 2, or 3. In some embodiments, the side chain (e.g., $R^1$) of a polar peptoid monomer comprises a ($C_{1-6}$ alkoxy)($C_{1-6}$ alkylene) group. In some embodiments, the side chain (e.g., $R^1$) of a polar peptoid monomer comprises an (oligo[ethylene glycol]) or (oligo[propylene glycol]) group.

The alkylene moiety can be, for example, a straight-chain alkylene moiety such as methylene, ethylene, n-propylene (i.e., —CH$_2$CH$_2$CH$_2$—), or n-butylene (i.e., —CH$_2$CH$_2$CH$_2$CH$_2$—). The alkylene linker can also be a branched, as in the case of sec-butylene (i.e., —CH(CH$_3$)CH$_2$CH$_2$—) or iso-butylene (i.e., —CH$_2$CH(CH$_3$)CH$_2$—). In some embodiments, the alkylene moiety is methylene (i.e., —CH$_2$—). In some embodiments, the alkylene moiety is n-propylene. In some embodiments, at least one member of the 4-, 5-, 6-, 7-, 8-, 9-, or 10-membered ring is O. In other embodiments, at least one member of the 4-, 5-, 6-, 7-, 8-, 9-, or 10-membered ring is N.

The heterocycloalkyl moiety can be, but is not limited to, a 4- to 8-membered ring, a 4- to 6-membered ring, or a 5- to 6-membered ring. The heterocycloalkyl moiety can be, for example, azetidinyl, pyrrolidinyl, piperidinyl, azepanyl, azocanyl, pyrazolidinyl, imidazolidinyl, piperazinyl, tetrahydrofuranyl, tetrahydropyranyl, oxepanyl, tetrahydrothiophenyl, tetrahydrothiopyranyl, oxazolidinyl, isoxazolidinyl, thiazolidinyl, isothiazolidinyl, or morpholinyl. In some embodiments, the heterocycloalkyl moiety is selected from pyrrolidin-1-yl, pyrrolidin-2-yl, pyrrolidin-3-yl, tetrahydrofuran-2-yl, and tetrahydrofuran-3-yl. In some embodiments, the heterocycloalkyl moiety is pyrrolidin-1-yl. In some embodiments, the heterocycloalkyl moiety is tetrahydrofuran-2-yl. In some embodiments, one or more carbon ring members in pyrrolidinyl or tetrahydrofuranyl is substituted with oxo.

In some embodiments, the peptoid polymer comprises

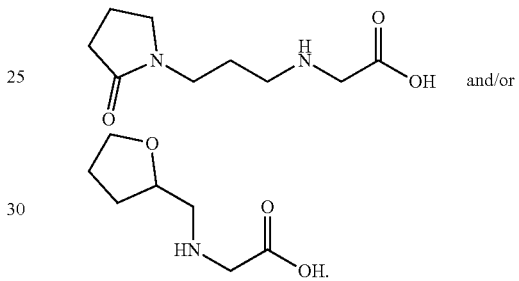

and/or

In some instances, the peptoid polymer comprises Compound 63, Compound 76, Compound 86, and/or Compound 87. In some embodiments, all of the polar peptoid monomers are

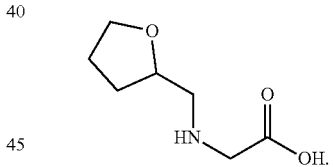

In other embodiments, all of the polar peptoid monomers are

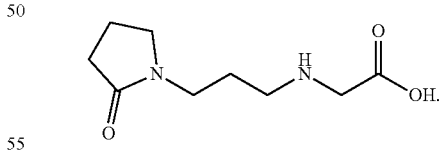

In some instances, the peptoid polymer is Compound 76, Compound 86, or Compound 87.

The heteroaryl moiety can be, but is not limited to, a 5- to 10-membered ring, a 5- to 9-membered ring, or a 5- to 6-membered ring. The heteroaryl moiety can be, for example, indolyl, quinolinyl, quinoxalinyl, quinazolinyl, phthalazinyl, cinnolinyl, benzofuranyl, pyrrolyl, pyridinyl, imidazolyl, pyrazolyl, pyrazinyl, pyrimidinyl, pyridazinyl, thiophenyl, or furanyl. In some embodiments, the heteroaryl moiety is selected from furan-2-yl, furan-3-yl, thiophen-2-yl, thiophen-3-yl, pyrrol-1-yl, pyrrol-2-yl, and pyrrol-3-yl.

In some embodiments, the side chain (e.g., $R^1$) comprises a (2-oxopyrrolidin-1-yl)($C_{1-4}$ alkylene) group. In some embodiments, the side chain (e.g., $R^2$) comprises a (tetrahydrofuran-2-yl)($C_{1-4}$ alkylene) group. In some embodiments, the side chain (e.g., $R^2$) comprises a (furan-2-yl)($C_{1-4}$ alkylene).

In some embodiments, the peptoid polymer comprises

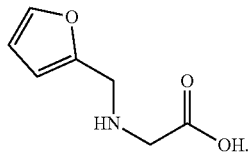 [SMILES: O=C(O)CNCc1ccco1]

In particular embodiments, all of the polar peptoid monomers are

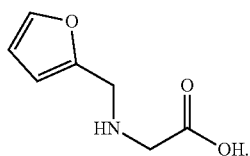 [SMILES: O=C(O)CNCc1ccco1]

In some instances, the peptoid polymer is Compound 73.

In some embodiments, the side chain (e.g., $R^2$) comprises a methoxyethyl group. In some embodiments, the peptoid polymer comprises

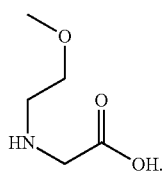

In particular embodiments, all of the polar peptoid monomers are

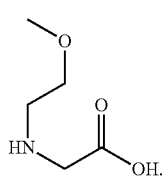

In some instances, the peptoid polymer is Compound 62.

In some embodiments, the oligo(ethylene glycol) moiety is a 2-(2-(2-methoxyethoxy)ethoxy)ethyl moiety. In some embodiments, the peptoid polymer comprises

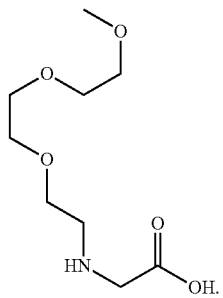

In particular embodiments, all of the polar peptoid monomers are

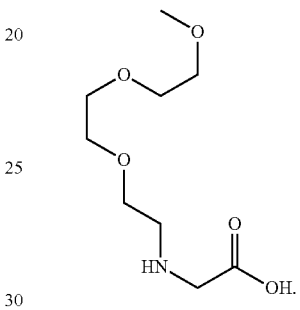

In some instances, the peptoid polymer is Compound 67.

In some embodiments, each of the one or more hydrophobic peptoid monomers are independently selected from the group consisting of

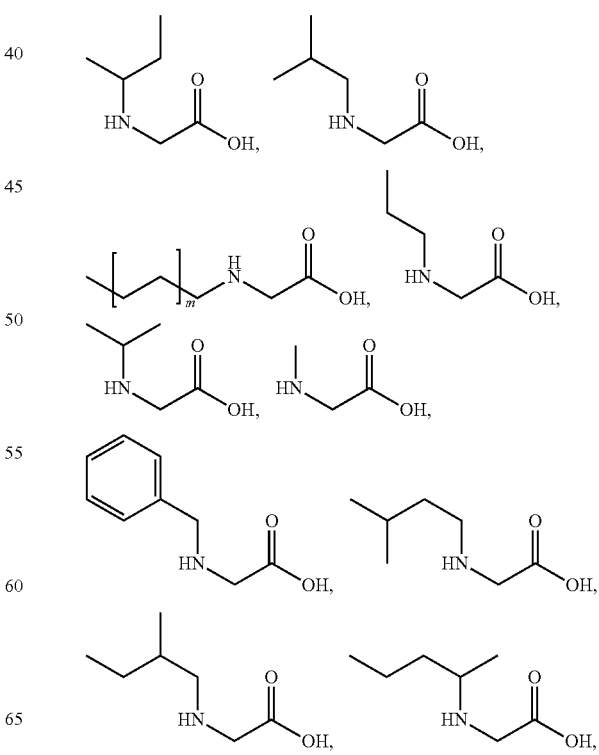

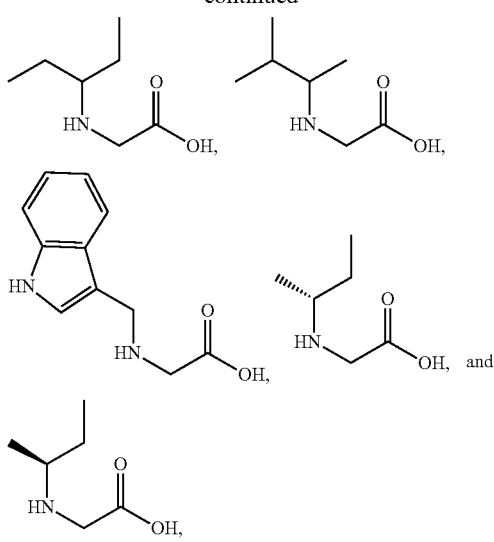

wherein the subscript m is the number of repeat units and is between 1 and 10.

In some embodiments, each of the one or more polar peptoid monomers are independently selected from the group consisting of

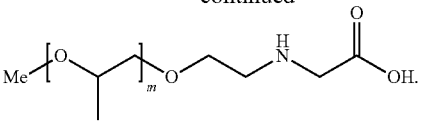

In some embodiments, the peptoid polymer further comprises substituents X and Y located at the N-terminal and C-terminal ends of the peptoid polymer, respectively. In some embodiments, X and Y are independently selected from the group consisting of H, optionally substituted $C_{1-8}$ alkyl, optionally substituted $C_{1-8}$ acyl, optionally substituted $C_{1-8}$ alkylamino, —OH, —SH, —NH$_2$, acetyl, carboxy, optionally substituted $C_{1-8}$ hydroxyalkyl, optionally substituted $C_{1-8}$ alkylamino, optionally substituted $C_{2-8}$ alkylthio, optionally substituted $C_{1-8}$ carboxyalkyl, and halogen. Alternatively, X and Y are taken together to form a covalent bond. The formation of a covalent bond between X and Y results in a circularized form of the peptoid polymer.

In some embodiments, X and Y are H, optionally substituted $C_{1-8}$ alkylamino, —OH, —SH, acetyl, carboxy, optionally substituted $C_{1-8}$ hydroxyalkyl, optionally substituted $C_{1-8}$ alkylamino, optionally substituted $C_{2-8}$ alkylthio, optionally substituted $C_{1-8}$ carboxyalkyl, or halogen. In other embodiments, X or Y is a secondary amine or a tertiary amine.

In some embodiments, the sequence length of a peptoid polymer described herein is between 6 and 50. In some embodiments, the sequence length of the peptoid polymer is between 10 and 50. In some embodiments, the sequence length of the peptoid polymer is between 16 and 100. In some embodiments, the sequence length of the peptoid polymer is between 16 and 50. In some embodiments, the sequence length of the peptoid polymer is between 16 and 40. In some embodiments, the sequence length of the peptoid polymer can be from about 20 to about 56, from about 24 to about 52, from about 28 to about 48, from about 32 to about 44, or from about 36 to about 40. In some embodiments, the sequence length of the peptoid polymer can be from about 16 to about 100, from about 16 to about 90, from about 16 to about 80, from about 16 to about 70, from about 16 to about 60, from about 20 to about 50, from about 20 to about 40, or from about 20 to about 30. In some embodiments, the sequence length of the peptoid polymer can be 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more.

In some embodiments, between about 1 percent and about 99 percent (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent) of the peptoid monomers in the peptoid polymer or salt thereof are hydrophobic peptoid monomers. In other embodiments, between about 1 percent and about 99 percent (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent) of the peptoid monomers in the peptoid polymer or salt thereof are polar peptoid monomers.

In some embodiments, about 5 percent of the peptoid monomers in the peptoid polymer or salt thereof are hydrophobic and about 95 percent of the peptoid monomers are polar.

In some embodiments, about 10 percent of the peptoid monomers in the peptoid polymer or salt thereof are hydrophobic and about 90 percent of the peptoid monomers are polar.

In some embodiments, about 15 percent of the peptoid monomers in the peptoid polymer or salt thereof are hydrophobic and about 85 percent of the peptoid monomers are polar.

In some embodiments, about 20 percent of the peptoid monomers in the peptoid polymer or salt thereof are hydrophobic and about 80 percent of the peptoid monomers are polar.

In some embodiments, about 25 percent of the peptoid monomers in the peptoid polymer or salt thereof are hydrophobic and about 75 percent of the peptoid monomers are polar.

In some embodiments, about 30 percent of the peptoid monomers in the peptoid polymer or salt thereof are hydrophobic and about 70 percent of the peptoid monomers are polar.

In some embodiments, about 35 percent of the peptoid monomers in the peptoid polymer or salt thereof are hydrophobic and about 65 percent of the peptoid monomers are polar.

In some embodiments, about 40 percent of the peptoid monomers in the peptoid polymer or salt thereof are hydrophobic and about 60 percent of the peptoid monomers are polar.

In some embodiments, about 45 percent of the peptoid monomers in the peptoid polymer or salt thereof are hydrophobic and about 55 percent of the peptoid monomers are polar.

In some embodiments, about 50 percent of the peptoid monomers in the peptoid polymer or salt thereof are hydrophobic and about 50 percent of the peptoid monomers are polar.

In some embodiments, about 55 percent of the peptoid monomers in the peptoid polymer or salt thereof are hydrophobic and about 45 percent of the peptoid monomers are polar.

In some embodiments, about 60 percent of the peptoid monomers in the peptoid polymer or salt thereof are hydrophobic and about 40 percent of the peptoid monomers are polar.

In some embodiments, about 65 percent of the peptoid monomers in the peptoid polymer or salt thereof are hydrophobic and about 35 percent of the peptoid monomers are polar.

In some embodiments, about 70 percent of the peptoid monomers in the peptoid polymer or salt thereof are hydrophobic and about 30 percent of the peptoid monomers are polar.

In some embodiments, about 75 percent of the peptoid monomers in the peptoid polymer or salt thereof are hydrophobic and about 25 percent of the peptoid monomers are polar.

In some embodiments, about 80 percent of the peptoid monomers in the peptoid polymer or salt thereof are hydrophobic and about 20 percent of the peptoid monomers are polar.

In some embodiments, about 85 percent of the peptoid monomers in the peptoid polymer or salt thereof are hydrophobic and about 15 percent of the peptoid monomers are polar.

In some embodiments, about 90 percent of the peptoid monomers in the peptoid polymer or salt thereof are hydrophobic and about 10 percent of the peptoid monomers are polar.

In some embodiments, about 95 percent of the peptoid monomers in the peptoid polymer or salt thereof are hydrophobic and about 5 percent of the peptoid monomers are polar.

In particular embodiments, the peptoid polymer or salt thereof comprises about 5, 10, 15, 20, 25, 30, 35, 40, 45, 50, 55, 60, 65, 70, 75, 80, 85, 90, or 95 percent hydrophobic peptoid monomers by mass. In other embodiments, the peptoid polymer or salt thereof comprises about 5, 10, 15, 20, 25, 30, 35, 40, 45, 50, 55, 60, 65, 70, 75, 80, 85, 90, or 95 percent polar peptoid monomers by mass.

In some embodiments, the peptoid polymer forms a helical structure. In some embodiments, the helical structure adopts a structure analogous to a polyproline helix. In certain instances, the peptoid polymer forms a polyproline I helix. In certain other instances, the peptoid polymer forms a polyproline II helix. In some embodiments, a helical structure is adopted when the peptoid polymer comprises at least one N-Aryl side chain. In some embodiments, the N-Aryl side chain is a Nep monomer.

In some embodiments, the peptoid polymer or salt thereof reduces or inhibits ice crystal formation at a temperature within about 0° C. to about −20° C. (e.g., at about 0, −1, −2, −3, −4, −5, −6, −7, −8, −9, −10, −11, −12, −13, −14, −15, −16, −17, −18, −19, or −20° C.). In other embodiments, the peptoid polymer or salt thereof reduces or inhibits ice crystal formation at a temperature within about −20° C. to about −40° C. (e.g., at about −20, −21, −22, −23, −24, −25, −26, −27, −28, −29, −30, −31, −32, −33, −34, −35, −36, −37, −38, −39, or −40° C.). In certain embodiments, the peptoid polymer or salt thereof reduces or inhibits ice crystal formation at about −20° C. In certain other embodiments, the peptoid polymer or salt thereof reduces or inhibits ice crystal formation at a temperature within about −40° C. to about −200° C. (e.g., at about −40, −45, −50, −55, −60, −65, −70, −75, −80, −85, −90, −95, −100, −105, −110, −115, −120, −125, −130, −135, −140, −145, −150, −155, −160, −165, −170, −175, −180, −185, −190, −195, or −200° C.). In some instances, the peptoid polymer or salt thereof reduces or inhibits ice crystal formation at about −196° C.

In some embodiments, the peptoid polymer or salt thereof reduces or inhibits ice crystal formation at a temperature within about 0° C. to about −200° C., within about −10° C. to about −190° C., within about −20° C. to about −180° C., within about −30° C. to about −170° C., within about −40° C. to about −160° C., within about −50° C. to about −150° C., within about −60° C. to about −140° C., within about −70° C. to about −140° C., within about −80° C. to about −130° C., within about −90° C. to about −120° C., or within about −100° C. to about −110° C.

In some embodiments, the concentration of the peptoid polymer and/or salt thereof (e.g., present in a composition, formulation, or product such as a cryoprotectant solution, antifreeze solution, frozen food product, or cosmetic care product) is between about 100 nM and about 1,000 mM. In certain embodiments, the concentration of the peptoid polymer and/or salt thereof (e.g., present in a composition, formulation, or product such as a cryoprotectant solution, antifreeze solution, frozen food product, or cosmetic care product) is between about 100 nM and about 250 nM, between about 250 nM and about 500 nM, between about 500 nM and about 750 nM, between about 750 nM and about 1 µM, between about 1 µM and about 5 µM, between about 5 µM and about 25 µM, between about 25 µM and about 50 µM, between about 50 µM and about 100 µM, between about 100 µM and about 250 µM, between about 250 µM and about 500 µM, between about 500 µM and about 750 µM, between about 750 µM and about 1 mM, between about 1 mM and about 10 mM, between about 10 mM and about 50 mM, between about 50 mM and about 100 mM, between about 100 mM and about 250 mM, between about 250 mM and about 500 mM, between about 500 mM and about 750 mM, or between about 750 mM and about 1,000 mM. In other embodiments, the concentration of the peptoid polymer and/or salt thereof (e.g., present in a composition, formulation, or product such as a cryoprotectant solution, antifreeze solution, frozen food product, or cosmetic care product) is about 100 nM, about 1 µM, about 10 µM, about 100 µM, about 1 mM, about 10 mM, about 100 mM, or about 1,000 mM. In particular embodiments, the concentration of the peptoid polymer and/or salt thereof is about 1, 2, 3, 4, 5, 6, 7, 8, 9, or 10 mM.

For embodiments of the present invention in which the peptoid polymer is made or used as a salt, any number of salt forms can be made or used. Non-limiting examples of suitable salt forms include hydrochloride, acetate, sulfate, phosphate, maleate, citrate, mesylate, nitrate, tartrate, and gluconate salts. Furthermore, any suitable combination of peptoid polymer salt forms can be made or used.

In some embodiments, the peptoid polymer or salt thereof comprises a peptoid polymer selected from the group consisting of Compound 59, Compound 60, Compound 61, Compound 62, Compound 63, Compound 64, Compound 65, Compound 66, Compound 67, Compound 68, Compound 69, Compound 70, Compound 71, Compound 72, Compound 73, Compound 74, Compound 75, Compound 76, Compound 77, Compound 78, Compound 79, Compound 80, Compound 81, Compound 82, Compound 83, Compound 84, Compound 85, Compound 86, and Compound 87. In some embodiments, the peptoid polymer or salt thereof comprises a peptoid polymer selected from the group consisting of Compound 88, Compound 89, Compound 90, Compound 91, Compound 92, Compound 93, Compound 94, Compound 95, Compound 96, Compound 97, Compound 98, Compound 99, Compound 100, and Compound 101. In particular embodiments, the peptoid polymer is Compound 62, 63, 67, 73, 76, 86, or 87. In some instances, the peptoid polymer is Compound 76, 86, or 87.

In some embodiments, the peptoid polymer is not a peptoid polymer set forth in Table 2, Table 3, Table 4, Table 5, Table 6, Table 7, Table 8, or Table 9.

B. Peptoid-Peptide Hybrids

In another aspect, the invention provides a peptoid-peptide hybrid or a salt thereof. In some embodiments, the peptoid-peptide hybrid or salt thereof comprises a peptoid polymer described herein and one or more amino acids. The amino acids can be naturally-occurring amino acids or variants thereof. In some embodiments, the peptoid-peptide hybrid or salt thereof comprises between about 1 and 10 amino acids (e.g., about 1, 2, 3, 4, 5, 6, 7, 8, 9, or 10 amino acids). In other embodiments, the peptoid-peptide hybrid or salt thereof comprises between about 10 and 100 amino acids (e.g., about 10, 15, 20, 25, 30, 35, 40, 45, 50, 55, 60, 65, 70, 75, 80, 85, 90, 95, or 100 amino acids). In some embodiments, the peptoid-peptide hybrid or salt thereof comprises more than about 100 amino acids. In other embodiments, the peptoid-peptide hybrid or salt thereof comprises between 2 and 50 peptoid monomers (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 44, 45, 46, 47, 48, 49, or 50 peptoid monomers) and at least between about 1 and 100 amino acids (e.g., at least about 1, 2, 3, 4, 5, 6, 7, 8, 9, 10, 15, 20, 25, 30, 35, 40, 45, 50, 55, 60, 65, 70, 75, 80, 85, 90, 95, or 100 amino acids).

In some embodiments, the amino acids are located at the N- and/or C-terminal ends of the peptoid polymer. In other embodiments, the amino acids are located between one or more subunits of the peptoid polymer. In particular embodiments, the amino acids are located at one or both ends of the peptoid polymer and between one or more subunits. In instances where the peptoid-peptide hybrid or salt thereof comprises two or more amino acids, the amino acids may all be contiguous, or only a portion of them may be contiguous. Alternatively, all of the amino acids may be separated by one or more subunits.

In some embodiments, the amino acids are D-amino acids. In other embodiments, the amino acids are L-amino acids. In some other embodiments, the peptoid-peptide hybrid or salt thereof comprises a combination of D- and L-amino acids. In some embodiments, the one or more amino acids are selected from the group consisting of alanine, cysteine, aspartic acid, glutamic acid, phenylalanine, glycine, histidine, isoleucine, arginine, lysine, leucine, methionine, asparagine, proline, glutamine, serine, threonine, valine, tryptophan, tyrosine, and a combination thereof. In some instances, the one or more amino acids are selected from the group consisting of isoleucine, leucine, serine, threonine, alanine, valine, arginine, and a combination thereof.

In particular embodiments, the peptoid-peptide hybrid or salt thereof comprises about 5, 10, 15, 20, 25, 30, 35, 40, 45, 50, 55, 60, 65, 70, 75, 80, 85, 90, or 95 percent hydrophobic peptoid monomers by mass. In other embodiments, the peptoid-peptide hybrid or salt thereof comprises about 5, 10, 15, 20, 25, 30, 35, 40, 45, 50, 55, 60, 65, 70, 75, 80, 85, 90, or 95 percent polar peptoid monomers by mass.

For embodiments of the present invention in which the peptoid-peptide hybrid is made or used as a salt, any number of salt forms can be made or used. Non-limiting examples of suitable salt forms include hydrochloride, acetate, sulfate, phosphate, maleate, citrate, mesylate, nitrate, tartrate, and gluconate salts. Furthermore, any suitable combination of peptoid polymer salt forms can be made or used.

In some embodiments, the peptoid-peptide hybrid is not Nep-Nep-Xaa-Xaa-Xaa-Xaa-Nep-Nep-Nep-Nep-Nme-Nme, Nme-Nme-Xaa-Nme-Nme-Nme-Nme-Nhp-Nhp-Nsb-Xaa-Nme-Nme-Xaa-Nme-Nme-Nme, Nme-Nme-Xaa-Nme-Nme-Nme-Nme-Nme-Nme-Nme-Xaa-Xaa, or Arg-Nsb-Nsb-Nhp-Nhp-Nsb-Nsb-Nhp-Nhp-Nsb-Nsb. Xaa denotes any amino acid.

C. Methods of Synthesis

In another aspect, the invention herein provides a method of synthesizing a peptoid polymer and/or a salt thereof or a peptoid-peptide hybrid and/or a salt thereof. The peptoid polymers, peptoid polymer salts, peptoid-peptide hybrids, and peptoid-peptide hybrid salts of the invention can be prepared from readily available starting materials using the general methods and procedures described herein. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

The peptoid polymers, peptide polymer salts, peptoid-peptide hybrids, and peptoid-peptide hybrid salts of the invention may be prepared from known or commercially available starting materials and reagents by one skilled in the art of organic synthesis. Solvents and reagents are purchased from commercial sources and used without further purification.

In some embodiments, the submonomer approach (FIG. 1) is used for peptoid synthesis, where each N-substituted glycine monomer is assembled from two readily available "submonomers." The synthesis of oligomeric peptoids is based on the robust chemistry of standard solid-phase methods, analogous to peptide synthesis. Each cycle of monomer addition consists of two steps, an acylation step and a nucleophilic displacement step. In some embodiments, solid-phase assembly eliminates the need for N-protected monomers because there are no reactive side chain functionalities that need to be protected. One of skill in the art will recognize there are many solid-phase synthesis methods, including automated, robotic synthesizers. In some embodiments, the synthesizer used is the Symphony© X Multiplex Peptide Synthesizer made by Protein Technologies, Inc. In some embodiments, the synthesizer used is the Overture Peptide Synthesizer made by Protein Technologies, Inc. In other embodiments, the peptoids are synthesized manually using traditional organic chemistry methods known in the art. By providing the appropriate amino acids in place of peptoid monomers at the appropriate times during synthesis, the same techniques or techniques similar to those described above can be applied to the synthesis of peptoid-peptide oligomers.

As a non-limiting example, peptoid polymers can be synthesized on 100 mg of Rink amide resin (NovaBiochem; 0.49 mmol/g). Rink amide resin (100 mg) can be washed twice in 1.5 mL of DCM, followed by swelling in 1.5 mL of DMF. The swelling step can be performed twice. The Fmoc protecting group can be removed from the resin by addition of 20% piperidine/DMF. The mixture can be agitated for 10 minutes, drained, and the piperidine treatment repeated, followed by extensive washes with DMF (five times with 1.5 mL). The first monomer can be added manually by reacting 37 mg of bromoacetic acid (0.27 mmol; Sigma-Aldrich) and 189 µL of DIEA (1.08 mmol; Chem Impex International) in 2 mL of DCM on a shaker platform for 30 minutes at room temperature, followed by extensive washes with DCM (five times with 2 mL) and DMF (five times with 2 mL). Bromoacylated resin can be incubated with 2 mL of 1 M amine submonomer in DMF on a shaker platform for 30 minutes at room temperature, followed by extensive washes with DMF (five times with 2 mL). After initial manual loading of bromoacetic acid, the first submonomer displacement step and all subsequent bromo acetylation and amine displacement steps can be performed by a robotic synthesizer until the desired oligomer length is obtained. The automated bromoacetylation step can be performed by adding 1,660 µL of 1.2 M bromoacetic acid in DMF and 400 µL of DIC (Chem Impex International). The mixture can be agitated for 20 min, drained, and washed with DMF (three times with 2 mL). Next, 2 mL of a 1 M solution of submonomer (2 mmol) in DMF can be added to introduce the side chain by nucleophilic displacement of bromide. The mixture can be agitated for 20 min, drained, washed with DMF (three times with 2 mL) and washed with DCM (three times with 2 mL). The peptoid-resin can be cleaved in 2 mL of 20% HFIP (Alfa Aesar) in DCM (v/v) at room temperature. The cleavage can be conducted in a glass tube with constant agitation for 30 minutes. HFIP/DCM can be evaporated under a stream of nitrogen gas. The final product can be dissolved in 5 mL of 50% ACN in HPLC grade $H_2O$ and filtered with a 0.5 µm stainless steel fritted syringe tip filter (Upchurch Scientific). Peptoid oligomers can be analyzed on a Cis reversed-phase analytical HPLC column at room temperature (Peeke Scientific, 5 µm, 120 Å, 2.0×50 mm) using a Beckman Coulter System Gold instrument. A linear gradient of 5-95% acetonitrile/water (0.1% TFA, Acros Organics) over 20 min can be used with a flow rate of 0.7 mL/min. In order to remove any traces of HFIP in the sample solution, linear precursors dissolved in 50% ACN/$H_2O$ can be freeze-dried overnight.

Peptoid polymers and peptoid-peptide hybrids can be analyzed by electrospray ionization (ESI) mass spectrometry. Generally, 0.5-2 mL of 1-5 µM of peptoid polymer or peptoid-peptide hybrid to be analyzed is prepared in a 50% deionized $H_2O$/50% HPLC grade ACN with 1% of an organic acid such as trifluoroacetic acid. Prepared samples are ionized by bombardment with electrons causing the molecules to break into charged fragments. The ions are then separated according to their mass-to-charge ratio by accelerating the fragments and exposing them to an electrical or magnetic field. The ions are detected by a mechanism capable of detecting charged particles, such as an electron multiplier. Peptoids and peptoid-peptide hybrids are identified by correlating masses to the identified masses or through a characteristic fragmentation pattern.

D. Methods of Use

In some aspects, the present invention provides a cryoprotectant solution. In some embodiments, the cryoprotectant solution comprises a peptoid polymer and/or a salt thereof described herein, a peptoid-peptide hybrid and/or a salt thereof described herein, or a combination thereof. In other embodiments, the cryoprotectant solution further comprises a compound selected from the group consisting of an ionic species, a penetrating cryoprotectant, a non-penetrating cryoprotectant, an antioxidant, a cell membrane stabilizing compound, an aquaporin or other channel forming compound, an alcohol, a sugar, a sugar derivative, a non-ionic surfactant, a protein, dimethyl sulfoxide (DMSO), polyethylene glycol (PEG), polypropylene glycol (PPG), Ficoll©, polyvinylpyrrolidone, polyvinyl alcohol, hyaluronan, formamide, a natural or synthetic hydrogel, and a combination thereof. In particular embodiments, the penetrating cryoprotectant penetrates the cell membrane and reduces the intracellular water concentration, thereby reducing the amount of ice formed at any temperature. In other particular embodiments, the non-penetrating cryoprotectant induces changes in colloidal osmotic pressure and modifies cell membrane associations with extracellular water by induced ionic interaction.

In some instances, the cryoprotectant solution further comprises an alcohol that is selected from the group consisting of propylene glycol, ethylene glycol, glycerol, methanol, butylene glycol, adonitol, ethanol, trimethylene glycol, diethylene glycol, polyethylene oxide, erythritol, sorbitol, xythyritol, polypropylene glycol, 2-methyl-2,4-pentanediol (MPD), mannitol, inositol, dithioritol, 1,2-propanediol, and a combination thereof.

In other instances, the cryoprotectant solution further comprises a sugar that is selected from the group consisting of a monosaccharide, a disaccharide, a polysaccharide, and a combination thereof. In particular instances, the sugar is selected from the group consisting of glucose, 3-O-methyl-D-glucopyranose, galactose, arabinose, fructose, xylose, mannose, sucrose, trehalose, lactose, maltose, raffinose, dextran, and a combination thereof.

In other instances, the cryoprotectant solution further comprises PEG or a plurality of different PEG compounds. In some instances, at least one of the PEG compounds has an average molecular weight less than about 3,000 g/mol (e.g., less than about 3,000, 2,950, 2,900, 2,850, 2,800, 2,750, 2,700, 2,650, 2,600, 2,550, 2,500, 2,450, 2,400, 2,350, 2,300, 2,250, 2,200, 2,150, 2,100, 2,050, 2,000, 1,950, 1,900, 1,850, 1,800, 1,750, 1,700, 1,650, 1,600, 1,550, 1,500, 1,450, 1,400, 1,350, 1,300, 1,250, 1,200, 1,150, 1,100, 1,050, 1,000, 950, 900, 850, 800, 750, 700, 650, 600, 550, 500, 450, 400, 350, 300, 250, 200, 150, or 100 g/mol). In particular instances, at least one of the PEG compounds has an average molecular weight between about 200 g/mol and 400 g/mol (e.g., about 200, 210, 220, 230, 240, 250, 260, 270, 280, 290, 300, 310, 320, 330, 340, 350, 360, 370, 380, 390, or 400 g/mol). In some instances, the cryoprotectant solution comprises PEG or a plurality of PEG compounds selected from the group consisting of PEG 200, PEG 300, PEG 400, and a combination thereof.

In other instances, the cryoprotectant solution further comprises PPG or a plurality of different PPG compounds. In some instances, at least one of the PPG compounds has an average molecular weight less than about 3,000 g/mol (e.g., less than about 3,000, 2,950, 2,900, 2,850, 2,800, 2,750, 2,700, 2,650, 2,600, 2,550, 2,500, 2,450, 2,400, 2,350, 2,300, 2,250, 2,200, 2,150, 2,100, 2,050, 2,000, 1,950, 1,900, 1,850, 1,800, 1,750, 1,700, 1,650, 1,600, 1,550, 1,500, 1,450, 1,400, 1,350, 1,300, 1,250, 1,200, 1,150, 1,100, 1,050, 1,000, 950, 900, 850, 800, 750, 700, 650, 600, 550, 500, 450, 400, 350, 300, 250, 200, 150, or 100 g/mol). In particular instances, at least one of the PPG compounds has an average molecular weight between about 200 g/mol and 400 g/mol (e.g., about 200, 210, 220, 230, 240, 250, 260, 270, 280, 290, 300, 310, 320, 330, 340, 350, 360, 370, 380, 390, or 400 g/mol).

In other instances, the cryoprotectant solution further comprises a protein that is selected from the group consisting of egg albumin, bovine serum albumin, human serum albumin, gelatin, and a combination thereof. In still other instances, the cryoprotectant solution further comprises a natural or synthetic hydrogel, wherein the natural or synthetic hydrogel comprises chitosan, hyaluronic acid, or a combination thereof. In yet other instances, the cryoprotectant solution further comprises a nonionic surfactant selected from the group consisting of polyoxyethylene lauryl ether, polysorbate 80, and a combination thereof.

Non-limiting examples of various properties of the cryoprotectant solution such as effective concentration, viscosity, water solubility, and/or membrane permeability can be assessed using a model cell or tissue including, but not limited to, stem cells, liver tissue or hepatocytes, kidney, intestine, heart, pancreas, genitourinary cells (e.g., sperm cells, oocytes, corpus cavernosum cells (e.g., smooth muscle corpus cavernosum cells, epithelial corpus cavernosum cells), urinary bladder cells, urethral cells, ureter cells, kidney cells, testicular cells), bone marrow, primary cells, organoids, and other biological tissues for cryopreservation.

In some embodiments, the cryoprotectant solution reduces or inhibits ice crystal formation at a temperature within about 0° C. to about −20° C. (e.g., at about 0, −1, −2, −3, −4, −5, −6, −7, −8, −9, −10, −11, −12, −13, −14, −15, −16, −17, −18, −19, or −20° C.). In other embodiments, the cryoprotectant solution reduces or inhibits ice crystal formation at a temperature within about −20° C. to about −40° C. (e.g., at about −20, −21, −22, −23, −24, −25, −26, −27, −28, −29, −30, −31, −32, −33, −34, −35, −36, −37, −38, −39, or −40° C.). In certain embodiments, the cryoprotectant solution reduces or inhibits ice crystal formation at about −20° C. In certain other embodiments, the cryoprotectant solution reduces or inhibits ice crystal formation at a temperature within about −40° C. to about −200° C. (e.g., at about −40, −45, −50, −55, −60, −65, −70, −75, −80, −85, −90, −95, −100, −105, −110, −115, −120, −125, −130, −135, −140, −145, −150, −155, −160, −165, −170, −175, −180, −185, −190, −195, or −200° C.). In some instances, the cryoprotectant solution reduces or inhibits ice crystal formation at about −196° C.

In some embodiments, the cryoprotectant solution reduces or inhibits ice crystal formation at a temperature within about 0° C. to about −200° C., within about −10° C. to about −190° C., within about −20° C. to about −180° C., within about −30° C. to about −170° C., within about −40° C. to about −160° C., within about −50° C. to about −150° C., within about −60° C. to about −140° C., within about −70° C. to about −140° C., within about −80° C. to about −130° C., within about −90° C. to about −120° C., or within about −100° C. to about −110° C.

In some embodiments, the concentration of the peptoid polymer and/or salt thereof and/or peptoid-peptide hybrid and/or salt thereof in the cryoprotectant solution is between about 100 nM and about 1,000 mM. In some embodiments, the concentration of the peptoid polymer and/or salt thereof and/or peptoid-peptide hybrid and/or salt thereof in the cryoprotectant solution is between about 100 nM and about 250 nM, between about 250 nM and about 500 nM, between about 500 nM and about 750 nM, between about 750 nM and about 1 μM, between about 1 μM and about 5 μM, between about 5 μM and about 25 μM, between about 25 μM and about 50 μM, between about 50 μM and about 100 μM, between about 100 μM and about 250 μM, between about 250 μM and about 500 μM, between about 500 μM and about 750 μM, between about 750 μM and about 1 mM, between about 1 mM and about 10 mM, between about 10 mM and about 50 mM, between about 50 mM and about 100 mM, between about 100 mM and about 250 mM, between about 250 mM and about 500 mM, between about 500 mM and about 750 mM, or between about 750 mM and about 1,000 mM. In some embodiments, the concentration of the peptoid polymer and/or salt thereof and/or peptoid-peptide hybrid and/or salt thereof in the cryoprotectant solution is about 100 nM, about 1 μM, about 10 μM, about 100 μM, about 1 mM, about 10 mM, about 100 mM, or about 1,000 mM. In particular embodiments, the concentration of the peptoid polymer and/or salt thereof and/or peptoid-peptide hybrid and/or salt thereof in the cryoprotectant solution is about 1, 2, 3, 4, 5, 6, 7, 8, 9, 10, 20, 30, 40, 50, 60, 70, 80, 90, or 100 mM.

In other aspects, provided herein is a method for preserving a biological sample. In particular embodiments, the biological sample possesses cellular composition. In some embodiments, the biological sample comprises a tissue. In other embodiments, the biological sample comprises an organ. In still other embodiments, the biological sample comprises a cell. In particular embodiments, the biological sample comprises one or more tissues, one or more organs, one or more cells, or a combination thereof. In some embodiments, the method comprises contacting the biological sample with a peptoid polymer and/or a salt thereof described herein, a peptoid-peptide hybrid and/or a salt thereof described herein, a cryoprotectant solution described herein, or a combination thereof. In some instances, when a combination of compositions or solutions is used, contacting the biological sample with the compositions or solutions can be accomplished in multiple steps. As a non-limiting example, a biological sample can first be contacted with a peptoid polymer and/or a salt thereof described herein, and then at a later point the biological sample can be contacted with a cryoprotection solution described herein.

In particular instances, the tissue is a bioengineered tissue. In some instances, the biological sample is selected from the group consisting of heart, liver, lung, kidney, pancreas, intestine, thymus, cornea, nerve cells, blood platelets, genitourinary cells (e.g., sperm cells, oocytes, corpus cavernosum cells (e.g., smooth muscle corpus cavernosum cells, epithelial corpus cavernosum cells), urinary bladder cells, urethral cells, ureter cells, kidney cells, testicular cells), embryonic cells, stem cells, bone cells, primary cells, and a combination thereof.

Cryoprotection of biological samples is useful for any number of purposes. Non-limiting examples include organoid preservation, primary cell preservation, stem cell preservation (e.g., hematopoietic stem cells, embryonic stem (ES) cells, pluripotent stem cells (PSCs), and induced pluripotent stem cells (iPSCs)), preservation of adult cells and cell lines (e.g., lymphocytes, granulocytes, immune system cells, bone cells), preservation of embryos, sperm, and oocytes, tissue preservation, and organ preservation. Preservation of tissues, organs, and other biological samples and structures is especially useful, for example, in the field of organ transplantation. Other useful applications of the present invention to biological sample cryoprotection will readily be known to one of skill in the art.

In yet other aspects, provided herein is a method for preserving one or more biological macromolecules. Said biological macromolecules can be naturally or unnaturally occurring. Non-limiting examples of biological macromolecules that are suitable for cryoprotection by compositions and methods of the present invention include nucleic acids (e.g., DNA, RNA), amino acids, proteins, peptides, lipids, and composite structures (e.g., liposomes). In some embodiments, the method comprises contacting the biological macromolecule with a peptoid polymer and/or a salt thereof described herein, a peptoid-peptide hybrid and/or a salt thereof described herein, a cryoprotectant solution described herein, or a combination thereof. In some instances, the biological macromolecule is an isolated protein. In particular instances, the isolated protein is a protease protein. In some instances, when a combination of compositions or solutions is used, contacting the one or more biological macromolecules with the compositions or solutions can be accomplished in multiple steps. As a non-limiting example, the one or more biological macromolecules can first be contacted with a peptoid polymer and/or a salt thereof described herein, and then at a later point the biological sample can be contacted with a cryoprotection solution described herein.

Cryoprotection of biological macromolecules using compositions and methods of the present invention is useful for any number of purposes. Non-limiting examples of such purposes include the preservation of DNA (e.g., genomic DNA) and RNA samples, the preservation of stem cell growth factors, and the preservation of antibodies. Other useful purposes and applications appropriate for compositions and methods of the present invention will be readily known by one of skill in the art.

In particular embodiments, the isolated protein has been crystallized. Crystal cryoprotection has become an essential tool in the repertoire of crystallographic methods for studying biological macromolecules (e.g., proteins and peptides). In many cases, cryoprotection and subsequent data collection at cryogenic temperature are essential for obtaining a complete data set by overcoming the problem of radiation damage from the x-ray beam line. Moreover, cryomethods allow crystallographers to work with small crystals, and such methods have become an ideal method to perform long term storage of the crystals without losing diffraction quality. Cryoprotectants provide a means to protect macromolecular crystals from the damaging effects of ice formation during the cryocooling process. Cryoprotection usually involves immersing the crystal in a solution that forms an amorphous glass (i.e., vitrification) while being flash cooled in liquid nitrogen. The ideal cryoprotectants for crystallography should be hypereffective (i.e., the cryoprotectants achieve an effective result at a low concentration). Currently available cryoprotectants are not hypereffective. Therefore, if the cryoprotectant concentration is too low, crystalline ice will form during the experiment which leads to background interference. If the cryoprotectant concentration is too high, the immediate melting down of the crystal structure can result from beam energy, resulting in low quality data affecting subsequent structure analysis. For example, current state of the art cryoprotectant solutions used in x-ray crystallography applications require the use of 20% ethylene glycol to prevent ice crystal formation at crystalized protein storage temperatures. During x-ray data collection, the ethylene glycol heats and dissolves the crystals preventing further data collection. For additional information, see, e.g., Garman et al. *J. Appl. Cryst.* 30:211 (1997).

In some embodiments, a peptoid polymer and/or salt thereof described herein, peptoid-peptide hybrid and/or salt thereof described herein, cryoprotectant solution described herein, or a combination thereof decreases crystal dissolving during x-ray data collection. In some embodiments, the peptoid polymer and/or salt thereof, peptoid-peptide hybrid and/or salt thereof, cryoprotectant solution, or combination thereof lowers background scattering.

Biological samples and macromolecules that are suitable for cryoprotection according to the compositions and methods of the present invention can come from any biological kingdom (e.g., Animalia (including but not limited to humans and livestock animals), Plantae, Fungi (including but not limited to mushrooms), Protista, Archaea/Archaeabacteria, and Bacteria/Eubacteria).

In another aspect, the present invention provides a cosmetic care product. In some embodiments, the cosmetic care product comprises a peptoid polymer and/or a salt thereof described herein, a peptoid-peptide hybrid and/or a salt thereof described herein, a cryoprotectant solution described herein, or a combination thereof. In some embodiments, the cosmetic care product is a skin care product. In some embodiments the skin care product is topically applied. Typical formulations for topical products include creams, serums, ointments, sprays, lotions, and patches.

In another aspect, the present invention provides an antifreeze product such as a deicing or ice inhibiting product. In some embodiments, the antifreeze product comprises a peptoid polymer and/or a salt thereof described herein, a peptoid-peptide hybrid and/or a salt thereof described herein, a cryoprotectant solution described herein, or a combination thereof. In some embodiments, the antifreeze product is used to prevent, inhibit, or delay the formation of ice on or within objects including, but not limited to, general mechanical and electrical equipment. In some embodiments, the antifreeze product prevents, inhibits, or delays the formation of ice on or within aircraft or parts thereof, drones, cables, automobiles or parts thereof (e.g., car engines), gear systems, brake systems, windows, sprinkler systems, gas pipelines, or electrical cables (e.g., including power lines). In other instances, the antifreeze product acts as a kinetic hydrate inhibitor. In some embodiments the antifreeze product further comprises ethylene glycol, methanol, propylene glycol, glycerol, or combinations thereof.

In another aspect, the present invention provides a frozen food product. In some embodiments the frozen food product comprises a peptoid polymer and/or a salt thereof described herein, a peptoid-peptide hybrid and/or a salt thereof described herein, a cryoprotectant solution described herein, or a combination thereof. In some embodiments, the frozen food product is selected from the group consisting of ice cream, yogurt, seafood, fruit, and meat products. In some embodiments the frozen food product further comprises propylene glycol.

E. Cryopreservation Protocols

The compositions and methods described herein are suitable for use in any number of cryopreservation protocols. As a non-limiting example, compositions and methods of the present invention are useful for cryopreservation during supercooling to high sub-zero temperatures (e.g., 0° C. to −20° C.). In the field of organ transplantation, organs are typically cooled on ice (e.g., to 0-4° C.), which limits the transplantation window to about ten hours. By using ex vivo machine perfusion with cryoprotectants containing standard small molecule CPAs, it has been possible to preserve organs for up to 96 hours at a temperature of −6° C. While it is desirable to further reduce the cryopreservation temperature below −6° C., which would extend the possible cryopreservation time, it has not been possible to do so because the high concentrations of standard CPAs necessary to further reduce the temperature result in irreversible organ damage owing to CPA-related toxicity. For more information, see, e.g., Uygun K, et. al. *Nat. Protoc.* 10(3):484-94 (2015). Employing ex vivo perfusion methods or otherwise contacting biological samples (e.g., organs and tissues) or macromolecules with peptoid polymers and/or salts thereof, peptoid-peptide hybrids and/or salts thereof, and/or cryoprotectant solutions described herein is useful for supercooling to high sub-zero temperatures, allowing cryopreservation for longer periods of time and at lower temperatures than is currently feasible. Other suitable applications of the present invention to high sub-zero temperature supercooling will readily be known to one of skill in the art.

As another non-limiting example, compositions and methods of the present invention are useful for cryopreservation during freezing protocols (e.g., −20° C. to −196° C.). Freezing protocols are typically performed at a controlled rate (sometimes referred to as slow freezing) during at least part of the temperature reduction. For example, a biological sample or macromolecule can be contacted with a peptoid polymer and/or a salt thereof described herein, a peptoid-peptide hybrid and/or salt thereof described herein, and/or cryoprotectant solution described herein, and the temperature can be reduced at a controlled rate (e.g., lowered at a rate of 1° C. per minute) until the desired temperature is reached. Alternatively, the temperature can be reduced at a controlled rate until a desired temperature is reached (e.g., between −80° C. and −180° C.), and then the sample or macromolecule can be flash frozen (e.g., by immersing the sample or macromolecule in liquid nitrogen or placing the sample or macromolecule above liquid nitrogen). The peptoid polymer and/or salt thereof, peptoid-peptide hybrid and/or salt thereof, and/or cryoprotectant solution can be contacted with the sample or macromolecule being cryopreserved at any point during the protocol, as long as it is before the formation of ice crystals that damage the sample or macromolecule being preserved.

As yet another non-limiting example, compositions and methods of the present invention are useful for cryogenic freezing protocols (e.g., −90° C. to −196° C.). For example, a biological sample or macromolecule can be contacted with a peptoid polymer and/or a salt thereof described herein, a peptoid-peptide hybrid and/or a salt thereof described herein, and/or a cryoprotectant solution described herein, then plunged into liquid nitrogen or a stream of liquid nitrogen vapor in order to quickly freeze the sample without the formation of ice crystals. No ice lattice exists and so the water within the sample or macromolecule is in an amorphous or glass-like state. Therefore, damaging ice is not formed.

One of skill in the art will readily appreciate that the concentrations and compositions of the peptoid polymers, peptoid polymer salts, peptoid-peptide hybrids, peptoid-peptide hybrid salts, and cryoprotectant solutions described herein can be modified depending on the particular biological sample and/or macromolecule being cryopreserved and the particular cryopreservation protocol being employed.

F. Methods of Screening

In a related aspect, the present invention provides methods for screening peptoid polymers and/or salts thereof, peptoid-peptide hybrids and/or salts thereof, and/or cryoprotectant solutions for activity.

In one embodiment, the peptoid polymer and/or salt thereof, peptoid-peptide hybrid and/or salt thereof, and/or cryoprotectant solution is screened for lowering the freezing point of water using a polarized light microscope to detect ice crystal formation. Polarized light microscopy is an optical microscopy technique that uses polarized light as the light source. Image contrast arises from the interaction of plane-polarized light with a birefringent (or doubly-refracting) species to produce two individual wave components that are each polarized in mutually perpendicular planes. The velocities of these components, which are termed the ordinary and the extraordinary wavefronts, are different and vary with the propagation direction through the specimen. After exiting the specimen, the light components become out of phase, but are recombined with constructive and destructive interference when they pass through the analyzer. This interference creates a detectable contrast in the sample. Ice crystal formation is easily detected using this technique because ice crystals are birefringent species. In a standard experiment, samples comprising the peptoid polymer and/or salt thereof, peptoid-peptide hybrid and/or salt thereof, and/or cryoprotectant solution are cooled to a desired temperature for a desired amount of time. One or more samples, while at the desired temperature, are placed under the polarized light microscope and visually inspected for formation of ice crystals.

In one embodiment, the peptoid polymer and/or salt thereof, peptoid-peptide hybrid and/or salt thereof, and/or cryoprotectant solution is screened for lowering the freezing point of an aqueous solution using differential scanning calorimetry to quantitate thermal hysteresis activity. Differential scanning calorimetry is a thermoanalytical technique in which the difference in the amount of heat required to increase the temperature of a sample and reference is measured as a function of temperature. When a physical transformation such as phase transition occurs, more or less heat will need to flow to the sample than the reference to maintain both at the same temperature. The difference in temperature between the phase transition of the reference and the sample reports on the sample's ability to reduce or inhibit ice crystal formation at sub 0° C. temperatures. In a standard experiment, a sample comprising the peptoid polymer and/or salt thereof, peptoid-peptide hybrid and/or salt thereof, and/or cryoprotectant solution is compared to a reference that lacks the peptoid polymer and/or salt thereof, peptoid-peptide hybrid and/or salt thereof, and/or cryoprotectant solution.

G. Cell Viability Assays to Test for Activity

In a related aspect, the present invention provides cell viability assays to test for the ability of a peptoid polymer and/or a salt thereof of the present invention, a peptoid-peptide hybrid and/or salt thereof of the present invention, and/or a cryoprotectant solution of the present invention to maintain cell viability (e.g., after storage) at reduced temperatures.

In some embodiments, cell viability is tested using the alamarBlue® Cell Viability Assay Protocol provided by Thermo Fisher Scientific, Inc. Briefly, alamarBlue® is the trade name of resazurin (7-Hydroxy-3H-phenoxazin-3-one 10-oxide) which is a non-toxic cell permeable compound that is blue in color and virtually non-fluorescent. Upon entering cells, resazurin is reduced to resorufin, a compound that is red in color and highly fluorescent. Viable cells continuously convert resazurin to resorufin, increasing the overall fluorescence and color of the media surrounding cells. Non-viable cells do not convert resazurin to resorufin; thus the overall fluorescence and color of the media surrounding the cells is an indication of the relative amount of viable cells in the sample. In a standard experiment, cells and the peptoid polymer and/or salt thereof, peptoid-peptide hybrid and/or salt thereof, and/or cryoprotectant solution are mixed in any suitable container. The mixture is then cooled to the desired sub 0° C. temperature and held for the desired amount of time. Cells are then returned to ambient temperatures and the almarBlue® reagent is added, incubated, and measured following the Thermo Fisher protocol. Typically, direct readout of cell viability is determined by measuring the relative fluorescence of the samples at the wavelengths $\lambda_{Ex}$~560 nm $\lambda_{Em}$~590 nm.

In some embodiments, cell viability is tested using the LIVE/DEAD© Viability/Cytotoxicity Kit, for mammal cells provided by Thermo Fisher Scientific, Inc. This kit uses two indicator molecules: calcein AM and Ethidium homodoimer-1 (EthD-1). Live cells are distinguished by the presence of ubiquitous intracellular esterase activity, determined by the enzymatic conversion of the virtually nonfluorescent cell-permeant calcein AM to the intensely fluorescent calcein. The polyanionic dye calcein is well retained within live cells, producing an intense uniform green fluorescence in live cells ($\lambda_{Ex}$~495 nm $\lambda_{Ex}$~515 nm). Conversely, EthD-1 enters cells with damaged membranes and undergoes a 40-fold enhancement of fluorescence upon binding to nucleic acids, thereby producing a bright red fluorescence in dead cells ($\lambda_{Ex}$~495 nm $\lambda_{Em}$~635 nm). Notably, EthD-1 is excluded by the intact plasma membrane of live cells, so the determination of live and dead cells is easily distinguishable. Calcein and EthD-1 can be viewed simultaneously with a conventional fluorescein longpass filter. Alternatively, the fluorescence from these dyes may also be observed separately; calcein can be viewed with a standard fluorescein bandpass filter, and EthD-1 can be viewed with filters for propidium iodide or Texas Red® dye. In a standard experiment, cells and the peptoid polymer and/or salt thereof, peptoid-peptide hybrid and/or salt thereof, and/or cryoprotectant solution are mixed in any suitable container. The mixture is then cooled to the desired sub 0° C. temperature, held at that temperature for the desired amount of time, and then returned to ambient temperatures. Subsequent steps involving the addition of the calcein AM and EthD-1 reagents and measuring the assay results are performed as described in the Thermo Fisher protocol. Typically, direct readout of cell viability is determined by measuring the relative fluorescence at the above indicated wavelengths for both reagents.

In some embodiments, cell viability is tested using the MTT assay. The MTT assay is a colorimetric cell viability and proliferation assay that relies upon the reduction of yellow tetrazolium MTT (3-(4,5-dimethylthiazolyl-2)-2,5-diphenyltetrazolium bromide) to the insoluble formazan, which has a purple color. Tetrazolium dye reduction is dependent on NAD(P)H-dependent oxidoreductase enzymes, primarily located in the cytosolic compartment of metabolically active cells. The MTT assay is available, for example, from ATCC (www.atcc.org) or Sigma-Aldrich (www.sigmaaldrich.com). In a standard experiment, cells and the peptoid polymer and/or salt thereof, peptoid-peptide hybrid and/or salt thereof, and/or cryoprotectant solution are mixed in any suitable container. The mixture is then cooled to the desired sub 0° C. temperature and held for the desired amount of time. Cells are then returned to ambient temperatures and the MTT reagent is added, incubated, and measured following the ATCC or Sigma-Aldrich protocol. Typically, absorbance of converted dye is measured at a wavelength of 570 nm with background subtraction at 630-690 nm.

IV. Examples

The following examples are offered to illustrate, but not to limit, the claimed invention.

Example 1. Peptoid-Mediated Inhibition of Ice Crystal Formation

This example illustrates the ice crystal inhibition properties of N-substituted peptoid polymers and peptoid-peptide hybrids at sub 0° C. temperatures.

Capillary Tube Assays

In this experiment, four water-based samples were prepared in capillary tubes containing MilliQ purified water. One sample contained only water, and another sample contained 160 mM ethylene glycol (EG). The other two samples each contained a peptoid polymer at 9 mM. One of the peptoid polymer samples contained the peptoid polymer called "Compound 1," while the other sample contained the peptoid polymer called "Compound 10." The sequences of the peptoid polymers are as follows:

Compound 1: Nsb-Nsb-Nhp-Nsb-Nsb-Nhp-Nsb-Nsb-Nhp-Nsb;

Compound 10: Nhp-Nhp-Nhp-Nhp-Nhp-Nhp-Nhp-Nhp-Nhp.

The chemical structures for these compounds are provided in Table 2.

Figure 2A:
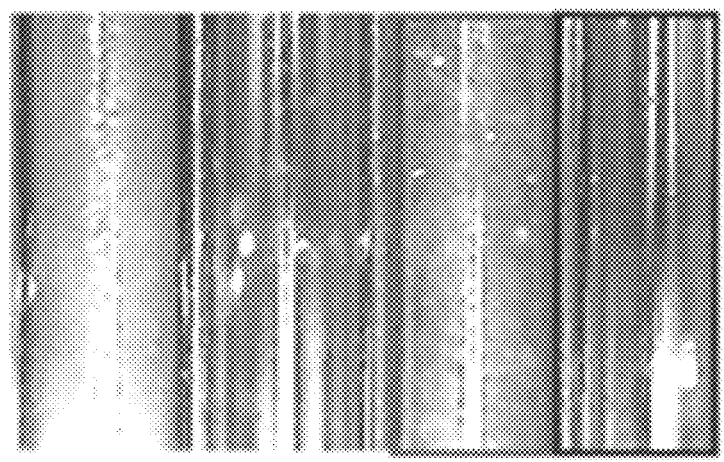
FIGS. 2A and 2B show the results of a capillary tube freeze assay that was performed at −20° C.
Figure 2B:
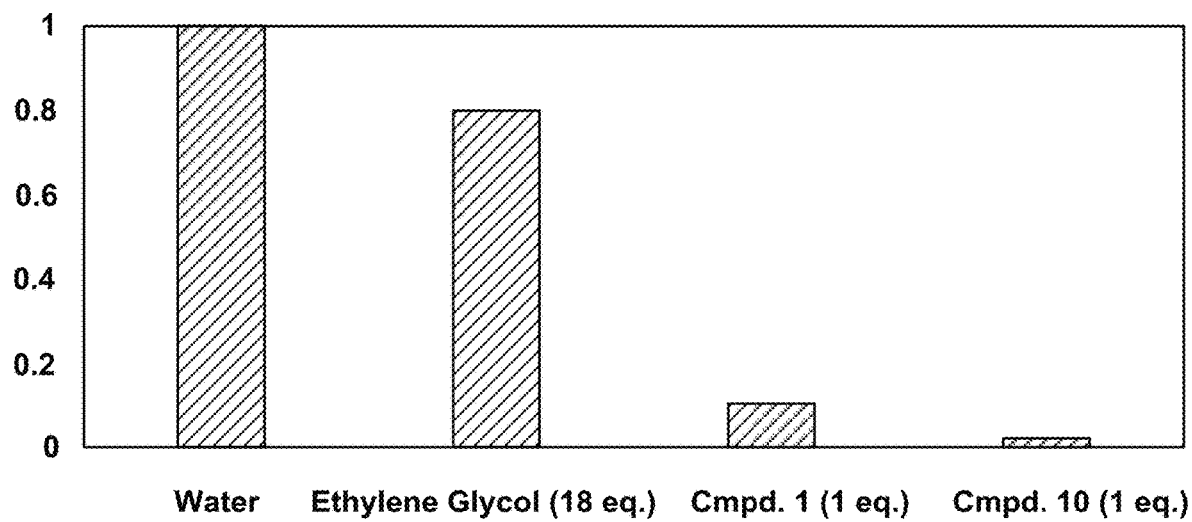
Figure 4E:
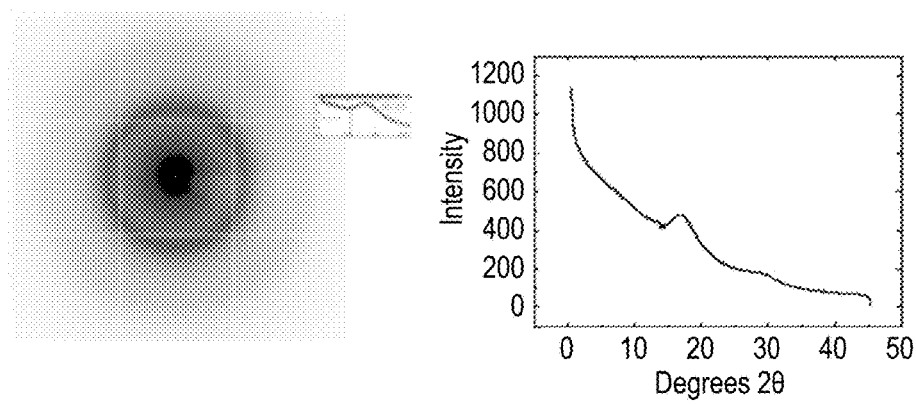
Figure 4F:
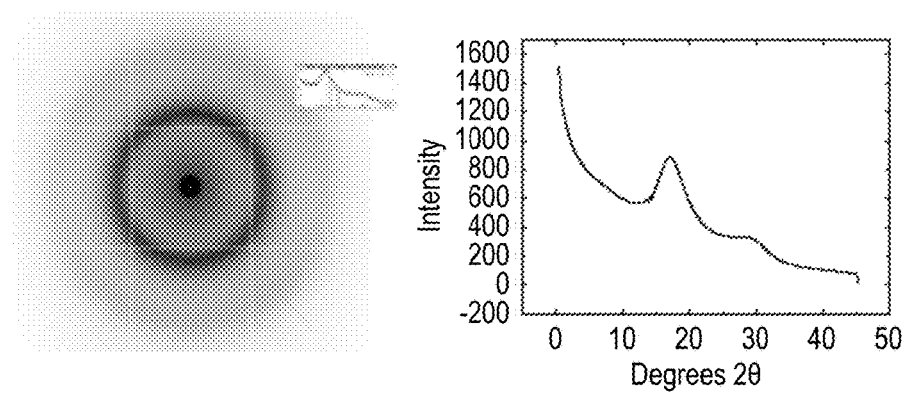
Figure 4G:
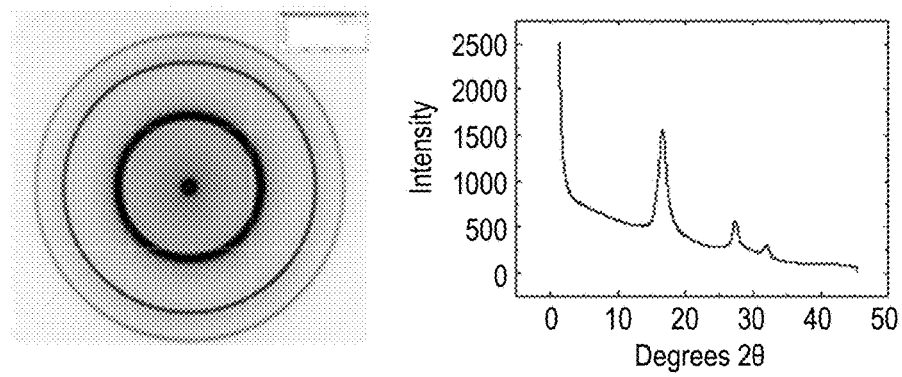

After sample preparation, all samples were slow cooled and incubated at −20° C. on a Peltier cooled plate. After one hour, samples were removed and immediately photographed using a digital camera attached to a 180× Stereo Zoom microscope (FIG. 2A). The water and EG samples showed significant ice crystal formation, although the EG sample showed less ice formation than the water-only sample. In contrast, neither of the samples containing the peptoid polymer compounds exhibited significant ice crystal formation. Normalized data is presented in FIG. 2B. Of note, the EG sample, containing a CPA concentration that was about 18 times higher than the peptoid sample concentrations, still exhibited significant ice formation whereas the peptoid samples did not.

Crystallographic X-Ray Diffraction Assays

In order to increase the throughput of library analysis, a crystallographic x-ray diffraction (XRD) technique was used to evaluate ice crystal formation. For these experiments, the compounds named "Compound 2," "Compound 8," "Compound 10," "Compound 11," "Compound 12," "Compound 13," and "Compound 58" were tested. Compounds 2, 8, 10, 11, 12, and 13 are peptoid polymers, the structures of which are provided in Table 2. Compound 58 is a peptoid-peptide hybrid, the structure of which is provided in Table 10. Compound 58 is similar to Compound 12, except that an arginine amino acid has been appended to the N-terminal end.

For these experiments, EG concentrations between 15% and 30% (v/v) were used. Typically, EG, DMSO, and other cryoprotectants are used during XRD sample analysis at concentrations of 35-40% (v/v) to vitrify solutions and avoid diffraction interference from ice crystals. Concentrations of 1 and 5 mg/mL of the peptoid and peptoid-peptide compounds were used. FIGS. 3A, 3B, and 3C illustrate exemplary XRD data under conditions of complete vitrification, partial vitrification with the presence of cubic ice, and freezing (cubic ice crystals), respectively. XRD data for Compounds 8, 10, 11, 12, 13, and 58 is provided in FIGS. 4A-4G and FIGS. 5A-5G. FIG. 3D provides ice rings scores for a variety of EG concentrations and two concentrations of Compounds 2, 8, and 12.

Several mixtures of the testing solution sample sets showed a strong anti-icing effect. FIG. 3D shows the experimental results of some peptoid polymer solutions compared to EG. "IceRing1" and "IceRing2" refer to ice formation scores, which range between 0 (no ice formation) and 15 (large ice formation). Compounds 2, 12, and 8 and others significantly reduced necessary EG concentrations while preventing ice formation.

The sample containing Compound 12 at a concentration of 5 mg/mL (0.5% (w/v)) and EG at a concentration of 17.5% (v/v) in water was ice-free after flash freezing. This particular mixture was found to completely eliminate all ice formation over multiple trials of flash freezing in a stream of liquid nitrogen vapor (FIG. 3A), and vastly outperformed a standard solution of 30% EG (FIG. 3B). In the figures, black spots and rings represent ice crystals. In comparison to EG at the same molar concentration, this anti-icing effect is 500 times stronger and, without being bound by any particular theory, suggests a non-colligative mechanism for anti-icing, which is the mechanism used by natural antifreeze proteins.

Larger Volume Assays

Figure 6A:
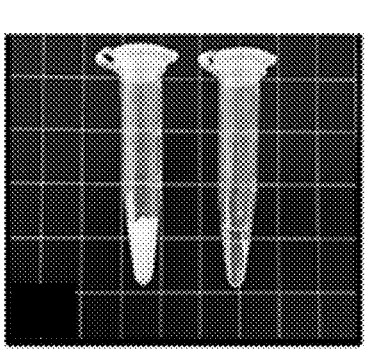
FIGS. 6A-6C show two solutions that were flash frozen, rewarmed, and subsequently refrozen. The control solution contained 22.5% (v/v) ethylene glycol (EG), while the test solution contained 22.5% EG and 5 mg/mL (0.5% (w/v)) Compound 12.
Figure 6B:
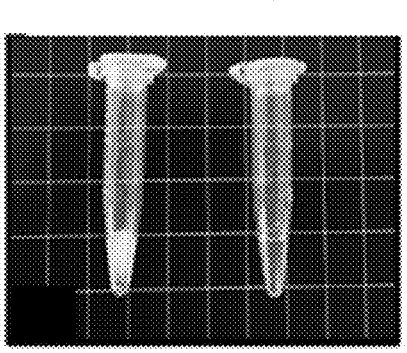

In order to test the usefulness of peptoid polymers at larger scales, experiments were performed using solution volumes that are similar to volumes used for standard egg and stem cell preservation. For these experiments, two samples, one containing 22.5% EG and buffer only, and another containing 22.5% EG and 5 mg/ml (0.5% w/v) of Compound 12 and buffer, were flash frozen in liquid nitrogen. As shown in FIG. 6A, the Compound 12 solution showed complete vitrification with no ice formation immediately after removal from liquid nitrogen, while the control solution had clearly been frozen, yielding a mass of white ice crystals. The rewarming of the solutions in a 37° C. water bath led to an unexpected and beneficial result. The Compound 12 solution bypassed devitrification in less than 2 seconds upon rewarming (FIG. 6B, right), whereas chunks of ice were seen floating in the control sample (FIG. 6B, left) after 20 seconds. Condensation was seen on each of the tubes because the tubes were actually still much below room temperature. This result shows that Compound 12 acts as an active de-icer during thawing.

Figure 6C:
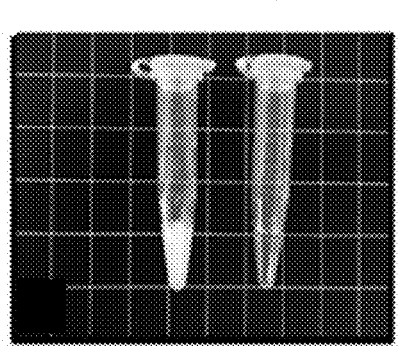

Furthermore, after leaving the 100 μL samples in a −20° C. freezer overnight, the Compound 12 solution was found to be unfrozen (FIG. 6C, right). This result shows that peptoid polymers provide the ability to preserve samples at below 0° C. temperatures for long periods of time without any ice formation. Furthermore, these experiments show that ice-free conditions can be reached with hypothermic cryopreservation, or by the supercooling method, at −20° C. as well as near vitrification to −80° C. by incorporating peptoid polymers to significantly reduce the critical concentration of penetrating CPAs and mitigate cryopreservation toxicity.

As shown here, a formulation of Compound 12 was found to prevent ice formation during vitrification in sub-milliliter volumes. In fact, the solutions were able to remain completely unfrozen at −20° C. and were also able to vitrify when flash frozen at −196° C. Currently, standard human egg cell preservation techniques for in vitro fertilization are limited to solution volumes of less than 5 uL (often 0.5 to 2.5 μL) while using 50% or greater cryoprotectant concentrations. Thus, Compound 12 was able to prevent ice formation in a practical volume, with exceedingly less cryoprotectant, which makes it useful, for example, for preserving human oocytes for in vitro fertilization.

Example 2. Cytotoxicity and Cryopreservation Screening

This example shows that peptoid polymers have little to no cell toxicity and can achieve superior cryopreservation when compared to existing compounds, while reducing the necessary amount of CPAs and thus reducing CPA-associated toxicity.

Cytotoxicity Assays

In order to demonstrate the safety of cryoprotectant compositions, a high-throughput cell-based cytotoxicity assay was developed utilizing the HEK 293 cell line, which is a sturdy and robust stem cell line grown from human embryonic kidney cells in tissue culture.

A Tecan Genesis Robotic Workstation was used to prepare solutions in 96- and 384-well plates. Solutions contained culture media, buffers, a cryoprotectant composition (Compound 12) or DMSO. Solutions were adjusted to the desired pH. Serial dilutions were performed to obtain solutions containing various concentrations of Compound 12 and DMSO. Control experiments were performed using only culture media.

For these experiments, cells were seeded at low density (i.e., 10% confluence), exposed to solutions containing Compound 12 or DMSO, and placed in a 37° C. incubator. The cells were allowed to grow until control cells that were treated only with empty vehicle approached 70% confluence (typically about 3 to 5 days). Assessment for compound cytotoxicity was via MTT assay.

Figure 7:
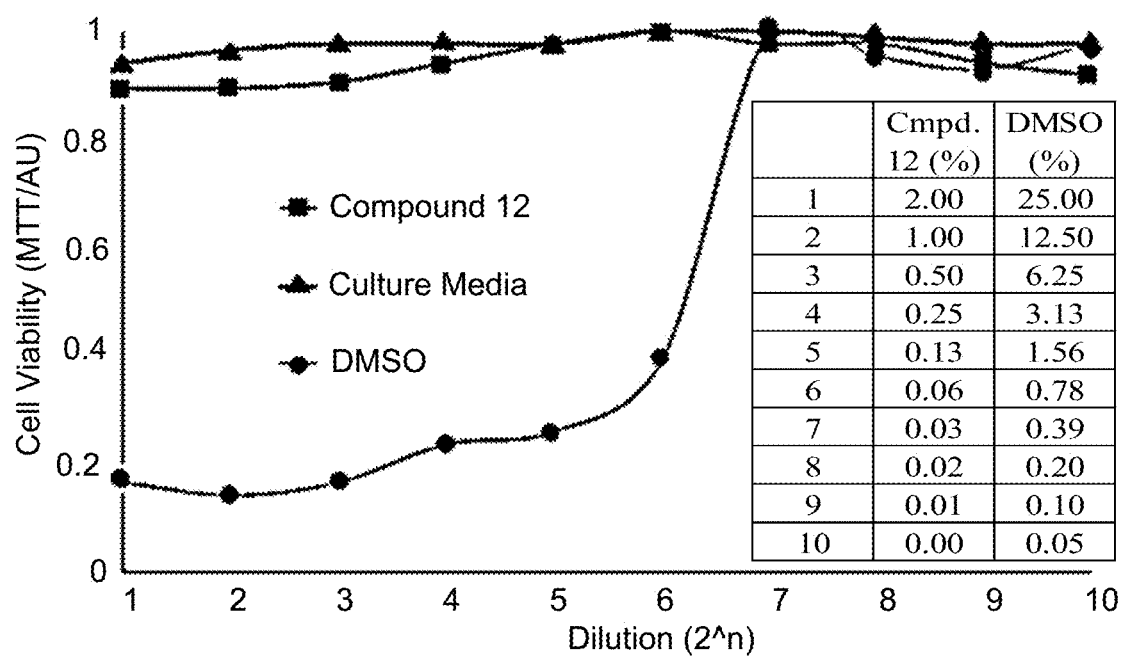
FIG. 7 shows the results of a cell toxicity study performed on HEK 293 cells in which Compound 12 (squares) or DMSO (circles) was added to cell culture media. A sample in which no Compound 12 or DMSO was added ("Culture Media" (triangles)) served as a control. Serial dilutions were performed in order to test different concentrations of Compound 12 and DMSO.

As can be seen in FIG. 7, the toxicity of Compound 12 did not significantly deviate from the that of culture media alone when analyzed by MTT assay. On the other hand, DMSO did not allow for warm survival for an extended period of time at any concentration above 0.5% (v/v). Notably, Compound 12 did not show toxicity at the concentrations in which it can prevent ice formation in a non-biological sample (0.5% w/v) and did not show significant toxicity at concentrations four times greater than this concentration, either.

These results show that cryoprotectant compositions were effective at ice-prevention even at concentrations where DMSO toxicity significantly reduced cell survival.

Cryopreservation Assays

Initial cryopreservation assays were performed using very simple solutions, with and without the addition of Compound 12, in order to minimize confounding outside factors. For this first set of experiments, two sample solutions were prepared. The first sample solution contained simple buffer and ethylene glycol (EG) at a concentration of 22.5% (v/v), and the second sample solution contained simple buffer, EG (22.5% (v/v)), and 5 mg/mL (0.5% (w/v)) of Compound 12.

HEK 293 cells were grown until 70% confluent, then treated with trypsin to remove adhesion proteins and yield free floating cells. Cells were counted using a hemocytometer and sample cell concentrations were adjusted to final concentrations of 10,000 cells per microliter. Cells were then compressed into tight pellets by centrifugation, and each sample was subsequently mixed with 20 μL of one of the sample solutions. Samples were then flash frozen by immersion in liquid nitrogen, followed by rewarming in a 37° C. water bath. After the freeze-thaw process, cells were suspended in a 400× volume of culture media for recovery. The positive control sample was treated with culture media at 37° C. and not subjected to the freeze-thaw process. The negative control sample was treated with culture media only during the freeze-thaw process. After recovery, cells were stained with Calcein AM for 30 minutes and cell viability was measured using a fluorescence plate reader.

Figure 8:
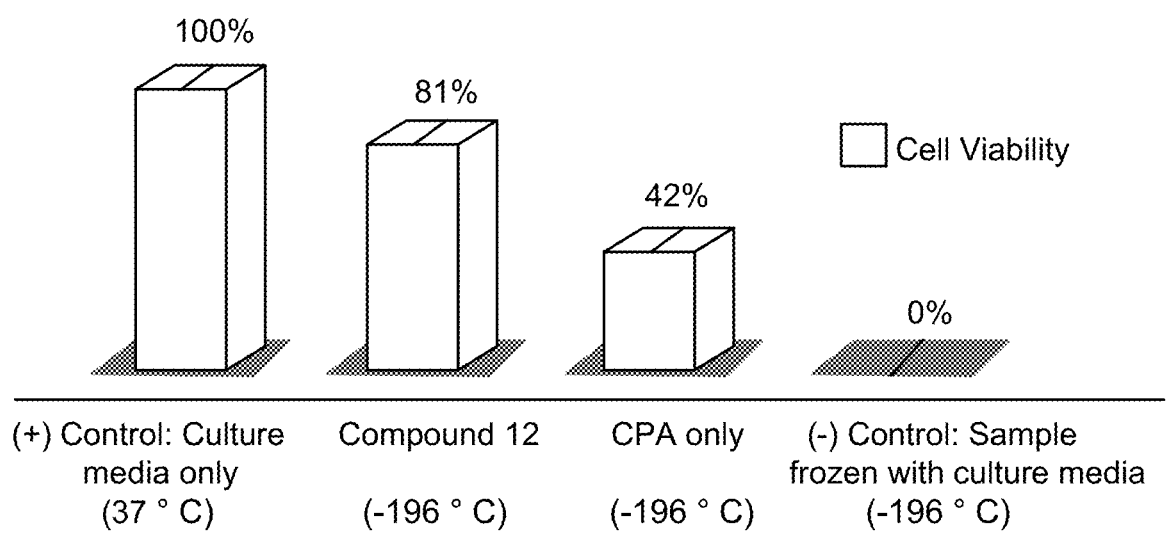
FIG. 8 shows the results of a cryopreservation assay performed on HEK 293 cells, comparing a solution containing ethylene glycol (EG) to a solution containing EG and Compound 12. Cell viability was measured 12 hours post-thaw.

As shown in FIG. 8, the addition of Compound 12 greatly improved cell survival and demonstrated the ability of this compound to cryopreserve cells. It was observed that the sample containing Compound 12 achieved complete vitrification without ice formation during the freezing process. In addition, the process of devitrification was bypassed much more rapidly compared to the sample lacking Compound 12.

Figure 9:
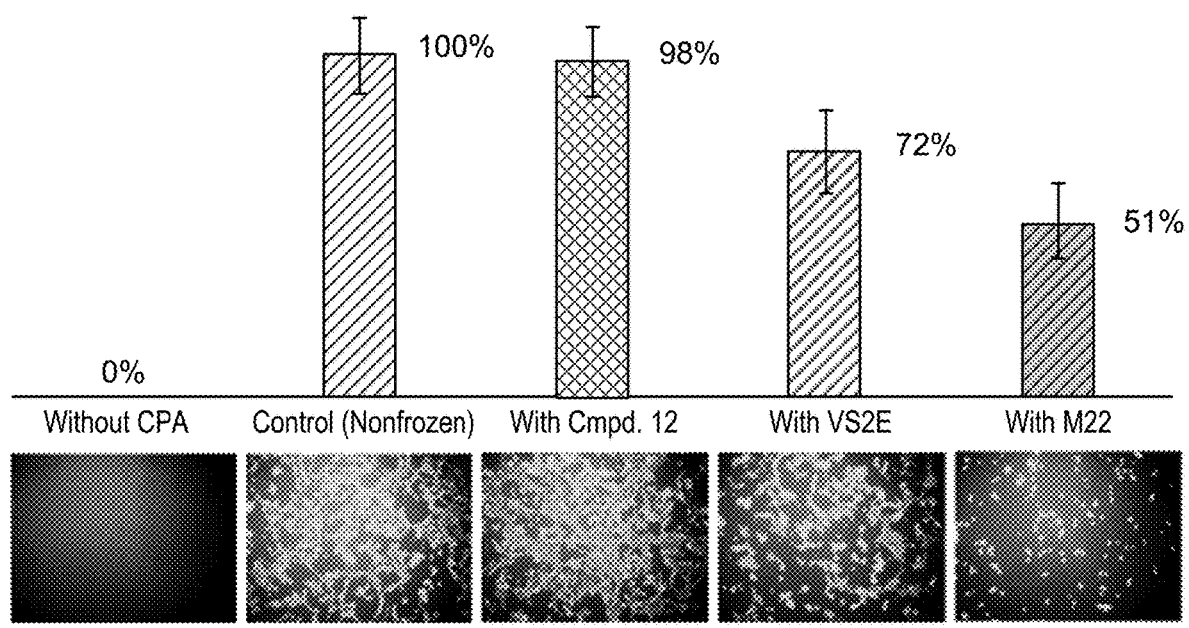
FIG. 9 shows the results of a cryopreservation assay performed on HEK 293 cells, comparing a solution containing 5 mg/mL of Compound 12 plus a mixture of glycols, disaccharides, and a general buffer to solutions containing VS2E or M22. Cell viability was measured 16 hours post-thaw. Cell were vitrified with liquid nitrogen (LN2).

A second set of experiments was performed to evaluate the cryopreservation potential of a formulation that contained 5 mg/mL of Compound 12 plus a mixture of glycols, disaccharides, and a general buffer. Post-thaw survival following vitrification in liquid nitrogen was evaluated as described above. As can be seen in FIG. 9, the formulation achieved near 100% (i.e., 98%) post-thaw survival of the cells, which was similar to the control group that was not exposed to freezing treatment. The cell morphologies and florescence signals looked identical to the non-frozen controls, which indicated that little damage occurred to the cells during the experiment.

As part of the second set of experiments, the cryopreservation potential of the formulation was compared to two known cryopreservation reagents. VS2E is a DMSO-free and serum-free solution containing non-chemically defined polymers (see, e.g., Nishigaki et al. *Int. J. Dev. Biol.* 55:3015-311 (2011)), and M22 is an organ vitrification solution available from 21$^{st}$ Century Medicine. FIG. 9 shows that the formulation containing Compound 12 achieved superior cryopreservation, as cell survival was 72% and 51% for VS2E and M22, respectively. It should be noted that for the M22 sample, background fluorescence may have skewed this result, as a count of live cells in the image suggested that far fewer than 51% of the cells had survived.

The peptoid polymers were highly effective at preventing ice formation in solutions containing significantly reduced ethylene glycol. In particular, low concentrations of the compositions (e.g., 0.5% (w/v)) were sufficient to block ice growth during vitrification and to keep solutions in a liquid, ice-free state on the 20 uL scale, which is a scale that is useful for the preservation of various types of cells.

In summary, these results show that peptoid polymers can achieve superior cryopreservation and reduce the necessary amount of CPAs, thus reducing cell toxicity that is associated with CPAs. The superior properties of the peptoid polymers are especially useful for the treatment of particularly sensitive cell lines and/or when cells need to be cultured for longer time periods.

Example 3. Vitrification Efficacy Assays

As another means of increasing the throughput of library analysis, a vitrification screening assay was performed to evaluate anti-icing efficacy. For these experiments the compounds named "Compound 11," "Compound 12," "Compound 25," "Compound 26," "Compound 27," "Compound 28," "Compound 60," "Compound 62," "Compound 63," "Compound 64," "Compound 69," "Compound 70," "Compound 71," "Compound 72," "Compound 73," "Compound 74," "Compound 75," "Compound 76," "Compound 77," "Compound 78," "Compound 81," "Compound 82," "Compound 83," "Compound 84," and "Compound 85" were tested. Each compound is a peptoid polymer, the structures of which are provided in Tables 2, 5, and 11.

For these experiments, 20 μL samples were flash frozen by liquid immersion in liquid nitrogen. Ethylene glycol (EG) concentrations between 5% and 25% (v/v) were used. A concentration of 5 mg/mL of peptoid polymer compounds were used in formulation. Table 12 lists the lowest concentration of EG necessary to bring about complete vitrification of a 20 μL sample with peptoid polymer in formulation, referred to as the "critical EG concentration." A sample of formulation without the presence of a peptoid polymer was only able to bring about vitrification at 20% or more EG. Peptoid polymers of interest were able to bring about vitrification within formulas containing EG when the concentration of EG was lower than 20%.

Several peptoids were shown to possess a critical EG concentration below 20%, demonstrating their usefulness as anti-icing agents. Compounds 60, 62, 82, 83, 84, and 85 required significantly less EG in order to permit vitrification. Thus, these compounds were able to prevent ice formation in a practical volume, which is useful for the cryopreservation of biological materials.

TABLE 12

| Compound Number | Critical Ethylene Glycol Concentration (v/v) |
| --- | --- |
| 11 | 15.0% |
| 12 | 15.0% |
| 25 | 12.5% |
| 26 | 15.0% |
| 27 | 12.5% |
| 28 | 15.0% |
| 60 | 12.5% |
| 62 | 12.5% |
| 63 | 15.0% |
| 64 | 17.5% |
| 69 | 15.0% |
| 70 | 15.0% |

TABLE 12-continued

| Compound Number | Critical Ethylene Glycol Concentration (v/v) |
|---|---|
| 71 | 17.5% |
| 72 | 17.5% |
| 73 | 20.0% |
| 74 | 15.0% |
| 75 | 15.0% |
| 76 | 15.0% |
| 77 | 15.0% |
| 78 | 15.0% |
| 81 | 15.0% |
| 82 | 12.5% |
| 83 | 10.0% |
| 84 | 12.5% |
| 85 | 10.0% |

Example 4. Cell Viability and Toxicity Assays

This example describes a number of experiments that were performed in order to assess the effects of compositions of the present invention on cell viability, survival, and toxicity.

Figure 10:
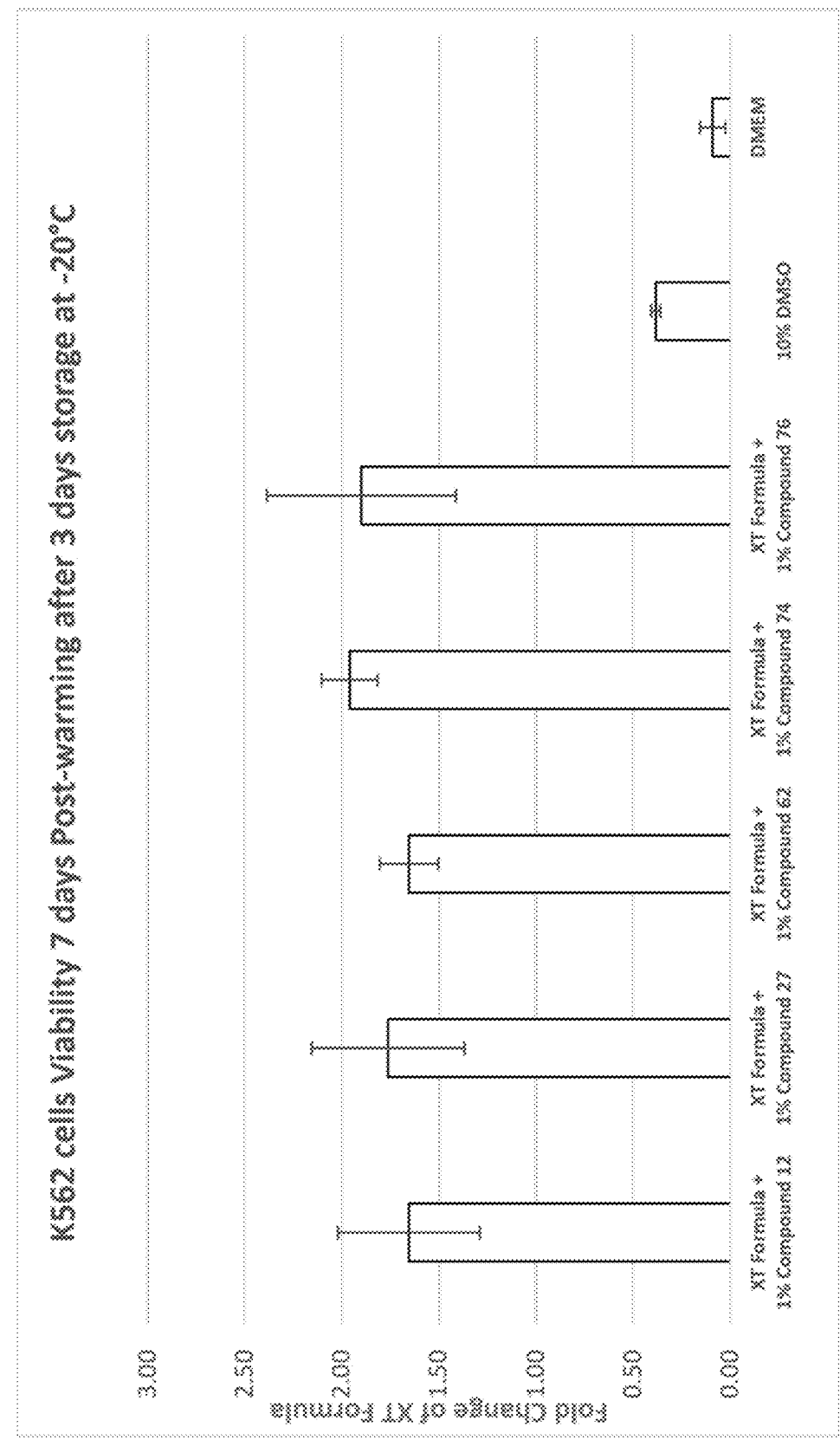
FIG. 10 shows viability data for K562 cells 7 days post-warming after being stored for 3 days at −20° C.

Evaluation of the Effects of Peptoid Polymers on K562 Survival at −20° C. for 3 Days Several compounds were examined in XT Formula at 1% concentration (i.e., 1% peptoid polymer concentration) for their ability to increase the viability of cells subjected to super-cooled storage. XT Formula contains HTK buffer, among other components. In particular, the effects of these compounds on the viability of K562 cells stored at −20° C. for 3 days were evaluated. An Alamar Blue assay was used to assess cell viability 7 days after stored cells were thawed. As shown in FIG. 10, Compounds 12, 27, 62, 74, and 76 improved cell viability compared to XT Formula alone.

Figure 11:
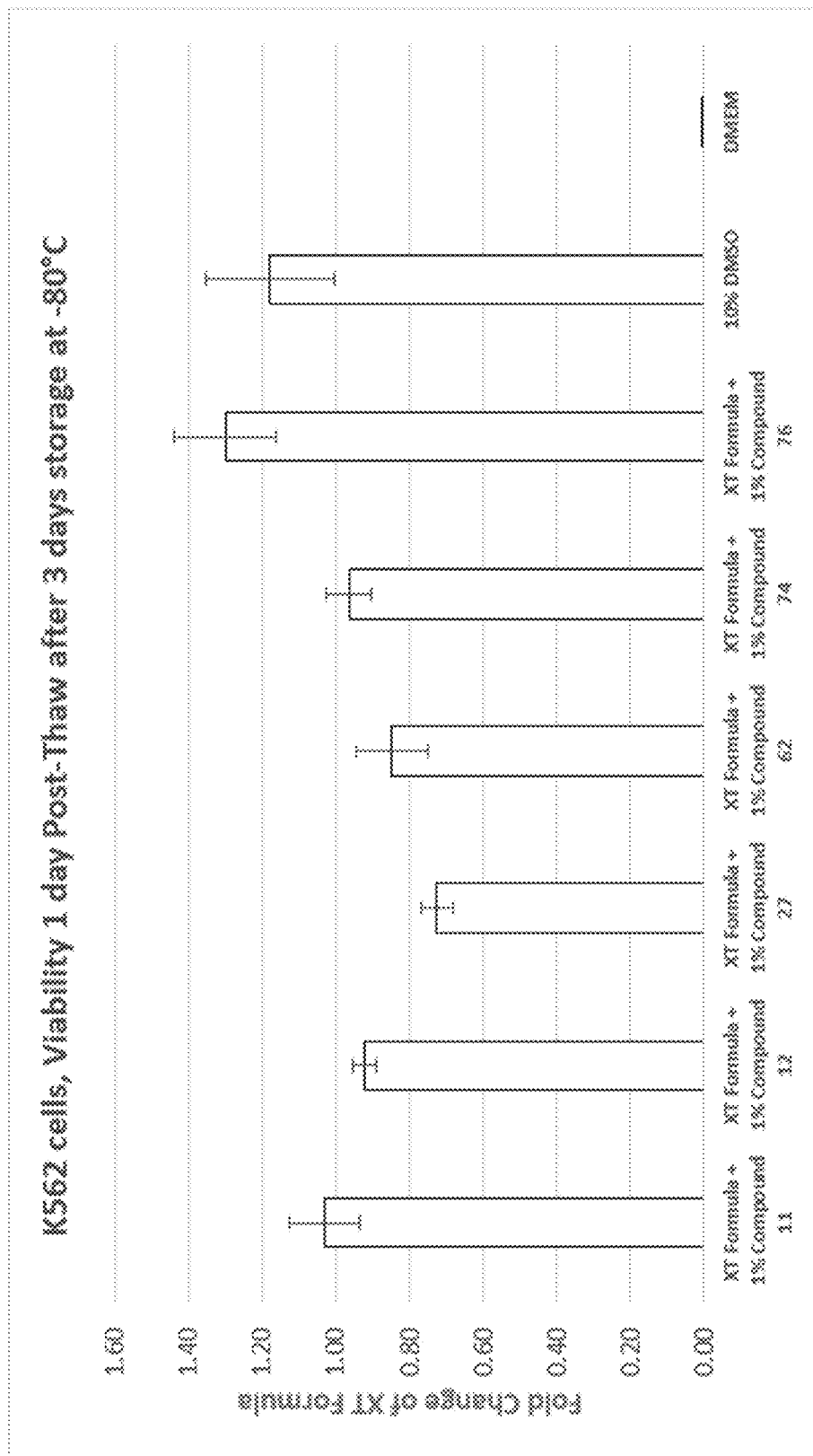
FIG. 11 shows survival data for K562 cells 1 day post-thaw after being stored for 3 days at −80° C.

Evaluation of the Effects of Peptoid Polymers on K562 Survival at −80° C. for 3 Days Several compounds were examined in XT Formula at 1% concentration (i.e., 1% peptoid polymer concentration) for their effects on the cryopreservation of cells. In particular, the effects of these compounds on the survival of K562 cells stored at −80° C. for 3 days were evaluated. An Alamar Blue assay was used to assess cell survival 1 day after stored cells were thawed. A 10% DMSO formula and DMEM cell media only were used as controls. As shown in FIG. 11, Compound 76 produced the greatest improvement in cell survival.

Figure 12:
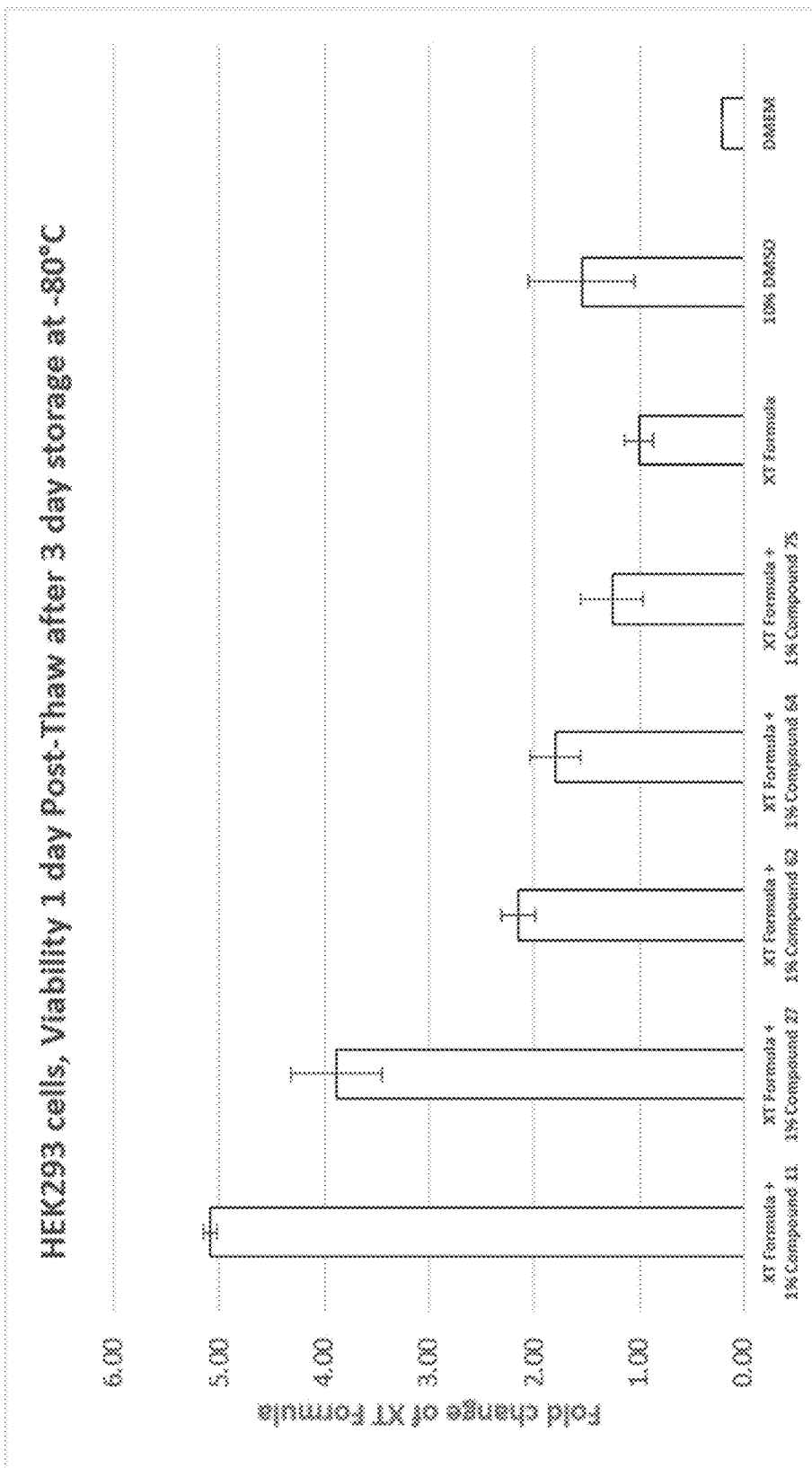
FIG. 12 shows survival data for HEK293 cells 1 day post-thaw after being stored for 3 days at −80° C.

Evaluation of the Effects of Peptoid Polymers on HEK293 Survival at −80° C. for 3 Days Several compounds were examined in XT Formula at 1% concentration (i.e., 1% peptoid polymer concentration) for their effects on the cryopreservation of HEK293 cells, an adherent cell line derived from human embryonic kidney cells. In particular, the effects of these compounds on the survival of HEK293 cells stored at −80° C. for 3 days were evaluated. An Alamar Blue assay was used to assess cell survival 1 day after stored cells were thawed. A 10% DMSO formula and DMEM cell media only were used as controls. As shown in FIG. 12, Compounds 11, 27, 62, 64, and 75 improved cell survival compared to XT Formula alone.

Evaluation of Cytotoxic Effects

Figure 13:
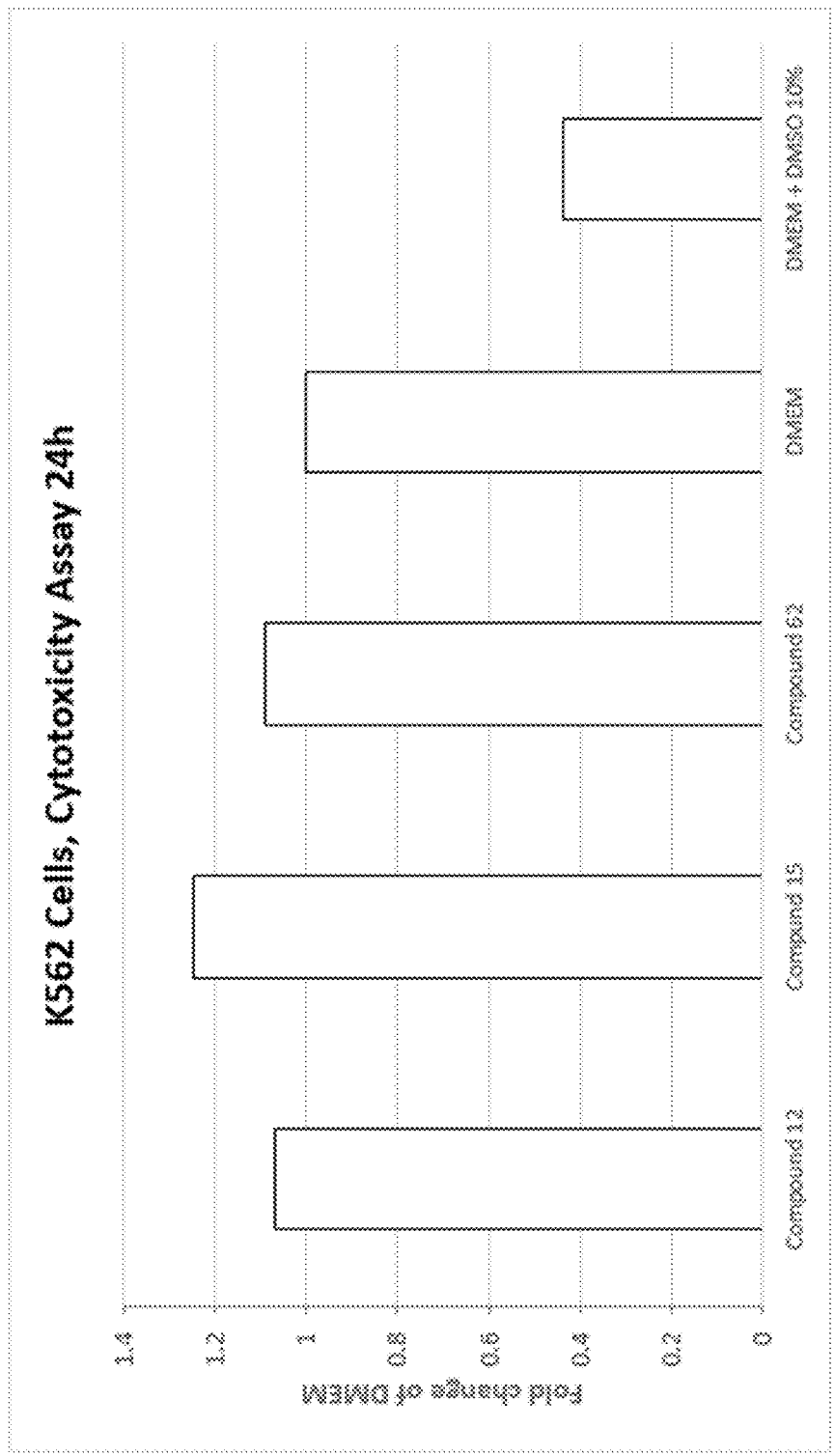
FIG. 13 shows cytotoxicity data for K562 cells.

The cytotoxicity of several compounds were evaluated using a typical cell toxicity assay in K562 cell culture. K562 cells were incubated with peptoid polymers (i.e., Compound 12, 15, or 62, at 1% concentration) for 24 hours at 37° C. and 5% CO$_2$. As a positive control, some cells were incubated without any peptoid polymer (DMEM). For a negative control, cells were incubated with DMSO (DMEM+10% DMSO). As shown in FIG. 13, cells incubated with peptoid polymers persisted about as well as cell incubated in cell culture media alone (DMEM), but cells incubated with DMSO suffered significant toxicity.

TABLE 1

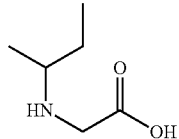

2-(sec-butylamino)acetic acid
Nsb

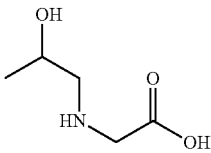

2-((2-hydroxypropyl)amino)acetic acid
Nhp

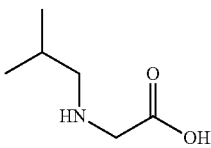

2-(isobutylamino)acetic acid
Nib

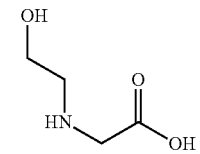

(2-((2-hydroxyethyl)amino)acetic acid
Nhe

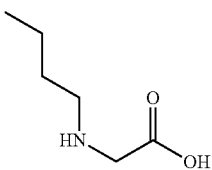

2-(butylamino)acetic acid
Nbu

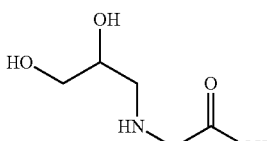

2-((2,3-dihydroxypropyl)amino)acetic acid
Ndp

TABLE 1-continued 2-(propylamino)acetic acid
Npr 2-((1-hydroxypropan-2-yl)amino)acetic acid
Nyp 2-(isopropylamino)acetic acid
Nip 2-((1-(4-hydroxyphenyl)ethyl)amino)acetic acid
Nep 2-(methylamino)acetic acid
Nme 2-((1,3-dihydroxypropan-2-yl)amino)acetic acid
Ndh 2-((3-(2-oxopyrrolidin-1-yl)propyl)amino)acetic acid
Nop 2-(2-methoxyethylamino)acetic acid
Nmo 2-((tetrahydrofuran-2-yl)methylamino)acetic acid
Ntf 2-(furan-2-ylmethyl)amino)acetic acid
Nff 2-(2-methylbutyl)amino)acetic acid
Nmb 2-(R)-(2-hydroxypropylamino)acetic acid
Nrh TABLE 1-continued
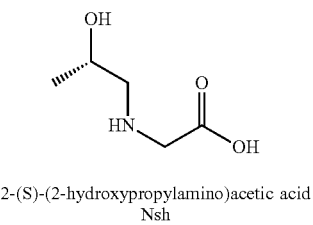
2-(S)-(2-hydroxypropylamino)acetic acid
Nsh
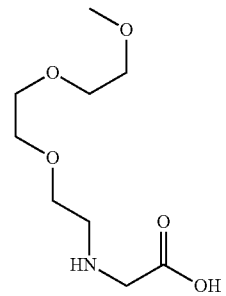
2-(2-(2-(2-methoxyethoxy)ethoxy)ethylamino)acetic acid
N3p
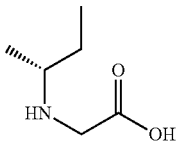
(2-(R)-sec-butylamino)acetic acid
Nbr
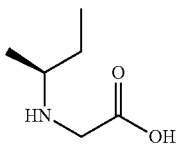
(2-(S)-sec-butylamino)acetic acid
Nbs
TABLE 2
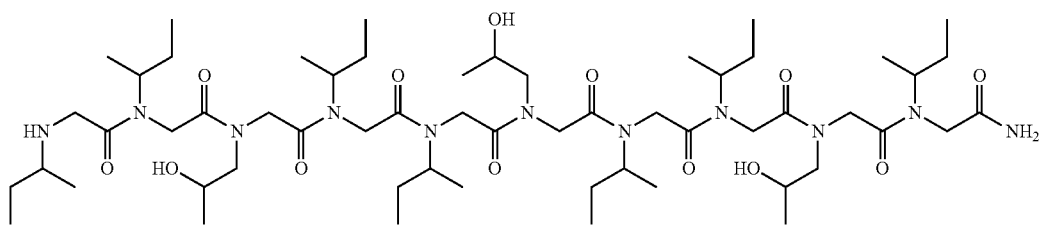 [SMILES: CCC(C)NCC(=O)N(CC(=O)N(CC(=O)N(CC(=O)N(CC(=O)N(CC(=O)N(CC(=O)N(CC(=O)N(CC(=O)N(CC(N)=O)C(C)CC)CC(C)O)C(C)CC)C(C)CC)CC(C)O)C(C)CC)C(C)CC)CC(C)O)C(C)CC]
Compound 1
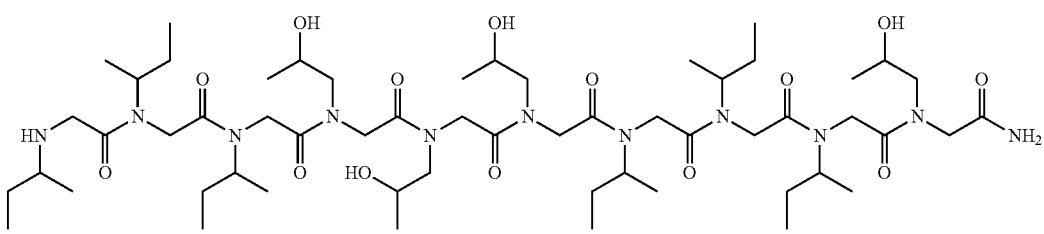 [SMILES: CCC(C)NCC(=O)N(CC(=O)N(CC(=O)N(CC(=O)N(CC(=O)N(CC(=O)N(CC(=O)N(CC(=O)N(CC(=O)N(CC(N)=O)CC(C)O)C(C)CC)C(C)CC)C(C)CC)CC(C)O)CC(C)O)CC(C)O)C(C)CC)C(C)CC]
Compound 2
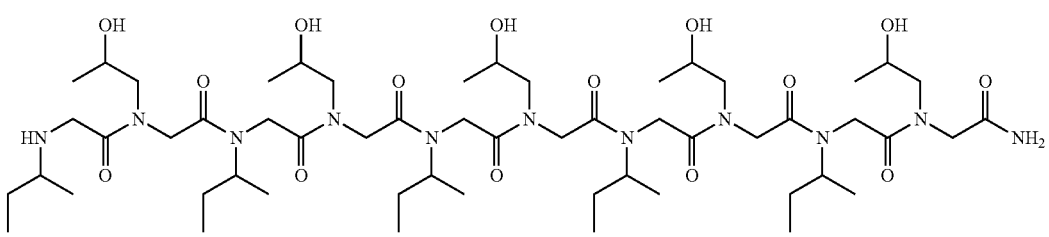 [SMILES: CCC(C)NCC(=O)N(CC(=O)N(CC(=O)N(CC(=O)N(CC(=O)N(CC(=O)N(CC(=O)N(CC(=O)N(CC(=O)N(CC(N)=O)CC(C)O)C(C)CC)CC(C)O)C(C)CC)CC(C)O)C(C)CC)CC(C)O)C(C)CC)CC(C)O]
Compound 3
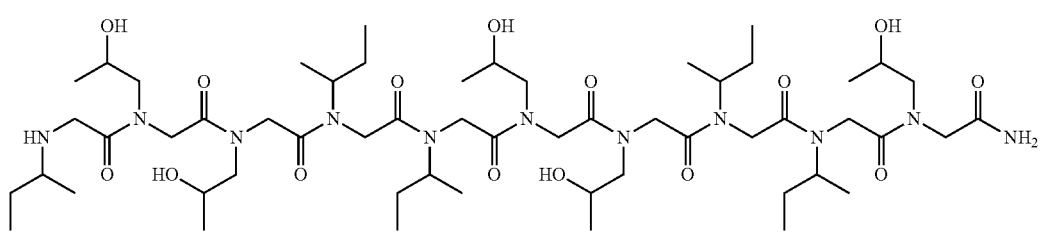 [SMILES: CCC(C)NCC(=O)N(CC(=O)N(CC(=O)N(CC(=O)N(CC(=O)N(CC(=O)N(CC(=O)N(CC(=O)N(CC(=O)N(CC(N)=O)CC(C)O)C(C)CC)C(C)CC)CC(C)O)CC(C)O)C(C)CC)C(C)CC)CC(C)O)CC(C)O]
Compound 4

TABLE 2-continued
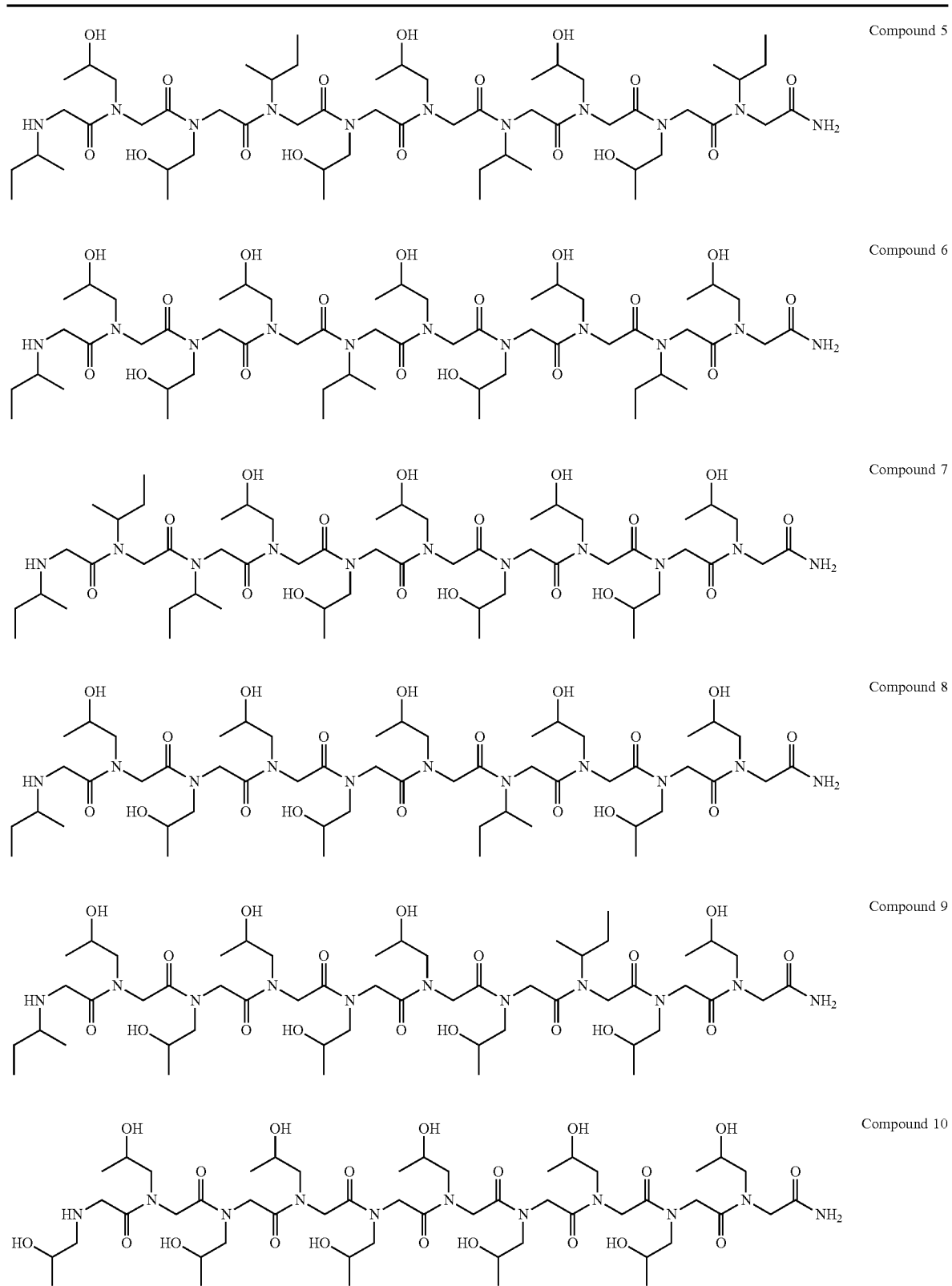
Compound 5
Compound 6
Compound 7
Compound 8
Compound 9
Compound 10

TABLE 2-continued
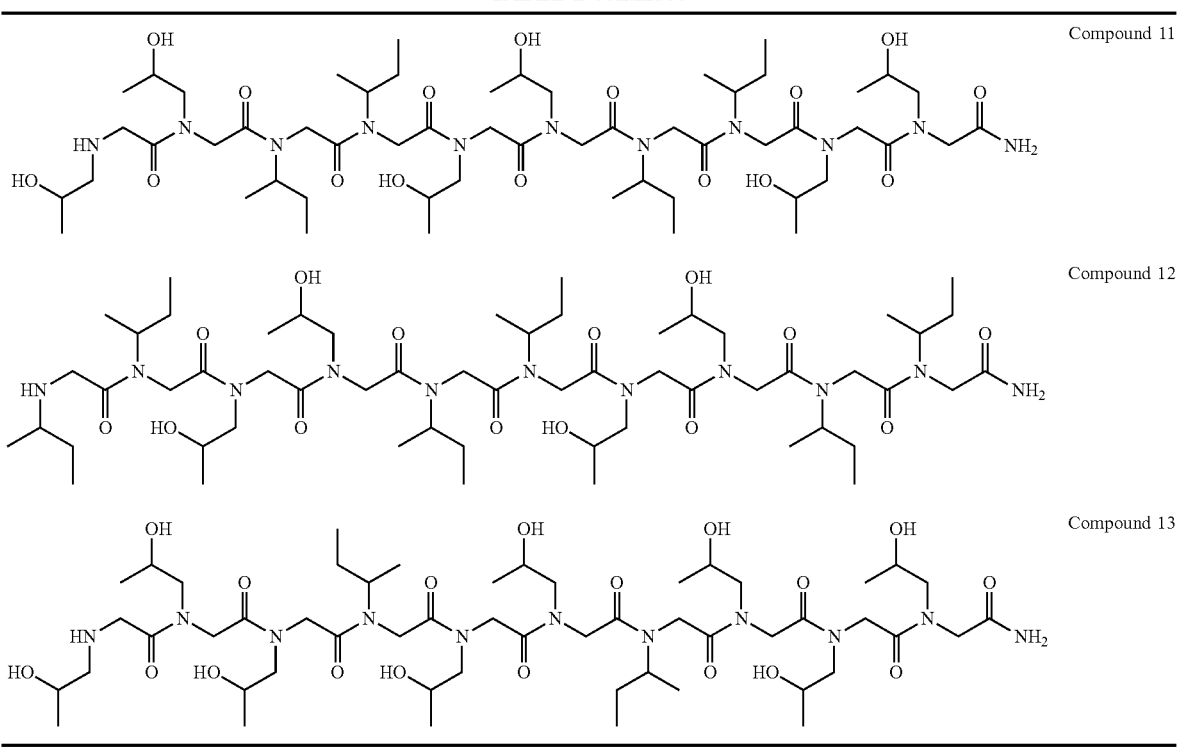
Compound 11
Compound 12
Compound 13
TABLE 3
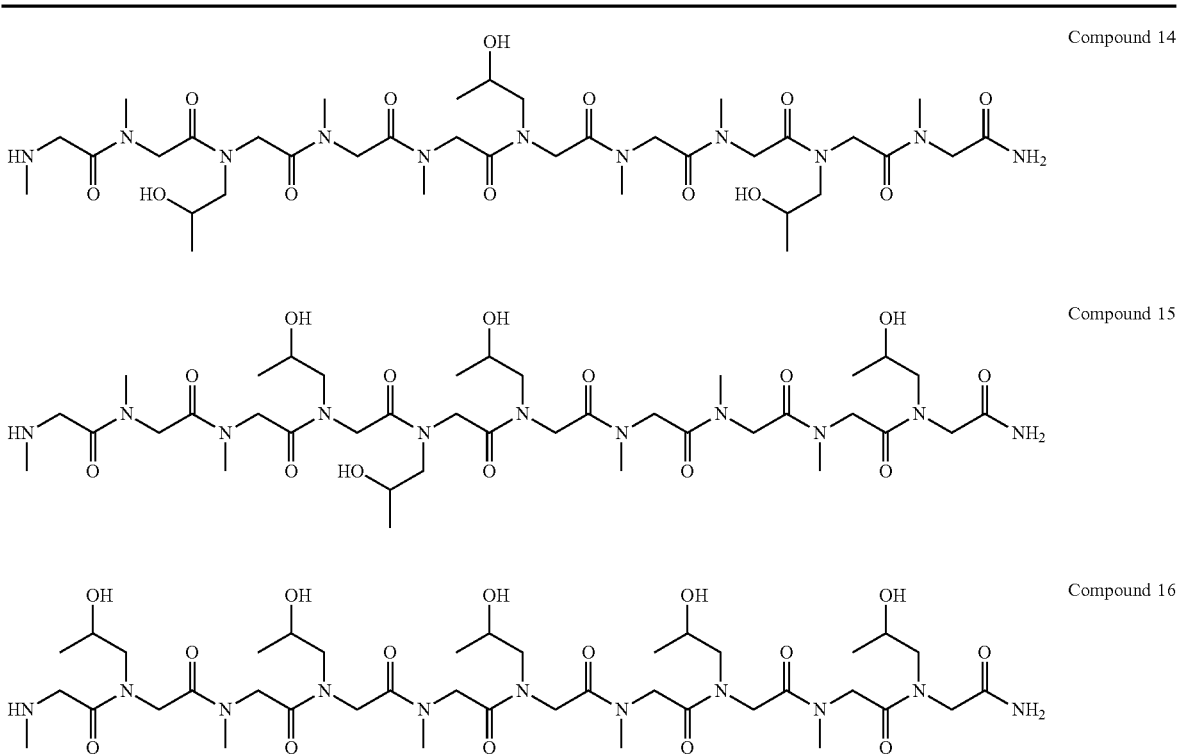
Compound 14
Compound 15
Compound 16

TABLE 3-continued
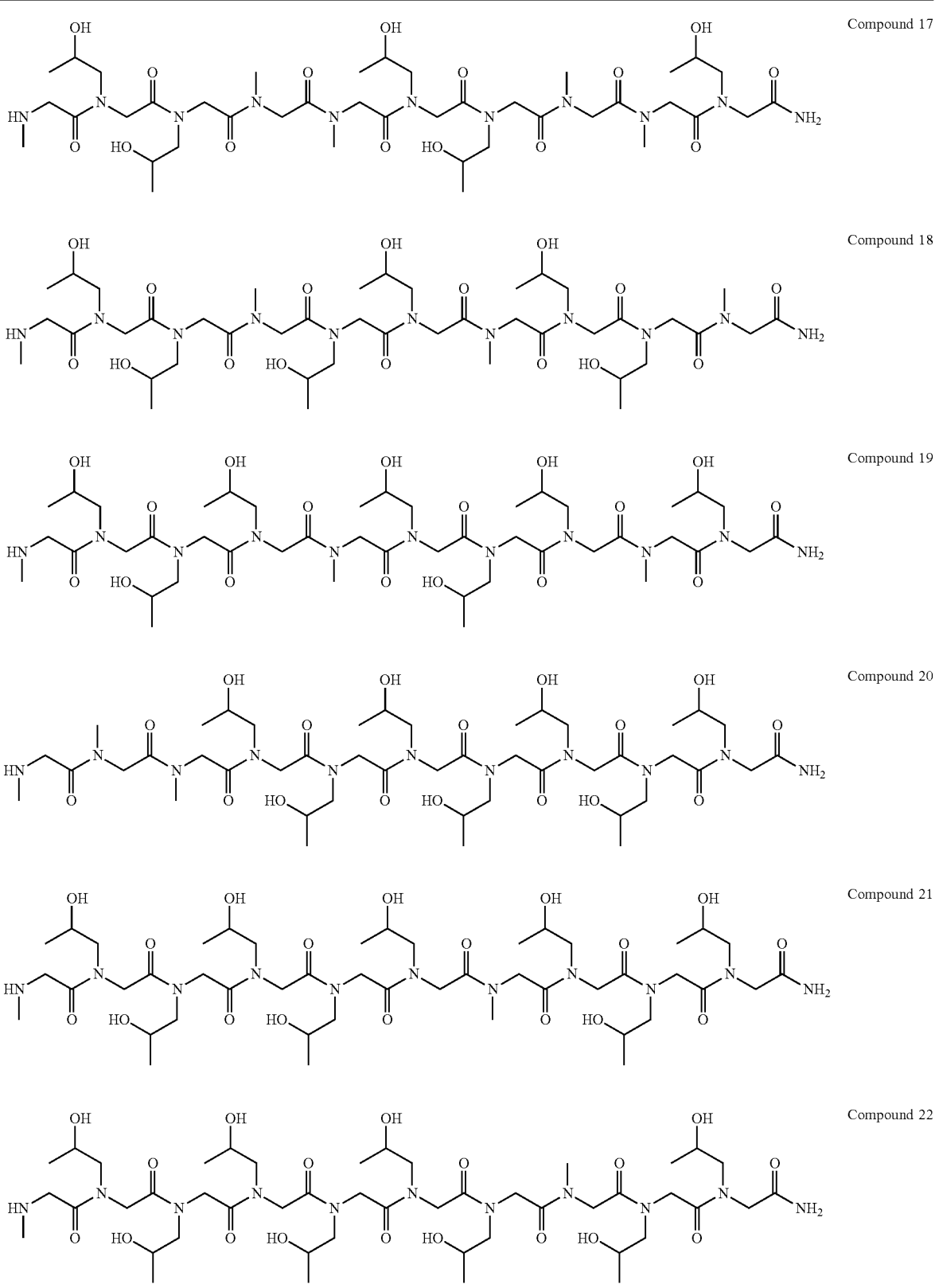
Compound 17
Compound 18
Compound 19
Compound 20
Compound 21
Compound 22

TABLE 4
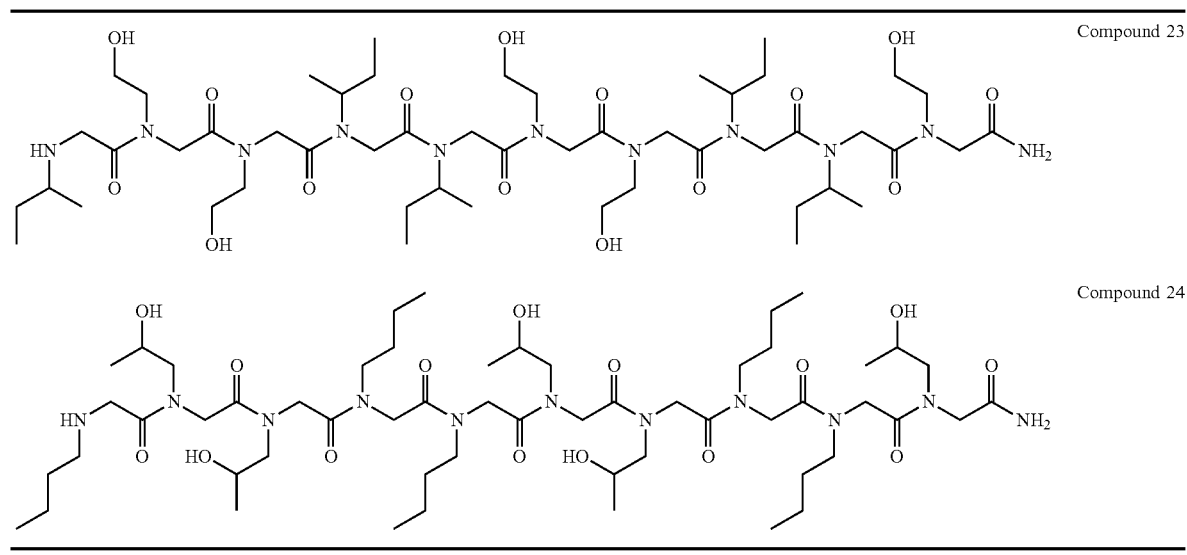
Compound 23
Compound 24
TABLE 5
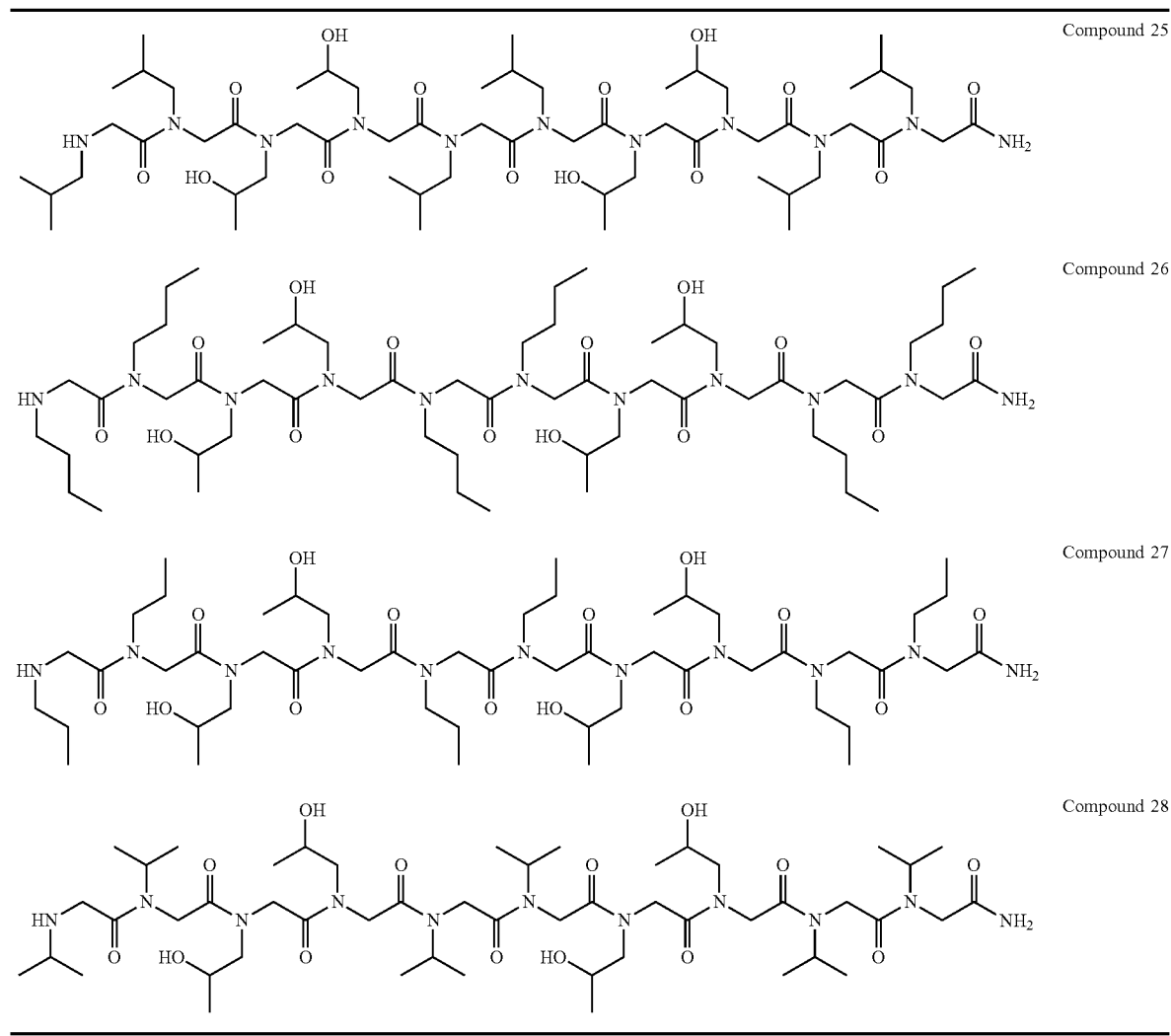
Compound 25
Compound 26
Compound 27
Compound 28

TABLE 6
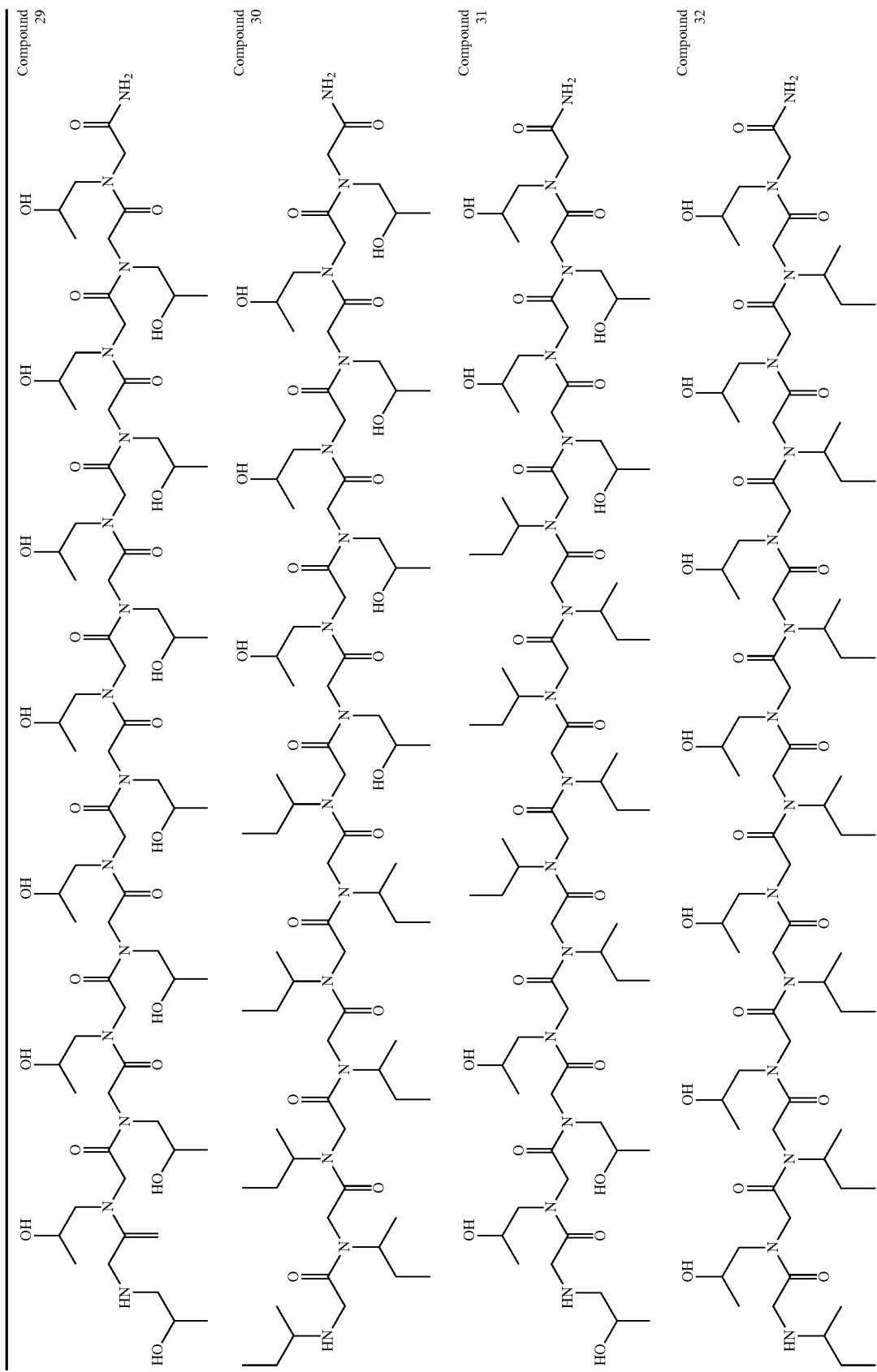

TABLE 6-continued
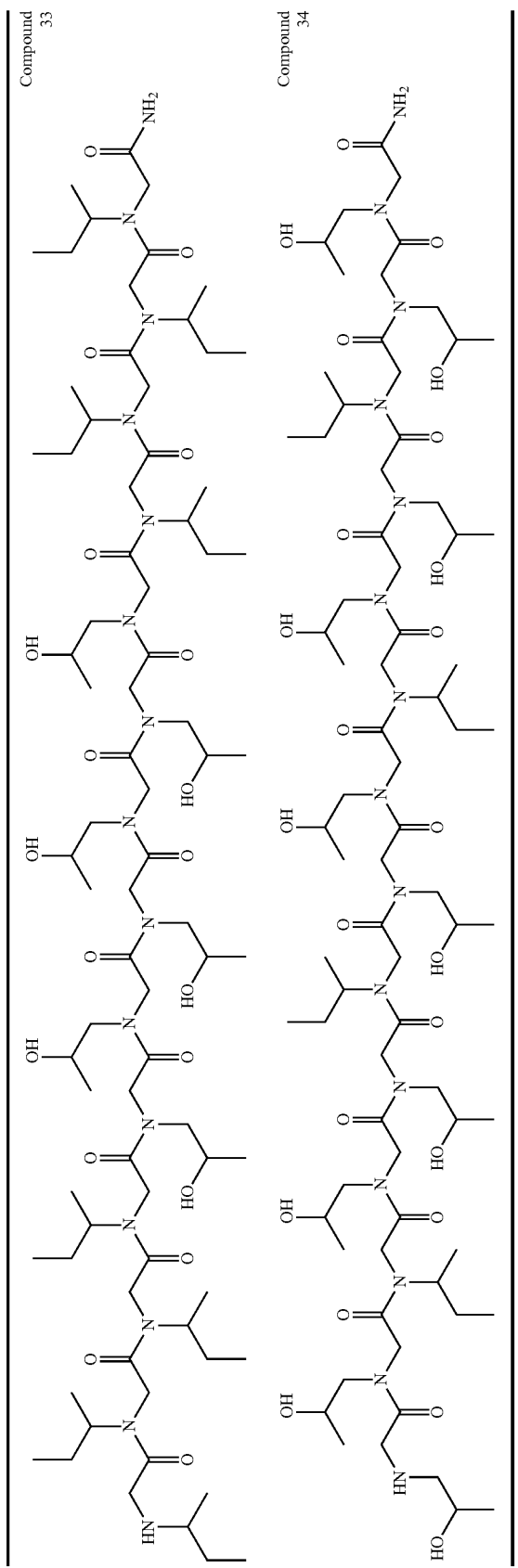

TABLE 7

| Compound 35 | Compound 36 | Compound 37 | Compound 38 |

TABLE 7-continued
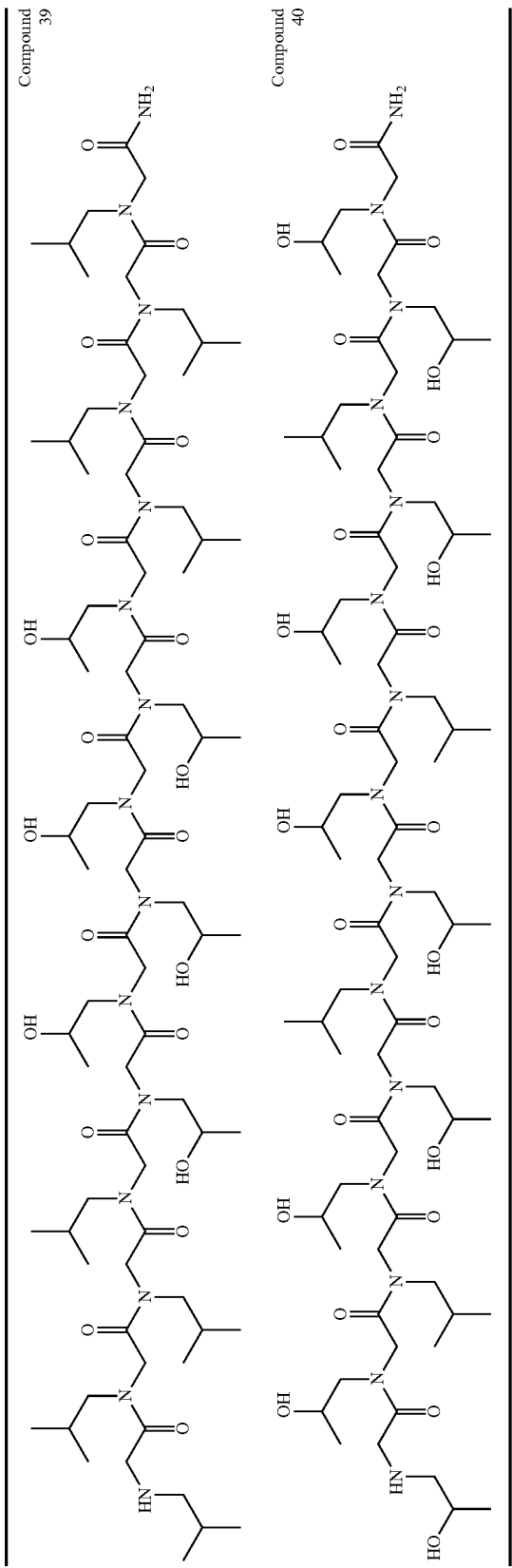

TABLE 8

Compound 41, Compound 42, Compound 43, Compound 44

TABLE 8-continued
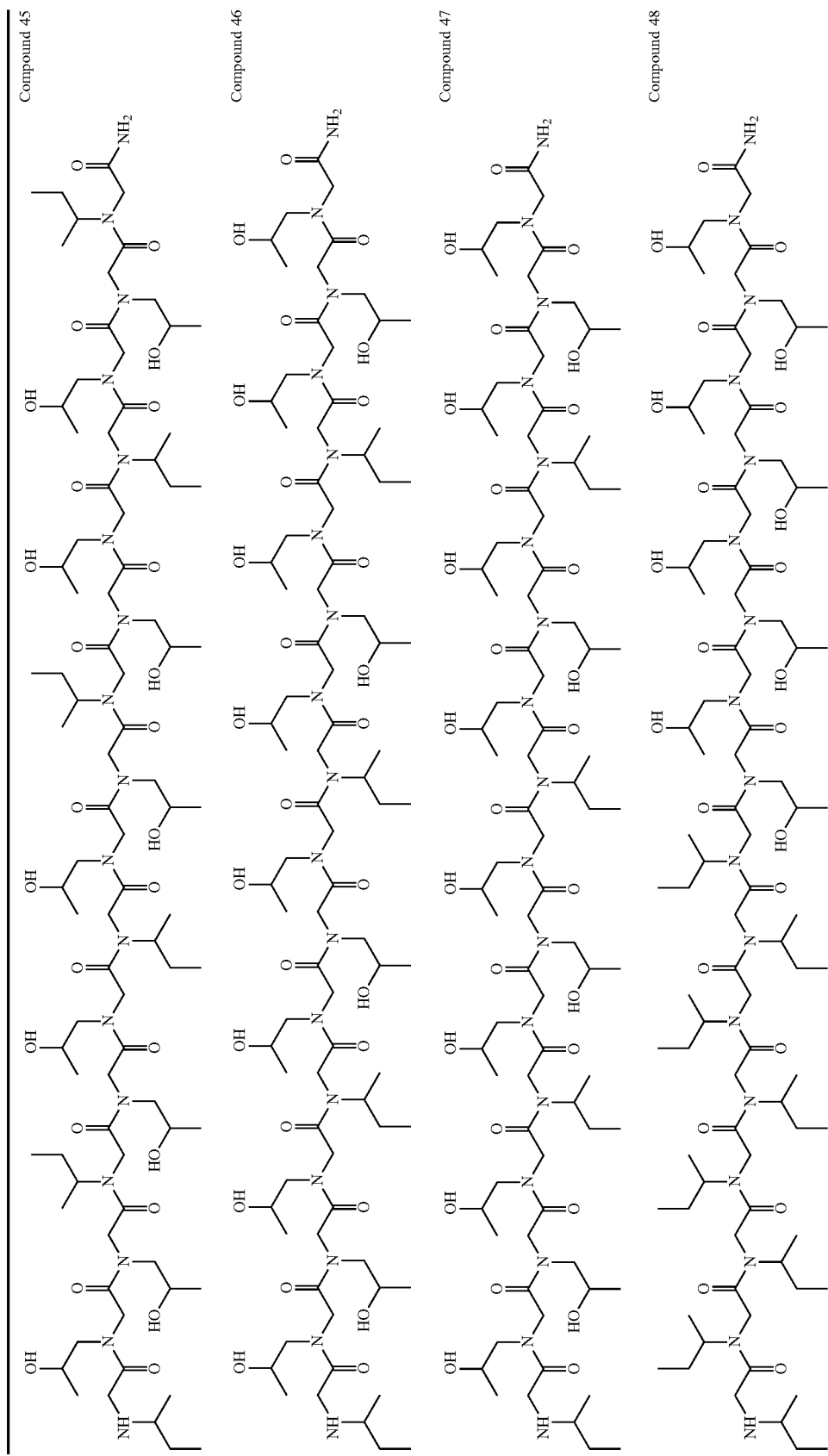

TABLE 8-continued
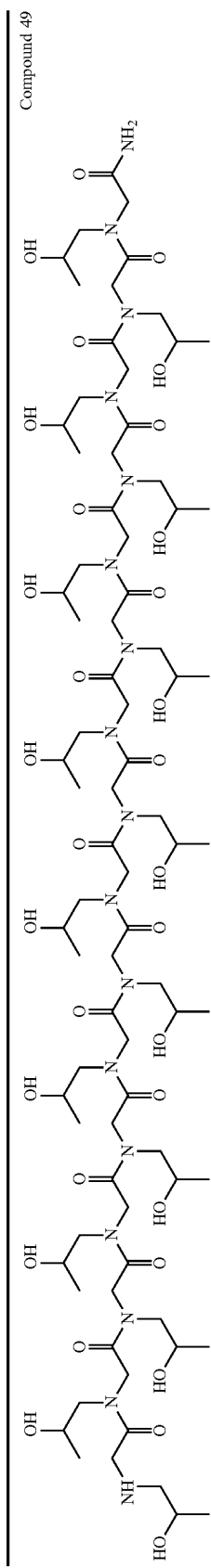
Compound 49

TABLE 9

Compound 50, Compound 51, Compound 52, Compound 53, Compound 54

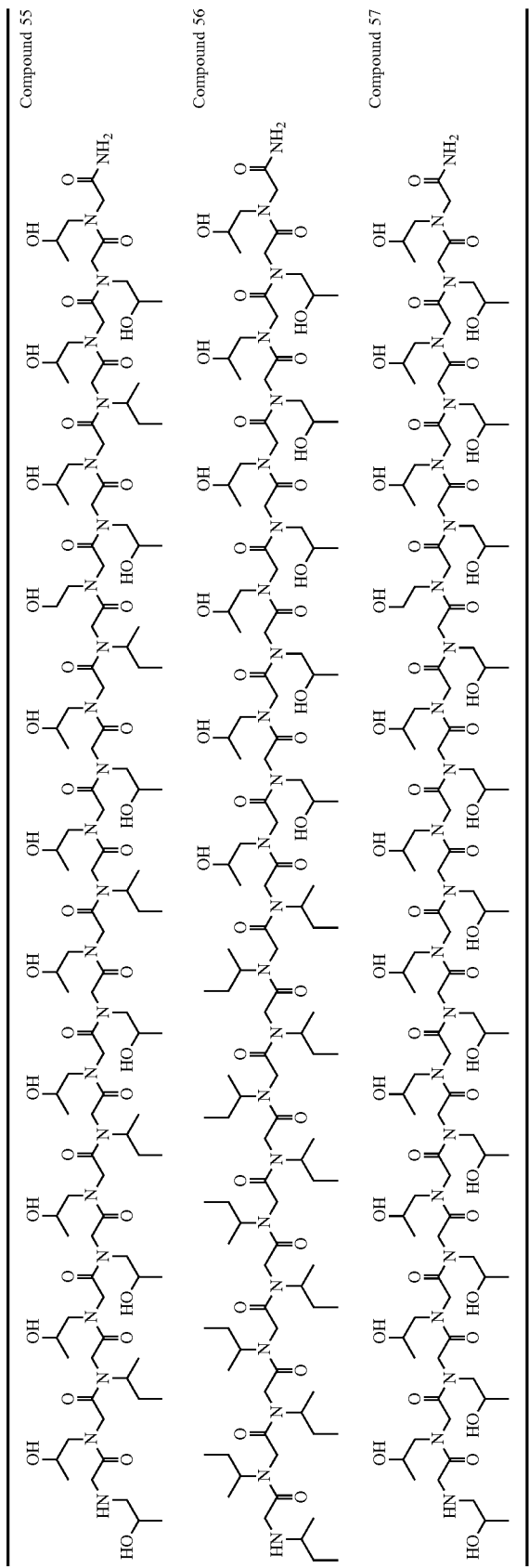

TABLE 10
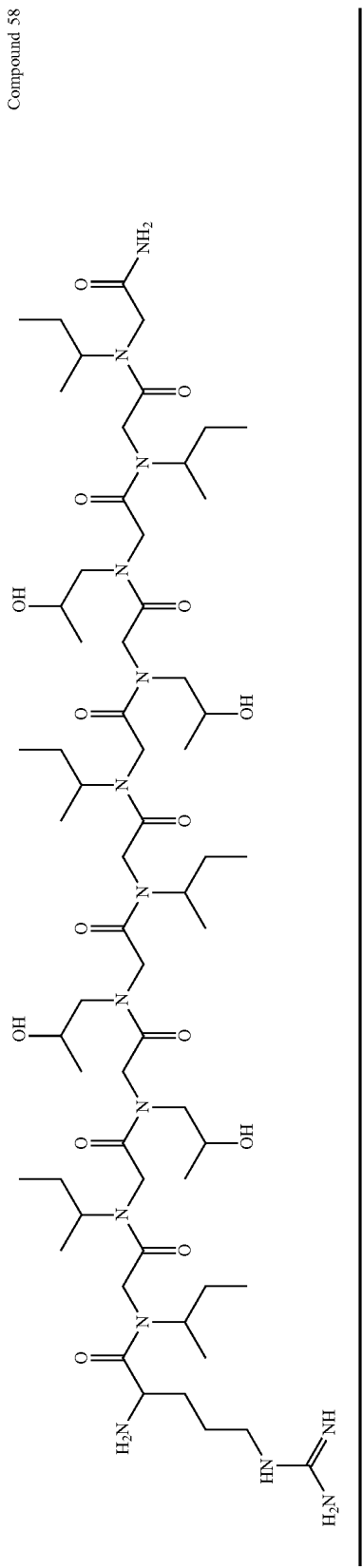
Compound 58

TABLE 11
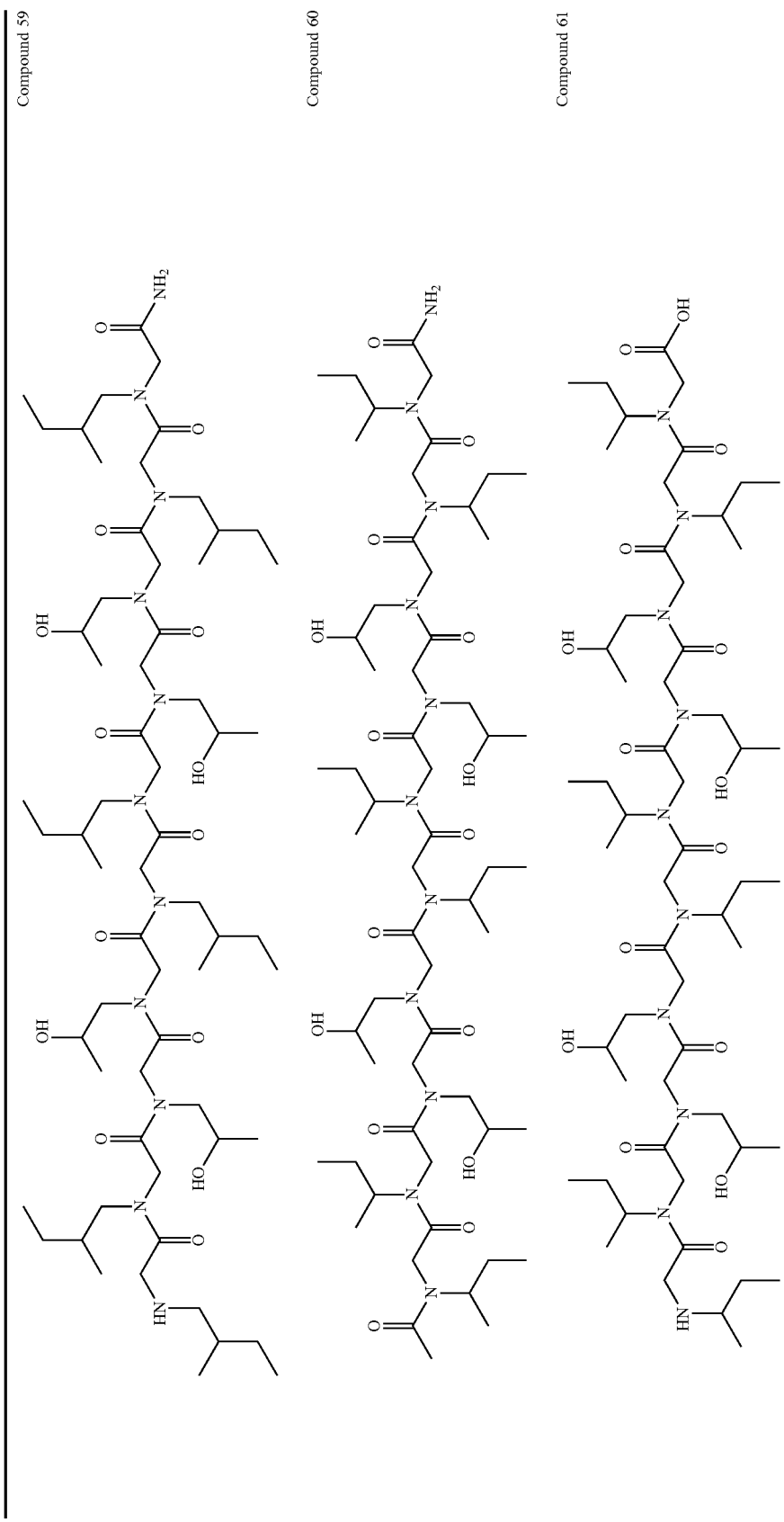

TABLE 11-continued
Compound 62
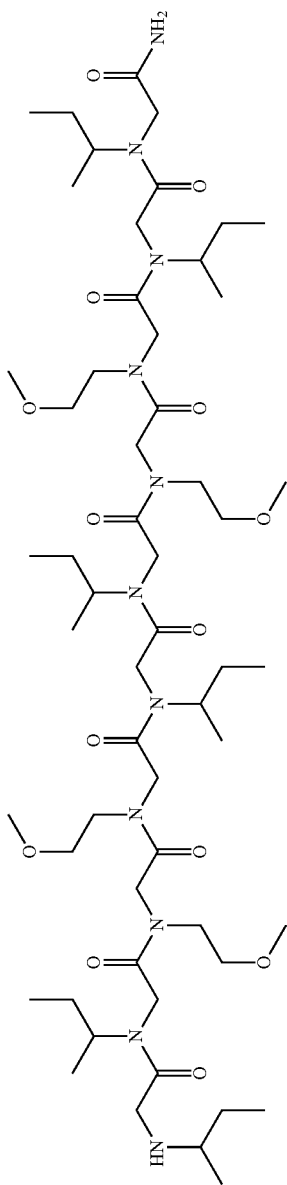
Compound 63
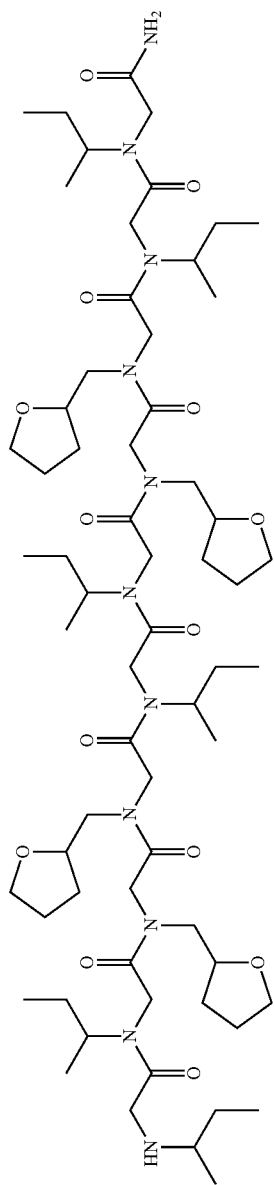
Compound 64
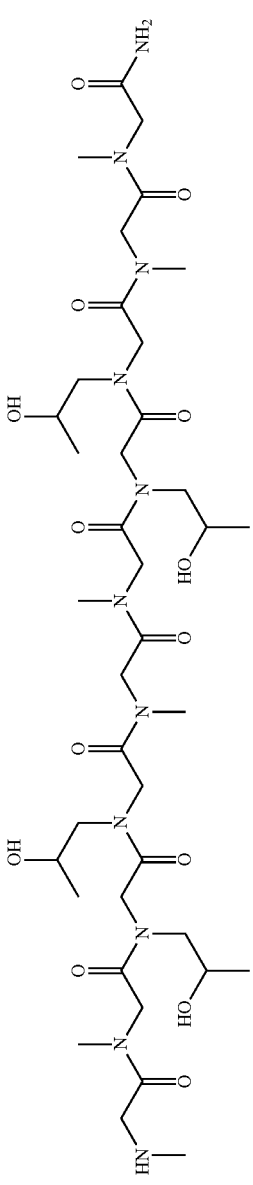

TABLE 11-continued
Compound 65
Compound 66
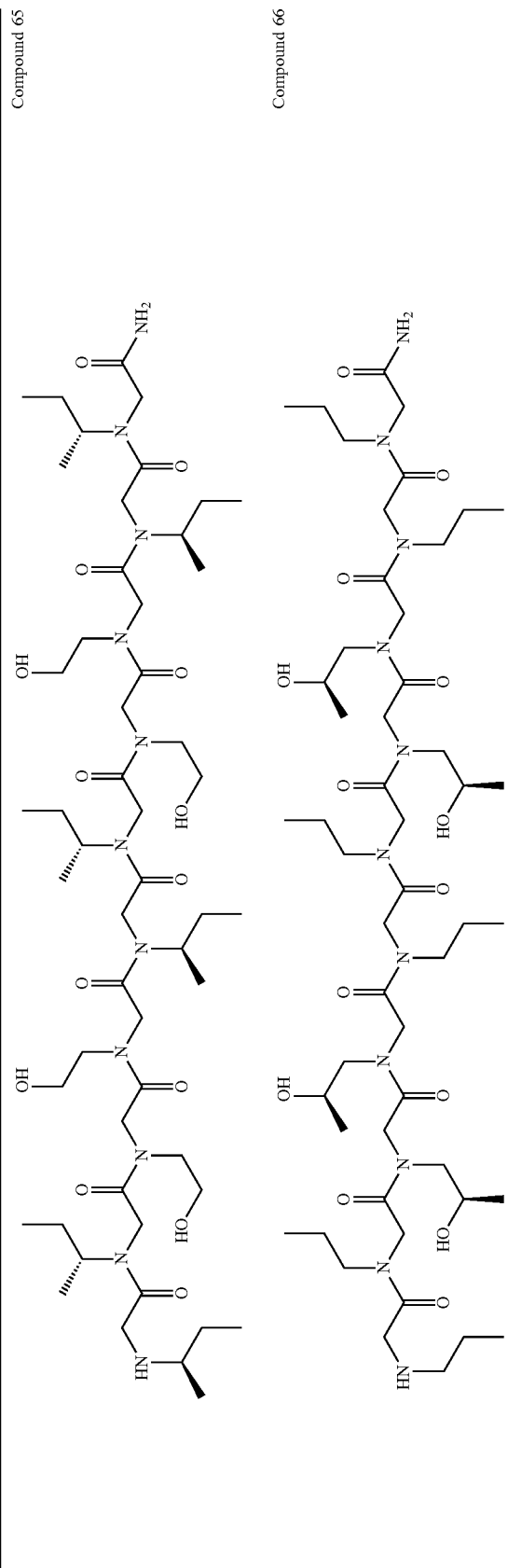

TABLE 11-continued
Compound 67
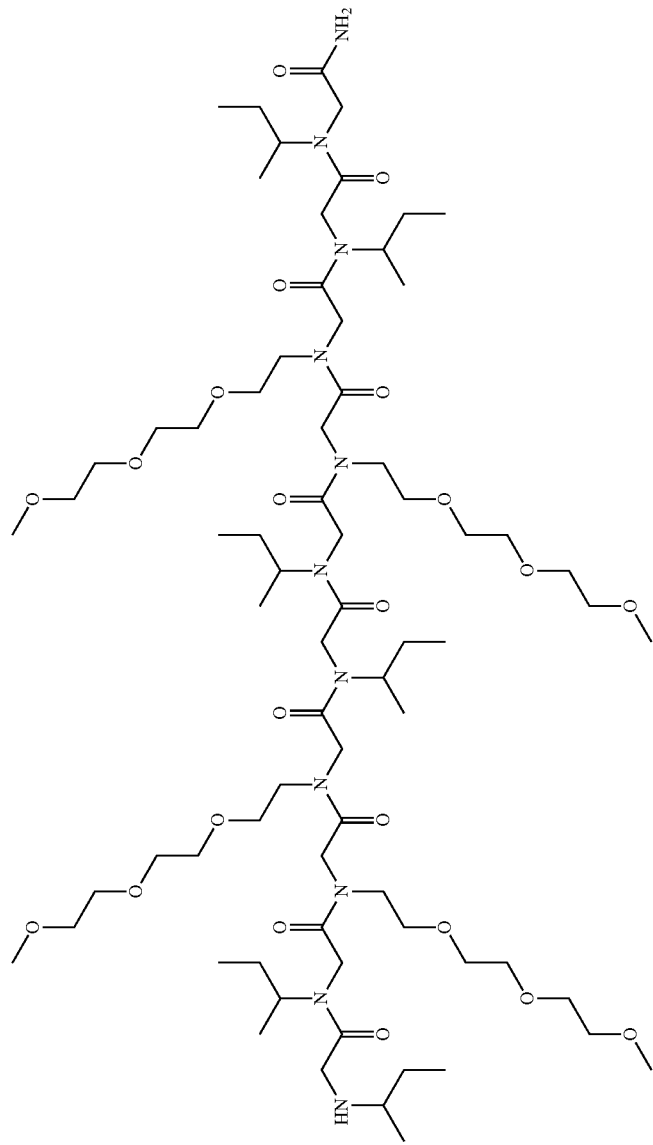
Compound 68
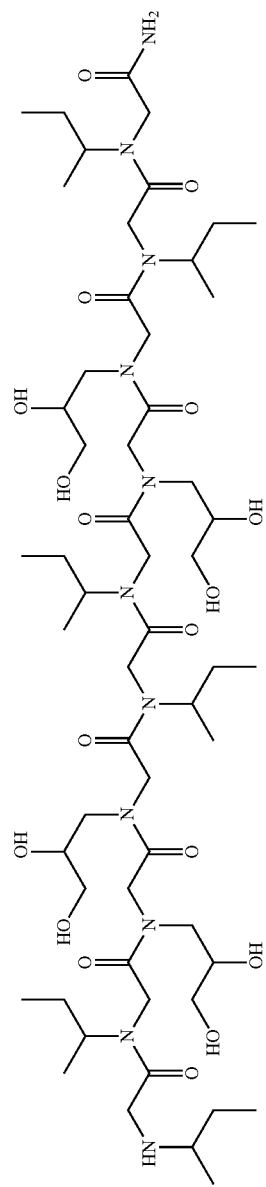

TABLE 11-continued
Compound 69
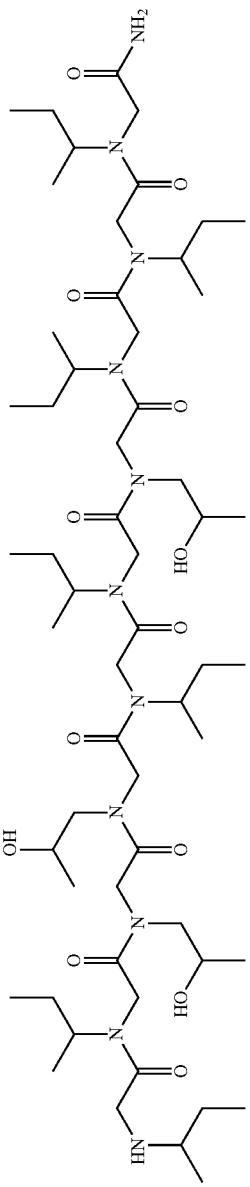
Compound 70
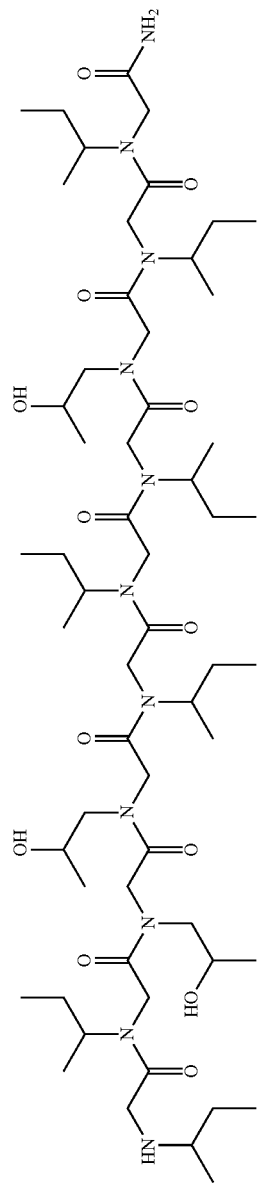
Compound 71
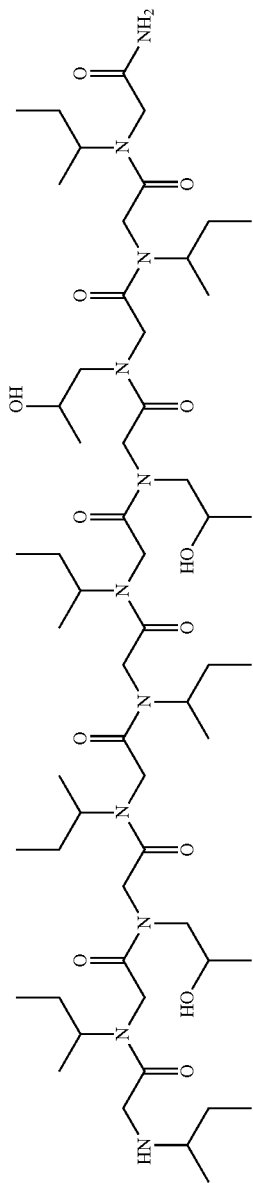
Compound 72
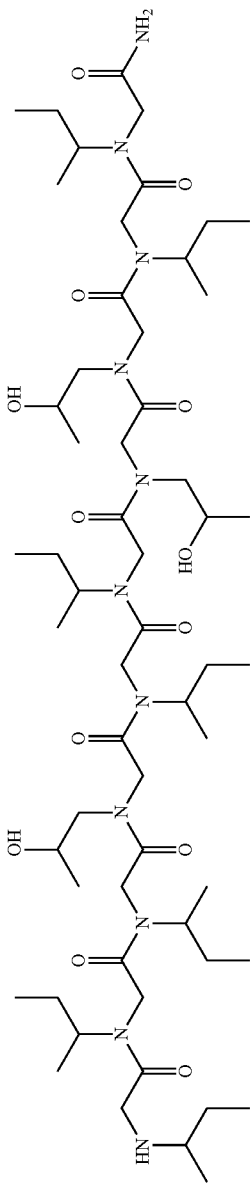

TABLE 11-continued
| Compound 73 | Compound 74 | Compound 75 |
|---|---|---|
| 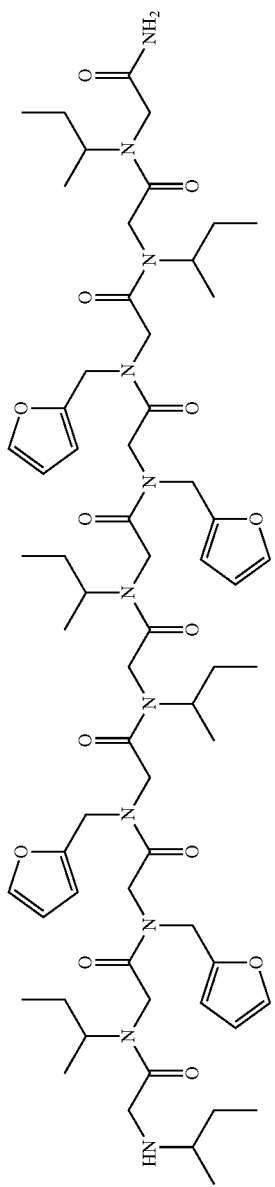 | 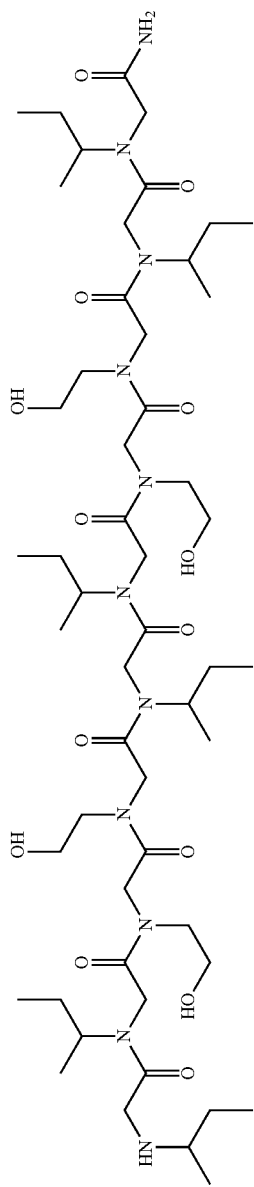 | 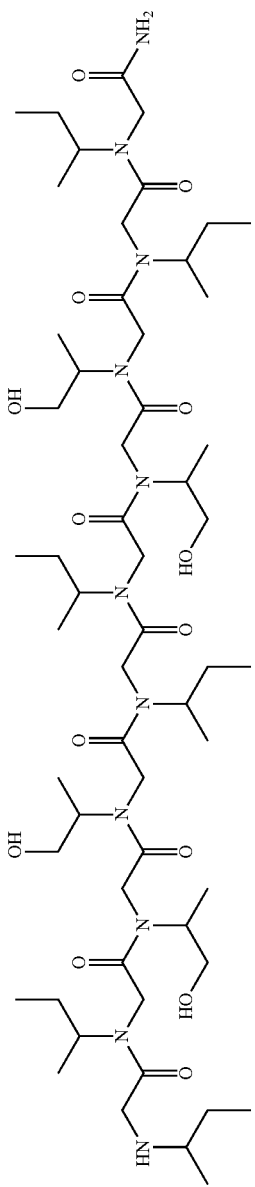 |

TABLE 11-continued
Compound 76
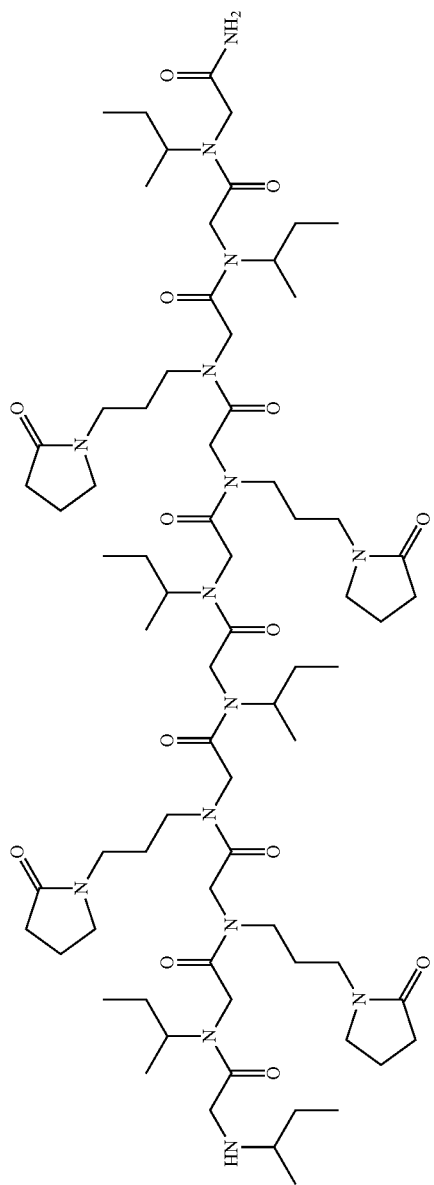
Compound 77
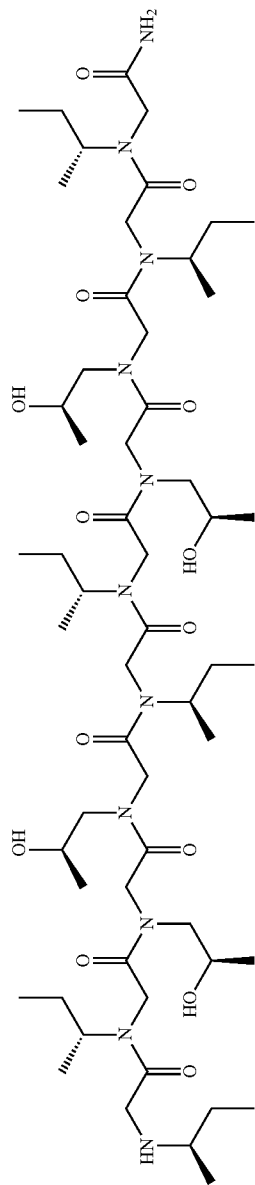
Compound 78
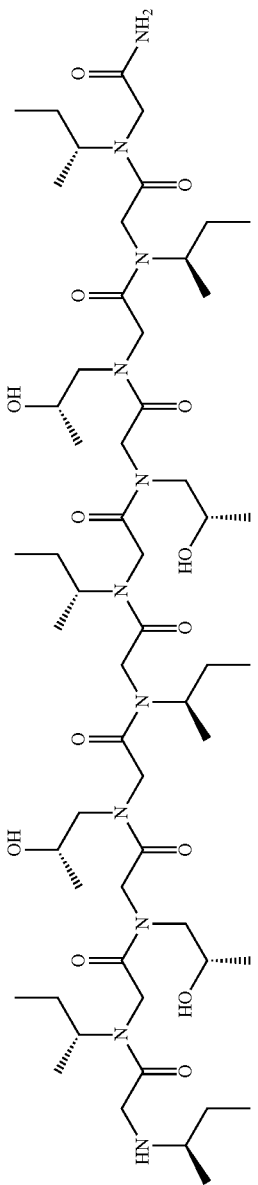

TABLE 11-continued
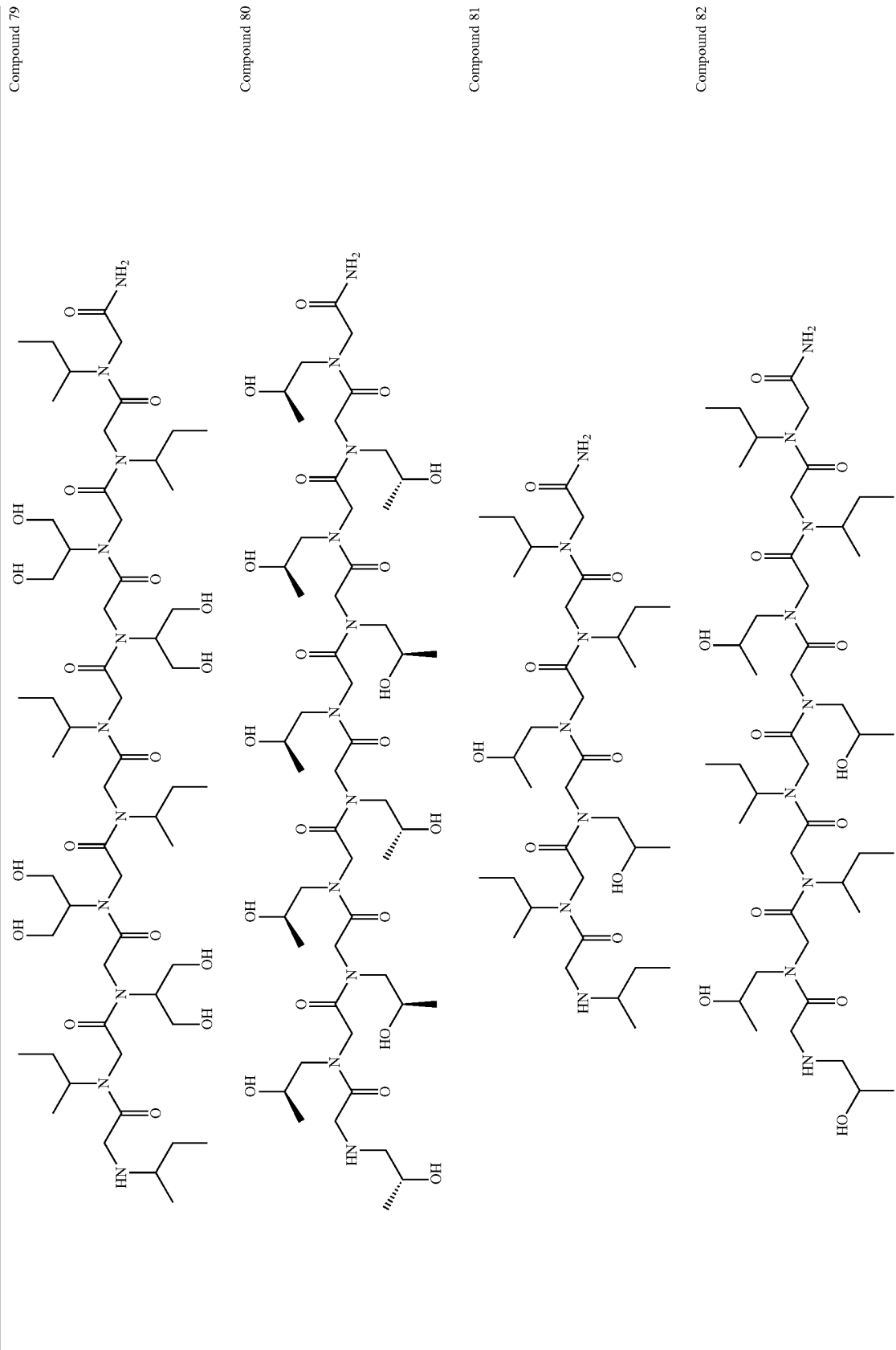
Compound 79
Compound 80
Compound 81
Compound 82

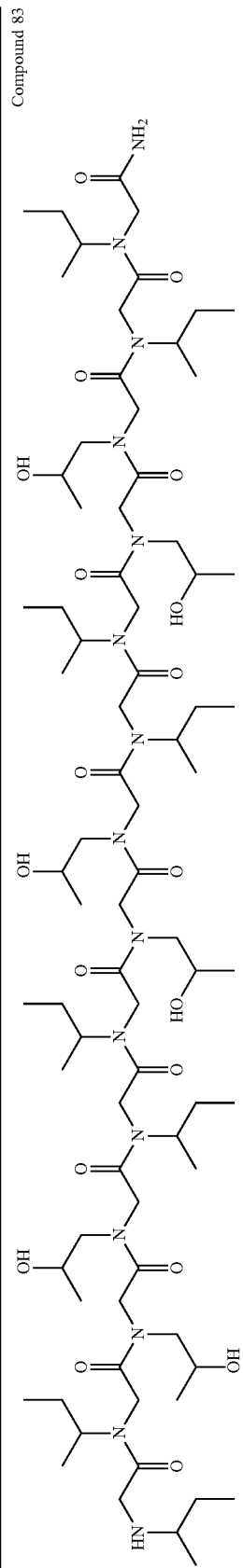

TABLE 11-continued
Compound 87
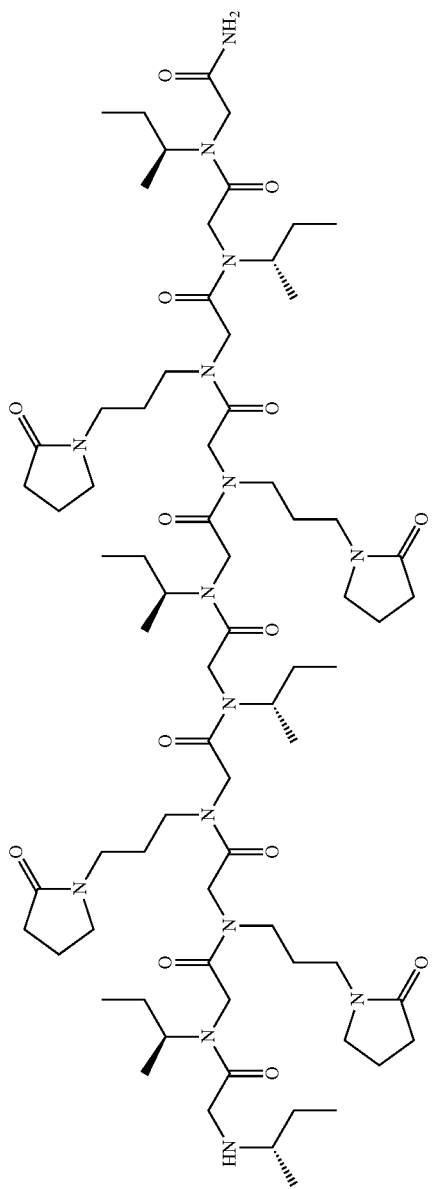
Compound 88
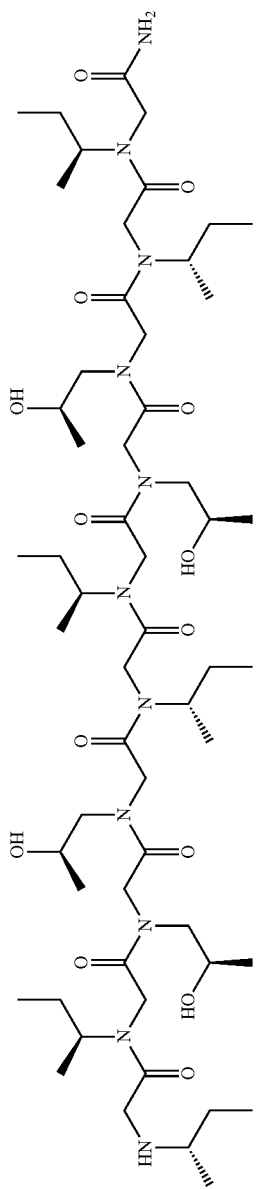
Compound 89
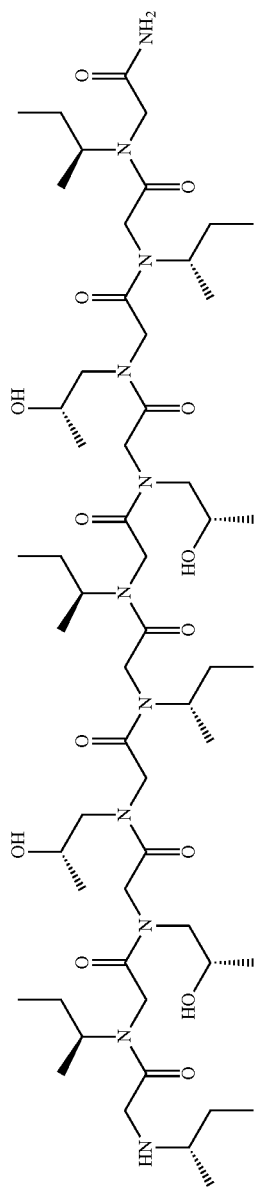

TABLE 11-continued
| Compound 90 | Compound 91 | Compound 92 | Compound 93 |
|---|---|---|---|
| 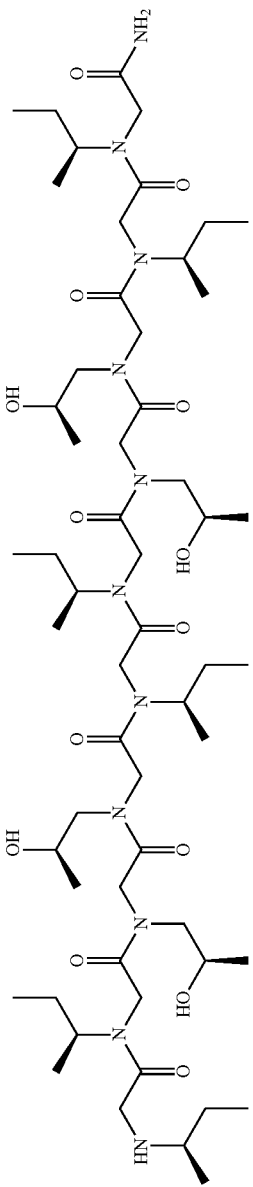 | 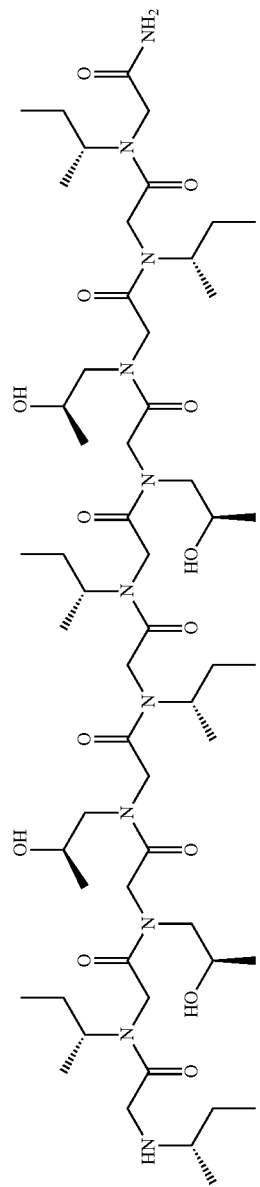 | 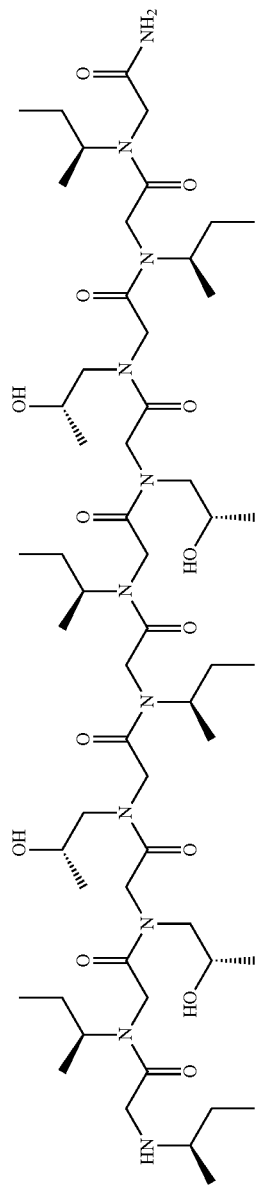 | 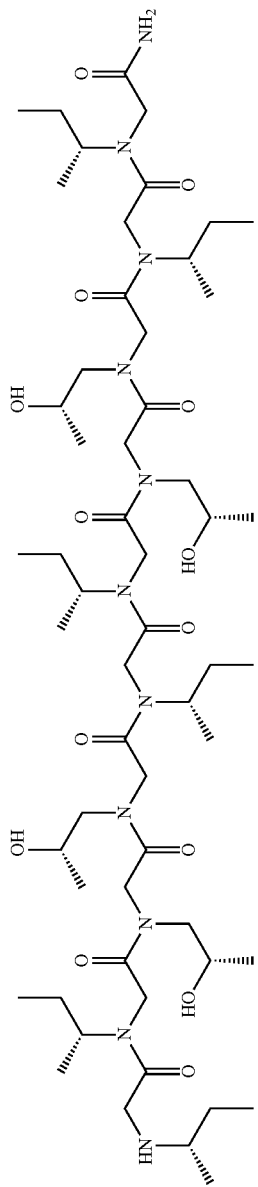 |

TABLE 11-continued
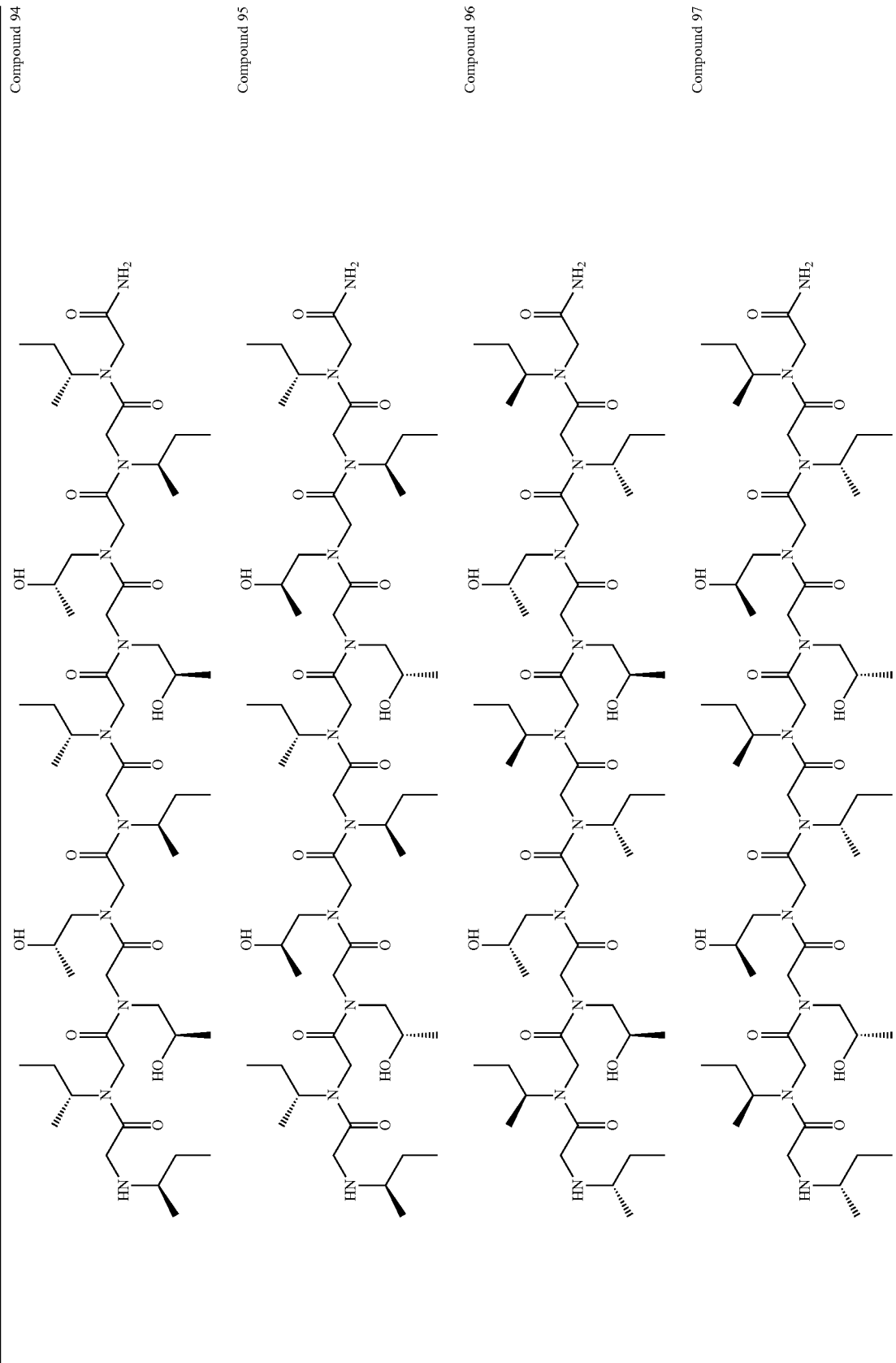
Compound 94
Compound 95
Compound 96
Compound 97

TABLE 11-continued
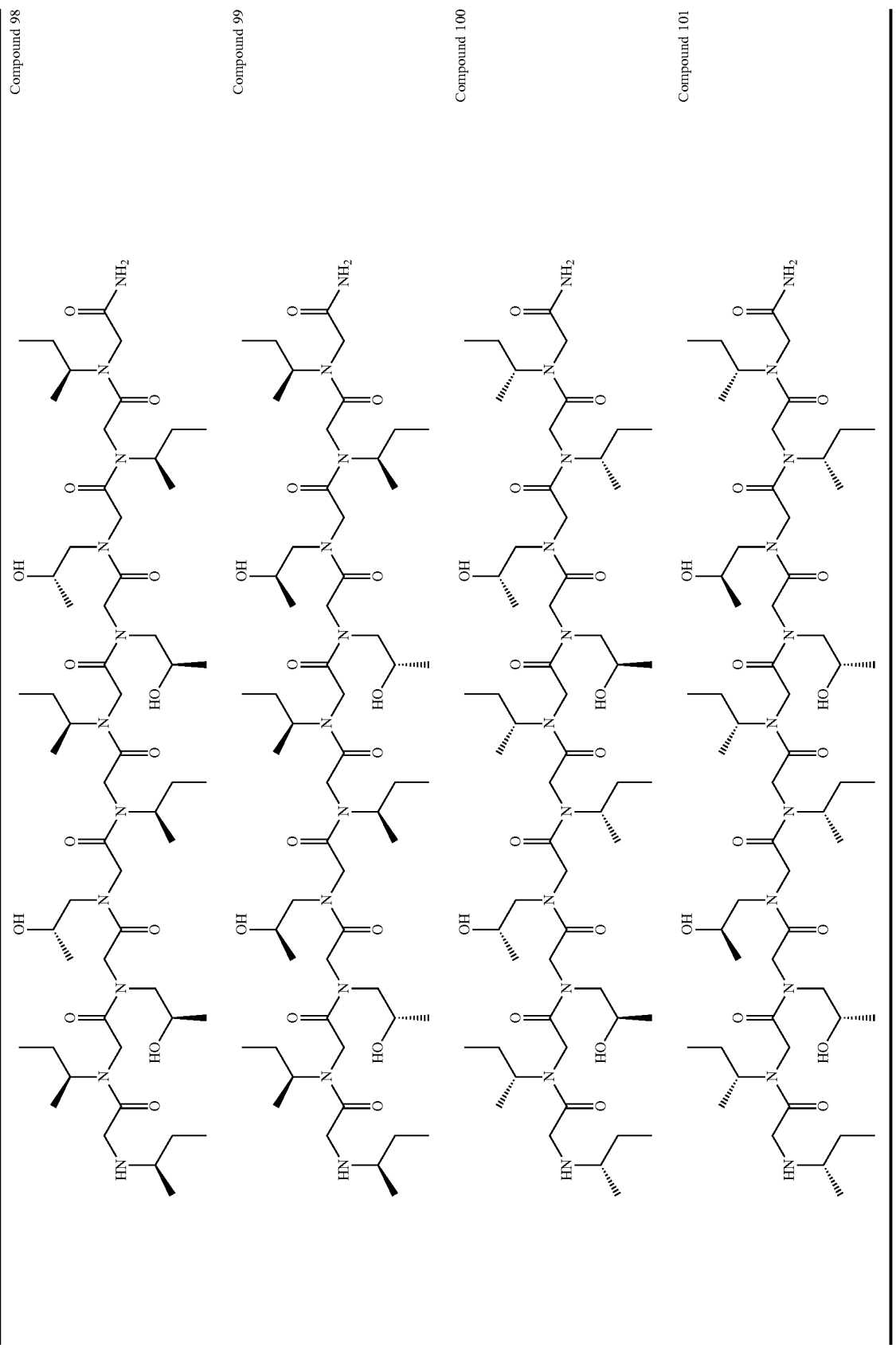

V. Exemplary Embodiments

Exemplary embodiments provided in accordance with the presently disclosed subject matter include, but are not limited to, the claims and the following embodiments:

1. A peptoid polymer or salt thereof comprising subunits comprising one or more first hydrophobic peptoid monomers H and one or more first polar peptoid monomers P arranged such that the peptoid polymer has the sequence $[H_aP_b]_n$ or $[P_bH_a]_n$, wherein:
   - the subscript a, representing the number of consecutive first hydrophobic peptoid monomers within a subunit, is between 1 and 10;
   - the subscript b, representing the number of consecutive first polar peptoid monomers within a subunit, is between 1 and 10; and
   - the subscript n, representing the number of subunits within the peptoid polymer, is between 2 and 50.

2. The peptoid polymer or salt thereof of embodiment 1, further comprising substituents X and Y such that the peptoid polymer has the sequence $X-[H_aP_b]_n-Y$ or $X-[P_bH_a]_n-Y$, wherein:
   - X and Y are independently selected from the group consisting of H, optionally substituted $C_{1-8}$ alkyl, optionally substituted $C_{1-8}$ acyl, optionally substituted $C_{1-8}$ alkylamino, —OH, —SH, —NH$_2$, carboxy, optionally substituted $C_{1-8}$ hydroxyalkyl, optionally substituted $C_{1-8}$ alkylamino, optionally substituted $C_{2-8}$ alkylthio, optionally substituted $C_{1-8}$ carboxyalkyl, and halogen, or
   - alternatively X and Y are taken together to form a covalent bond.

3. The peptoid polymer or salt thereof of embodiment 1, wherein the subunits further comprise a second hydrophobic peptoid monomer and/or a second polar peptoid monomer such that the peptoid polymer has the sequence $[H_aP_bH_cP_d]_n$ or $[P_bH_aP_dH_c]_n$, wherein:
   - the subscript c, representing the number of consecutive second hydrophobic peptoid monomers within a subunit, is between 0 and 10;
   - the subscript d, representing the number of consecutive second polar peptoid monomers within a subunit, is between 0 and 10; and
   - both c and d are not 0.

4. The peptoid polymer or salt thereof of embodiment 3, further comprising substituents X and Y such that the peptoid polymer has the sequence $X-[H_aP_bH_cP_d]_n-Y$ or $X-[P_bH_aP_dH_c]_n-Y$, wherein:
   - X and Y are independently selected from the group consisting of H, optionally substituted $C_{1-8}$ alkyl, optionally substituted $C_{1-8}$ acyl, optionally substituted $C_{1-8}$ alkylamino, —OH, —SH, —NH$_2$, carboxy, optionally substituted $C_{1-8}$ hydroxyalkyl, optionally substituted $C_{1-8}$ alkylamino, optionally substituted $C_{2-8}$ alkylthio, optionally substituted $C_{1-8}$ carboxyalkyl, and halogen, or
   - alternatively X and Y are taken together to form a covalent bond.

5. The peptoid polymer or salt thereof of any one of embodiments 1 to 4, further comprising a sequence Z that comprises one or more hydrophobic peptoid monomers and/or one or more polar peptoid monomers, wherein Z is located before the first subunit, after the last subunit, and/or between one or more subunits.

6. The peptoid polymer or salt thereof of embodiment 5, wherein Z comprises one or more hydrophobic peptoid monomers.

7. The peptoid polymer or salt thereof of embodiment 5, wherein Z comprises one or more polar peptoid monomers.

8. The peptoid polymer or salt thereof of embodiment 5, wherein Z comprises one or more hydrophobic peptoid monomers and one or more polar peptoid monomers.

9. The peptoid polymer or salt thereof of any one of embodiments 1 to 8, wherein n is between 2 and 10.

10. The peptoid polymer or salt thereof of any one of embodiments 1 to 9, where a is between 1 and 5.

11. The peptoid polymer or salt thereof of any one of embodiments 1 to 10, wherein b is between 1 and 5.

12. The peptoid polymer or salt thereof of embodiment 10 or 11, wherein a is between 1 and 3 and b is between 1 and 3.

13. The peptoid polymer or salt thereof of any one of embodiments 3 to 12, wherein c is between 0 and 5.

14. The peptoid polymer or salt thereof of any one of embodiments 3 to 13, wherein d is between 0 and 5.

15. A peptoid polymer or salt thereof comprising:
   (a) subunits comprising two first hydrophobic peptoid monomers H and two first polar peptoid monomers P, and
   (b) two second hydrophobic peptoid monomers located at the C-terminal end of the peptoid polymer,
   arranged such that the peptoid polymer has the sequence $[H_2P_2]_nH_2$ or $[P_2H_2]_nH_2$, wherein the subscript n, representing the number of subunits within the peptoid polymer, is between 1 and 50.

16. The peptoid polymer or salt thereof of embodiment 15, comprising Compound 81.

17. The peptoid polymer or salt thereof of embodiment 15 or 16, further comprising substituents X and Y such that the peptoid polymer has the sequence $X-[H_2P_2]_nH_2-Y$ or $X-[P_2H_2]_nH_2-Y$, wherein:
   - X and Y are independently selected from the group consisting of H, optionally substituted $C_{1-8}$ alkyl, optionally substituted $C_{1-8}$ acyl, optionally substituted $C_{1-8}$ alkylamino, —OH, —SH, —NH$_2$, carboxy, optionally substituted $C_{1-8}$ hydroxyalkyl, optionally substituted $C_{1-8}$ alkylamino, optionally substituted $C_{2-8}$ alkylthio, optionally substituted $C_{1-8}$ carboxyalkyl, and halogen, or
   - alternatively X and Y are taken together to form a covalent bond.

18. The peptoid polymer or salt thereof of any one of embodiments 15 to 17, wherein n is between 1 and 10.

19. The peptoid polymer or salt thereof of any one of embodiments 1 to 18, wherein the first and/or second hydrophobic peptoid monomers are independently selected from the group consisting of

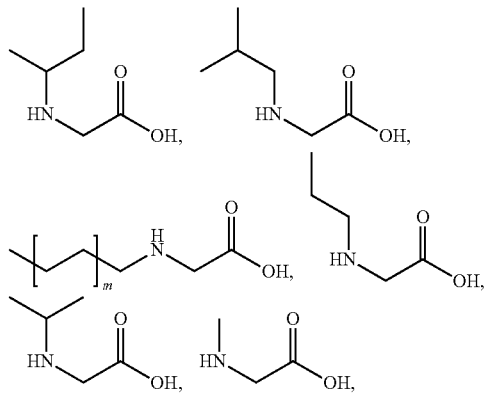

133
-continued

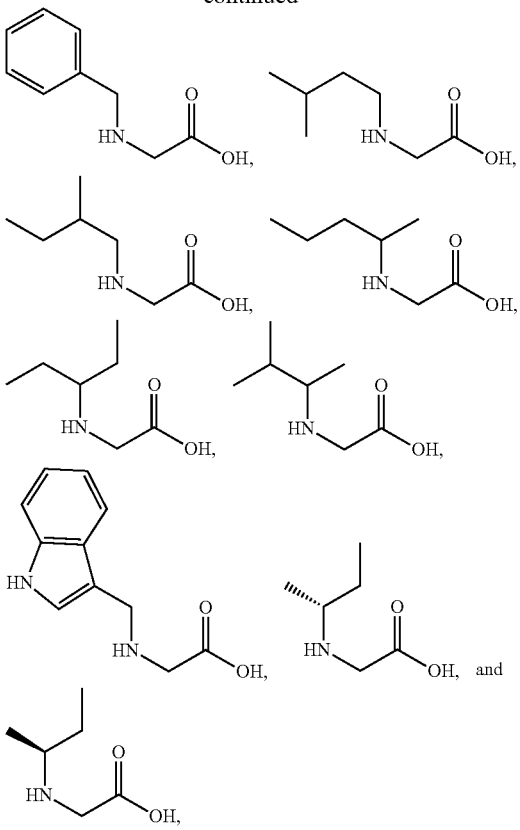

wherein the subscript m is the number of repeat units and is between 1 and 10.

20. The peptoid polymer or salt thereof of any one of embodiments 1 to 15 or 17 to 19, wherein none of the polar peptoid monomers comprise a side chain that comprises an optionally substituted $C_{1-18}$ hydroxyalkyl group.

21. The peptoid polymer or salt thereof of any one of embodiments 1 to 20, wherein each of the first and/or second polar peptoid monomers comprise a side chain that is independently selected from the group consisting of ($C_{1-6}$ alkoxy)($C_{1-6}$ alkylene), (oligo[ethylene glycol]), (4- to 10-membered heterocycloalkyl)($C_{1-6}$ alkylene), and (5- to 10-membered heteroaryl)($C_{1-6}$ alkylene).

22. The peptoid polymer or salt thereof of embodiment 21, wherein (4- to 10-membered heterocycloalkyl)($C_{1-6}$ alkylene) comprises a 4-6 membered heterocyclic ring, wherein at least one member is selected from the group consisting of O and N.

23. The peptoid polymer or salt thereof of embodiment 21 or 22, wherein (4- to 10-membered heterocycloalkyl)($C_{1-6}$ alkylene) comprises a tetrahydrofuranyl or oxopyrrolidinyl moiety.

24. The peptoid polymer or salt thereof of embodiment 23, wherein the peptoid polymer comprises

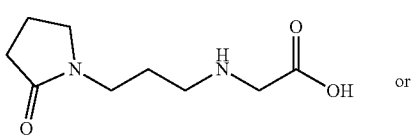 or

134
-continued

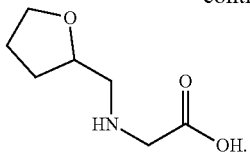

25. The peptoid polymer or salt thereof of embodiment 24, wherein all of the polar peptoid monomers are

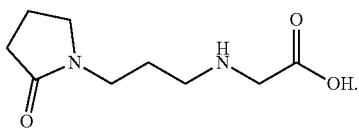 [SMILES: O=C(O)CNCCCN1CCCC1=O]

26. The peptoid polymer or salt thereof of embodiment 24 or 25, wherein the peptoid polymer comprises Compound 63, Compound 76, Compound 86, or Compound 87.

27. The peptoid polymer or salt thereof of embodiment 21, wherein (5- to 10-membered heteroaryl)($C_{1-6}$ alkylene) comprises a 5-6 membered aromatic ring, wherein at least one ring member is selected from the group consisting of O and N.

28. The peptoid polymer or salt thereof of embodiment 21 or 27, wherein (5- to 10-membered heteroaryl)($C_{1-6}$ alkylene) comprises a furanyl moiety.

29. The peptoid polymer or salt thereof of embodiment 28, wherein the peptoid polymer comprises

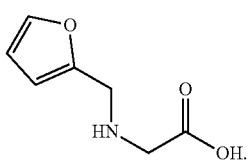 [SMILES: O=C(O)CNCc1ccco1]

30. The peptoid polymer or salt thereof of embodiment 29, wherein the peptoid polymer comprises Compound 73.

31. The peptoid polymer or salt thereof of embodiment 21, wherein the side chain comprises a methoxyethyl group.

32. The peptoid polymer or salt thereof of embodiment 31, wherein the peptoid polymer comprises

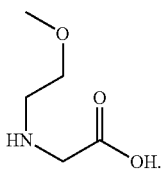

33. The peptoid polymer or salt thereof of embodiment 32, wherein the peptoid polymer comprises Compound 62.

34. The peptoid polymer or salt thereof of embodiment 21, wherein the side chain comprises an oligo(ethylene glycol) moiety.

35. The peptoid polymer or salt thereof of embodiment 34, wherein the oligo(ethylene glycol) moiety is a 2-(2-(2-methoxyethoxy)ethoxy)ethyl moiety.

36. The peptoid polymer or salt thereof of embodiment 35, wherein the peptoid polymer comprises

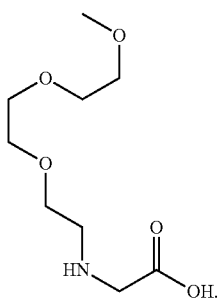

37. The peptoid polymer or salt thereof of embodiment 36, wherein the peptoid polymer comprises Compound 67.

38. The peptoid polymer or salt thereof of any one of embodiments 1 to 19, wherein the peptoid polymer comprises a polar peptoid monomer having a side chain that comprises a hydroxyl group.

39. The peptoid polymer or salt thereof of any one of embodiments 1 to 19, wherein the first and/or second polar peptoid monomers are independently selected from the group consisting of

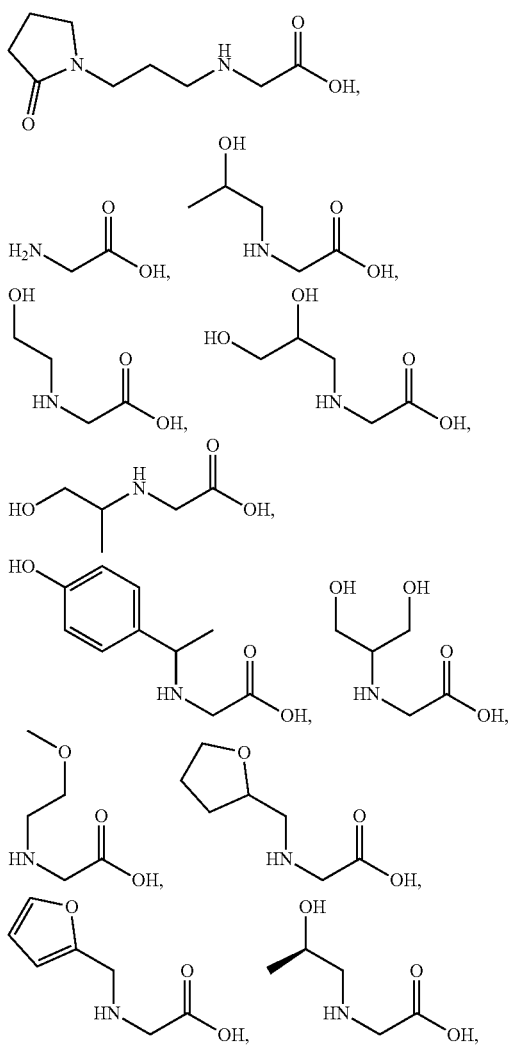

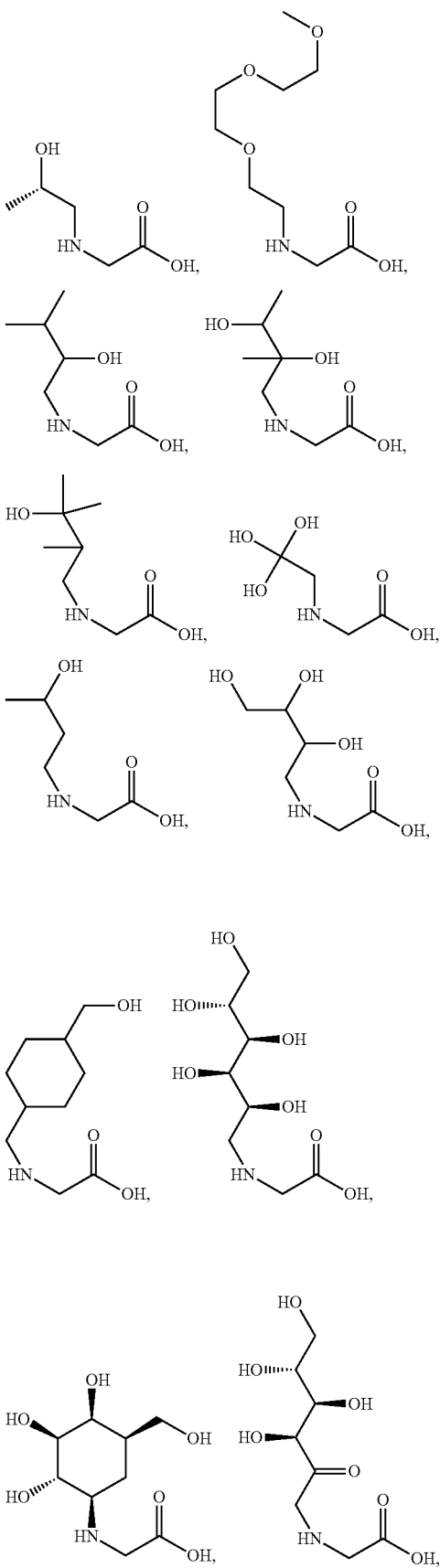

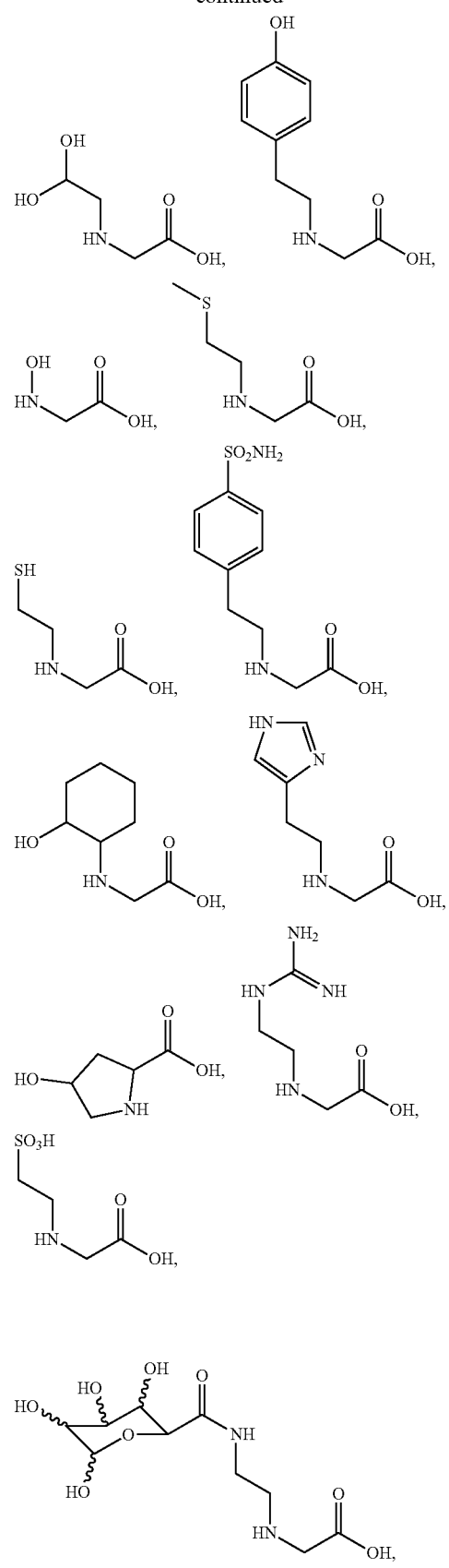
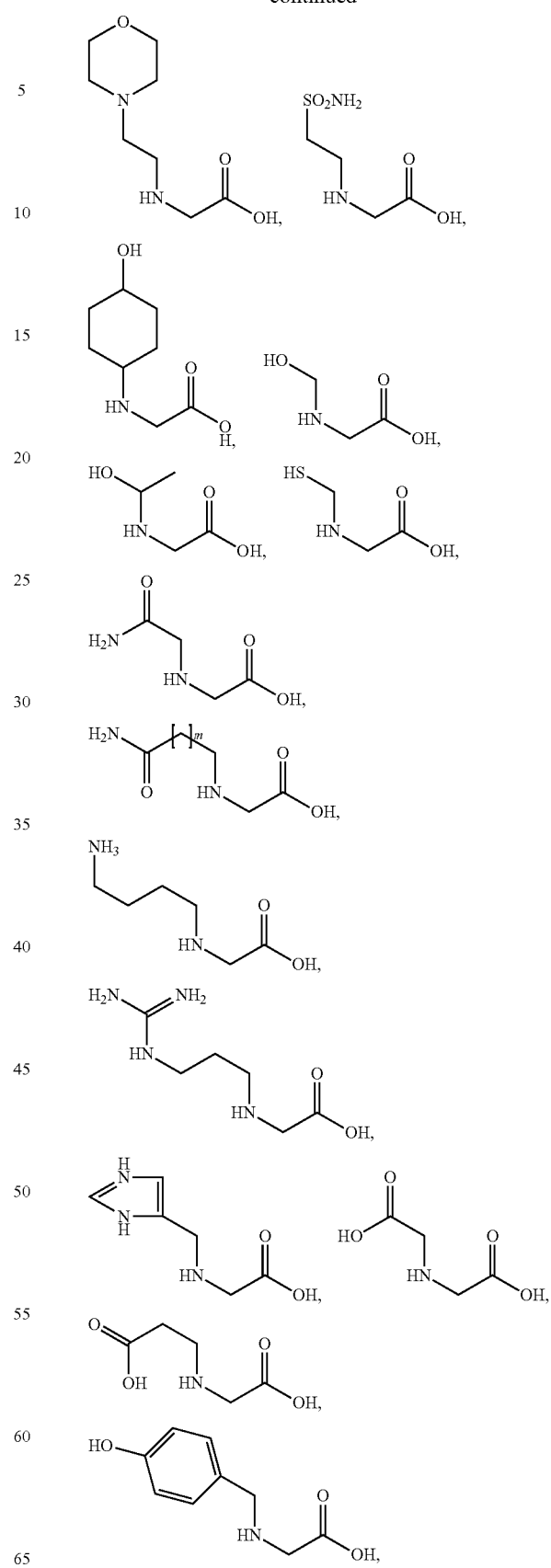

-continued

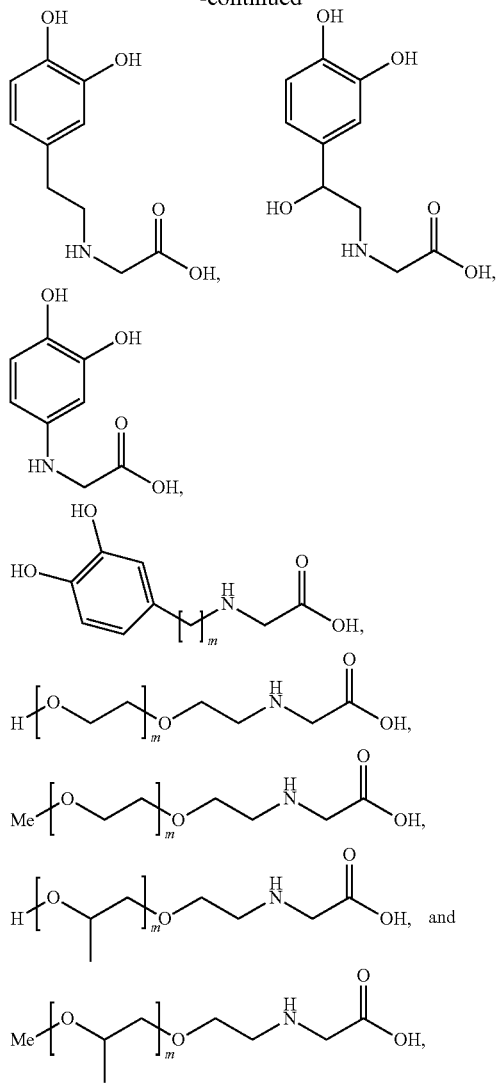

wherein the subscript m is the number of repeat units and is between 1 and 10.

40. A peptoid polymer or salt thereof comprising one or more hydrophobic peptoid monomers and one or more polar peptoid monomers, wherein each of the one or more polar peptoid monomers comprise a side chain that is independently selected from the group consisting of ($C_{1-6}$ alkoxy)($C_{1-6}$ alkylene), (oligo[ethylene glycol]), (4- to 10-membered heterocycloalkyl)($C_{1-6}$ alkylene), and (5- to 10-membered heteroaryl)($C_{1-6}$ alkylene).

41. The peptoid polymer or salt thereof of embodiment 40, wherein each of the one or more hydrophobic peptoid monomers is independently selected from the group consisting of

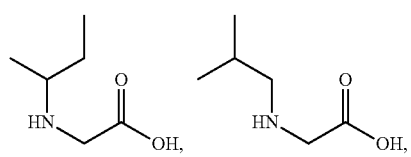

-continued

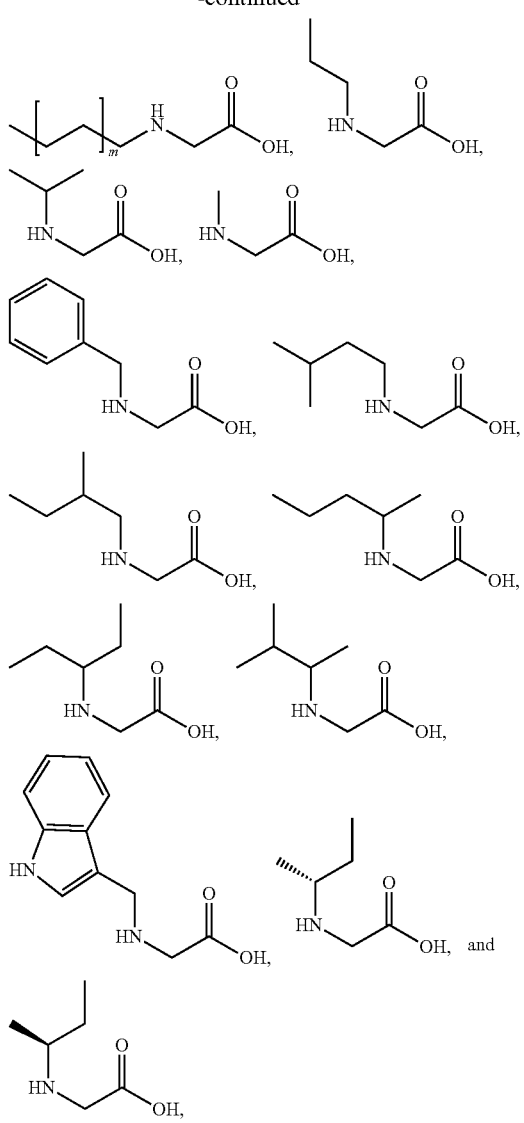

wherein the subscript m is the number of repeat units and is between 1 and 10.

42. The peptoid polymer or salt thereof of embodiment 40 or 41, wherein (4- to 10-membered heterocycloalkyl)($C_{1-6}$ alkylene) comprises a 4-6 membered heterocyclic ring, wherein at least one member is selected from the group consisting of O and N.

43. The peptoid polymer or salt thereof of any one of embodiments 40 to 42, wherein (4- to 10-membered heterocycloalkyl)($C_{1-6}$ alkylene) comprises a tetrahydrofuranyl or oxopyrrolidinyl moiety.

44. The peptoid polymer or salt thereof of embodiment 43, wherein the peptoid polymer comprises

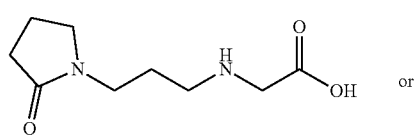

-continued

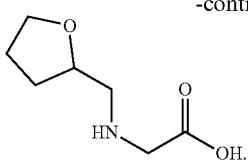

45. The peptoid polymer or salt thereof of embodiment 44, wherein all of the polar peptoid monomers are

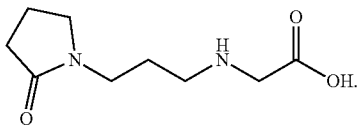 [SMILES: O=C(O)CNCCCN1CCCC1=O]

46. The peptoid polymer or salt thereof of embodiment 44 or 45, wherein the peptoid polymer comprises Compound 63, Compound 76, Compound 86, or Compound 87.

47. The peptoid polymer or salt thereof of embodiment 40 or 41, wherein (5- to 10-membered heteroaryl)($C_{1-6}$ alkylene) comprises a 5-6 membered aromatic ring, wherein at least one ring member is selected from the group consisting of O and N.

48. The peptoid polymer or salt thereof of embodiment 40, 41, or 47, wherein (5- to 10-membered heteroaryl)($C_{1-6}$ alkylene) comprises a furanyl moiety.

49. The peptoid polymer or salt thereof of embodiment 48, wherein the peptoid polymer comprises

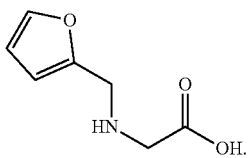 [SMILES: O=C(O)CNCc1ccco1]

50. The peptoid polymer or salt thereof of embodiment 49, wherein the peptoid polymer comprises Compound 73.

51. The peptoid polymer or salt thereof of embodiment 40 or 41, wherein the side chain comprises a methoxyethyl group.

52. The peptoid polymer or salt thereof of embodiment 51, wherein the peptoid polymer comprises

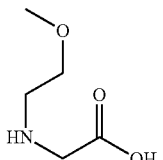

53. The peptoid polymer or salt thereof of embodiment 52, wherein the peptoid polymer comprises Compound 62.

54. The peptoid polymer or salt thereof of embodiment 40 or 41, wherein the side chain comprises an oligo(ethylene glycol) moiety.

55. The peptoid polymer or salt thereof of embodiment 54, wherein the oligo(ethylene glycol) moiety is a 2-(2-(2-methoxyethoxy)ethoxy)ethyl moiety.

56. The peptoid polymer or salt thereof of embodiment 55, wherein the peptoid polymer comprises

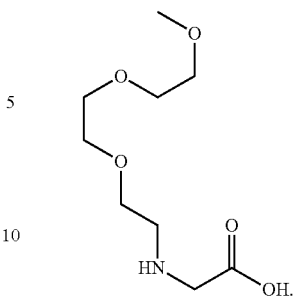

57. The peptoid polymer or salt thereof of embodiment 56, wherein the peptoid polymer comprises Compound 67.

58. The peptoid polymer or salt thereof of any one of embodiments 40 to 57, further comprising substituents X and Y located at the N-terminal and C-terminal ends of the peptoid polymer, respectively, wherein:

X and Y are independently selected from the group consisting of H, optionally substituted $C_{1-8}$ alkyl, optionally substituted $C_{1-8}$ acyl, optionally substituted $C_{1-8}$ alkylamino, —OH, —SH, —NH$_2$, carboxy, optionally substituted $C_{1-8}$ hydroxyalkyl, optionally substituted $C_{1-8}$ alkylamino, optionally substituted $C_{2-8}$ alkylthio, optionally substituted $C_{1-8}$ carboxyalkyl, and halogen, or alternatively X and Y are taken together to form a covalent bond.

59. The peptoid polymer or salt thereof of any one of embodiments 1 to 58, wherein about 10 percent of the peptoid monomers are hydrophobic.

60. The peptoid polymer or salt thereof of any one of embodiments 1 to 58, wherein about 20 percent of the peptoid monomers are hydrophobic.

61. The peptoid polymer or salt thereof of any one of embodiments 1 to 58, wherein about 30 percent of the peptoid monomers are hydrophobic.

62. The peptoid polymer or salt thereof of any one of embodiments 1 to 58, wherein about 40 percent of the peptoid monomers are hydrophobic.

63. The peptoid polymer or salt thereof of any one of embodiments 1 to 58, wherein about 50 percent of the peptoid monomers are hydrophobic.

64. The peptoid polymer or salt thereof of any one of embodiments 1 to 58, wherein about 60 percent of the peptoid monomers are hydrophobic.

65. The peptoid polymer or salt thereof of any one of embodiments 1 to 58, wherein about 70 percent of the peptoid monomers are hydrophobic.

66. The peptoid polymer or salt thereof of any one of embodiments 1 to 58, wherein about 80 percent of the peptoid monomers are hydrophobic.

67. The peptoid polymer or salt thereof of any one of embodiments 1 to 58, wherein about 90 percent of the peptoid monomers are hydrophobic.

68. The peptoid polymer or salt thereof of any one of embodiments 1 to 67, wherein the peptoid polymer forms a helical structure.

69. The peptoid polymer or salt thereof of any one of embodiments 1 to 68, wherein the peptoid polymer reduces or inhibits ice crystal formation at a temperature within about 0° C. to about −20° C.

70. The peptoid polymer or salt thereof of any one of embodiments 1 to 68, wherein the peptoid polymer reduces or inhibits ice crystal formation at a temperature within about −20° C. to about −40° C.

71. The peptoid polymer or salt thereof of any one of embodiments 1 to 68, wherein the peptoid polymer reduces or inhibits ice crystal formation at a temperature of about −20° C.

72. The peptoid polymer or salt thereof of any one of embodiments 1 to 68, wherein the peptoid polymer reduces or inhibits ice crystal formation at a temperature within about −40° C. to about −200° C.

73. The peptoid polymer or salt thereof of any one of embodiments 1 to 72, wherein the peptoid polymer salt is selected from the group consisting of a hydrochloride salt, acetate salt, sulfate salt, phosphate salt, maleate salt, citrate salt, mesylate salt, nitrate salt, tartrate salt, gluconate salt, and a combination thereof.

74. The peptoid polymer or salt thereof of any one of embodiments 1 to 73, wherein the peptoid polymer is not a peptoid polymer set forth in Tables 2-9.

75. A peptoid-peptide hybrid or salt thereof comprising a peptoid polymer or salt thereof of any one of embodiments 1 to 74 and one or more amino acids, wherein the one or more amino acids are located at one or both ends of the peptoid polymer and/or between one or more subunits.

76. The peptoid-peptide hybrid or salt thereof of embodiment 75, wherein the peptoid-peptide hybrid is not the peptoid-peptide hybrid set forth in SEQ ID NO:3, 4, 5, or 6.

77. The peptoid-peptide hybrid or salt thereof of embodiment 75 or 76, wherein the one or more amino acids are selected from the group consisting of alanine, cysteine, aspartic acid, glutamic acid, phenylalanine, glycine, histidine, isoleucine, arginine, lysine, leucine, methionine, asparagine, proline, glutamine, serine, threonine, valine, tryptophan, tyrosine, and a combination thereof.

78. The peptoid-peptide hybrid or salt thereof of embodiment 77, wherein the one or more amino acids are selected from the group consisting of isoleucine, leucine, serine, threonine, alanine, valine, arginine, and a combination thereof.

79. The peptoid-peptide hybrid or salt thereof of any one of embodiments 75 to 78, wherein the peptoid-peptide hybrid salt is selected from the group consisting of a hydrochloride salt, acetate salt, sulfate salt, phosphate salt, maleate salt, citrate salt, mesylate salt, nitrate salt, tartrate salt, gluconate salt, and a combination thereof.

80. A cryoprotectant solution comprising a peptoid polymer or salt thereof of any one of embodiments 1 to 74, a peptoid-peptide hybrid or salt thereof of any one of embodiments 75 to 79, or a combination thereof.

81. The cryoprotectant solution of embodiment 80, further comprising a compound selected from the group consisting of an ionic species, a penetrating cryoprotectant, a non-penetrating cryoprotectant, an antioxidant, a cell membrane stabilizing compound, an aquaporin or other channel forming compound, an alcohol, a sugar, a sugar derivative, a nonionic surfactant, a protein, dimethyl sulfoxide (DMSO), polyethylene glycol (PEG), polypropylene glycol (PPG), Ficoll©, polyvinylpyrrolidone, polyvinyl alcohol, hyaluronan, formamide, a natural or synthetic hydrogel, and a combination thereof.

82. The cryoprotectant solution of embodiment 81, wherein the alcohol is selected from the group consisting of propylene glycol, ethylene glycol, glycerol, methanol, butylene glycol, adonitol, ethanol, trimethylene glycol, diethylene glycol, polyethylene oxide, erythritol, sorbitol, xythyritol, polypropylene glycol, 2-methyl-2,4-pentanediol (MPD), mannitol, inositol, dithioritol, 1,2-propanediol, and a combination thereof.

83. The cryoprotectant solution of embodiment 81, wherein the sugar is a monosaccharide.

84. The cryoprotectant solution of embodiment 83, wherein the monosaccharide is selected from the group consisting of glucose, 3-O-methyl-D-glucopyranose, galactose, arabinose, fructose, xylose, mannose, and a combination thereof.

85. The cryoprotectant solution of embodiment 81, wherein the sugar is a disaccharide.

86. The cryoprotectant solution of embodiment 85, wherein the disaccharide is selected from the group consisting of sucrose, trehalose, lactose, maltose, and a combination thereof.

87. The cryoprotectant solution of embodiment 81, wherein the sugar is a polysaccharide.

88. The cryoprotectant solution of embodiment 87, wherein the polysaccharide is selected from the group consisting of raffinose, dextran, and a combination thereof.

89. The cryoprotectant solution of embodiment 81, wherein the PEG or PPG has an average molecular weight less than about 3,000 g/mol.

90. The cryoprotectant solution of embodiment 81, wherein the PEG or PPG has an average molecular weight between about 200 g/mol and 400 g/mol.

91. The cryoprotectant solution of embodiment 81, wherein the protein is selected from the group consisting of egg albumin, bovine serum albumin, human serum albumin, gelatin, and a combination thereof.

92. The cryoprotectant solution of embodiment 81, wherein the natural or synthetic hydrogel comprises chitosan, hyaluronic acid, or a combination thereof.

93. The cryoprotectant solution of embodiment 81, wherein the nonionic surfactant is selected from the group consisting of polyoxyethylene lauryl ether, polysorbate 80, and a combination thereof.

94. A method of preserving a tissue, an organ, or a cell, the method comprising contacting the tissue, organ, or cell with a peptoid polymer or salt thereof of any one of embodiments 1 to 74, a peptoid-peptide hybrid or salt thereof of any one of embodiments 75 to 79, a cryoprotectant solution of any one of embodiments 80 to 93, or a combination thereof.

95. The method of embodiment 94, wherein the peptoid polymer or salt thereof, peptoid-peptide hybrid or salt thereof, cryoprotectant solution, or combination thereof is present in an amount sufficient to reduce or inhibit ice crystal formation at a temperature within about 0° C. to about −20° C.

96. The method of embodiment 94, wherein the peptoid polymer or salt thereof, peptoid-peptide hybrid or salt thereof, cryoprotectant solution, or combination thereof is present in an amount sufficient to reduce or inhibit ice crystal formation at a temperature within about −20° C. to about −40° C.

97. The method of embodiment 94, wherein the peptoid polymer or salt thereof, peptoid-peptide hybrid or salt thereof, cryoprotectant solution, or combination thereof is present in an amount sufficient to reduce or inhibit ice crystal formation at a temperature of about −20° C.

98. The method of embodiment 94, wherein the peptoid polymer or salt thereof, peptoid-peptide hybrid or salt thereof, cryoprotectant solution, or combination thereof is present in an amount sufficient to reduce or inhibit ice crystal formation at a temperature within about −40° C. to about −200° C.

99. The method of any one of embodiments 94 to 98, wherein the tissue is a bioengineered tissue.

100. The method of any one of embodiments 94 to 99, wherein the peptoid polymer or salt thereof, the peptoid-peptide hybrid or salt thereof, or a combination thereof is present in amount between about 100 nM and about 1,000 mM.

101. The method of any one of embodiments 94 to 100, wherein the tissue, organ, or cell is selected from the group consisting of heart, liver, lung, kidney, pancreas, intestine, thymus, cornea, nerve cells, blood platelets, sperm cells, oocytes, genitourinary cells, embryonic cells, stem cells, human pluripotent stem cells, hematopoietic stem cells, lymphocytes, granulocytes, immune system cells, bone cells, primary cells, organoids, and a combination thereof.

102. A method for preserving a biological macromolecule, the method comprising contacting the biological macromolecule with a peptoid polymer or salt thereof of any one of embodiments 1 to 74, a peptoid-peptide hybrid or salt thereof of any one of embodiments 75 to 79, a cryoprotectant solution of any one of embodiments 80 to 93, or a combination thereof.

103. The method of embodiment 102, wherein the biological macromolecule is selected from the group consisting of a nucleic acid, an amino acid, a protein, an isolated protein, a peptide, a lipid, a composite structure, and a combination thereof.

104. A cosmetic care product comprising a peptoid polymer or salt thereof of any one of embodiments 1 to 74, a peptoid-peptide hybrid or salt thereof of any one of embodiments 75 to 79, a cryoprotectant solution of any one of embodiments 80 to 93, or a combination thereof.

105. An antifreeze product comprising a peptoid polymer or salt thereof of any one of embodiments 1 to 74, a peptoid-peptide hybrid or salt thereof of any one of embodiments 75 to 79, a cryoprotectant solution of any one of embodiments 80 to 93, or a combination thereof.

106. The antifreeze product of embodiment 105, wherein the antifreeze product is a deicing or ice-inhibiting product used to prevent, inhibit, or delay the formation of ice on or within an object.

107. The antifreeze product of embodiment 106, wherein the object is selected from the group consisting of an aircraft or a part thereof, a gas pipeline, a window, electrical equipment, a drone, a cable, a power line, mechanical equipment, a car engine, a gear system, and a brake system.

108. A frozen food product comprising a peptoid polymer or salt thereof of any one of embodiments 1 to 74, a peptoid-peptide hybrid or salt thereof of any one of embodiments 75 to 79, a cryoprotectant solution of any one of embodiments 80 to 93, or a combination thereof.

109. The frozen food product of embodiment 108, wherein the frozen food product is selected from the group consisting of ice cream, yogurt, seafood, fruit, and meat products.

It is understood that the examples and embodiments described herein are for illustrative purposes only and that various modifications or changes in light thereof will be suggested to persons skilled in the art and are to be included within the spirit and purview of this application and scope of the appended claims. All publications, patents, patent applications, and sequence accession numbers cited herein are hereby incorporated by reference in their entirety for all purposes.

| Informal Sequence Listing | |
|---|---|
| Sequence | Notes |
| Nep-Nep-Xaa-Xaa-Xaa-Xaa-Nep-Nep-Nep-Nep-Nme-Nme | Peptoid-Peptide Hybrid |
| Nme-Nme-Xaa-Nme-Nme-Nme-Nme-Nhp-Nhp-Nsb-Xaa-Nme-Nme-Xaa-Nme-Nme-Nme | Peptoid-Peptide Hybrid |
| Nme-Nme-Xaa-Nme-Nme-Nme-Nme-Nme-Nme-Nme-Xaa-Xaa | Peptoid-Peptide Hybrid |
| Arg-Nsb-Nsb-Nhp-Nhp-Nsb-Nsb-Nhp-Nhp-Nsb-Nsb | Peptoid-Peptide Hybrid (Compound 58) |
| Nsb-Nhp-Nhp-Nhp-Nsb-Nhp-Nhp-Nhp-Nsb-Nhp | Compound 6 |
| Nsb-Nsb-Nhp-Nhp-Nsb-Nsb-Nhp-Nhp-Nsb-Nsb | Compound 12 |
| Nsb-Nhp-Nhp-Nhp-Nhp-Nhp-Nsb-Nhp-Nhp-Nhp | Compound 8 |
| Nsb-Nsb-Nsb-Nhp-Nhp-Nhp-Nhp-Nsb-Nsb-Nhp | Compound 2 |
| Nib-Nib-Nhp-Nhp-Nib-Nib-Nhp-Nhp-Nib-Nib | Compound 25 |
| Nbu-Nbu-Nhp-Nhp-Nbu-Nbu-Nhp-Nhp-Nbu-Nbu | Compound 26 |
| Npr-Npr-Nhp-Nhp-Npr-Npr-Nhp-Nhp-Npr-Npr | Compound 27 |
| Nip-Nip-Nhp-Nhp-Nip-Nip-Nhp-Nhp-Nip-Nip | Compound 28 |
| Nmb-Nmb-Nhp-Nhp-Nmb-Nmb-Nhp-Nhp-Nmb-Nmb | Compound 59 |
| Ac-Nsb-Nsb-Nhp-Nhp-Nsb-Nsb-Nhp-Nhp-Nsb-Nsb | Compound 60 (Compound 12 with acetylated N-terminus) |
| Nsb-Nsb-Nhp-Nhp-Nsb-Nsb-Nhp-Nhp-Nsb-Nsb-COOH | Compound 61 (Compound 12 with carboxy C-terminus) |

-continued

| Informal Sequence Listing | |
|---|---|
| Sequence | Notes |
| Nsb-Nsb-Nmo-Nmo-Nsb-Nsb-Nmo-Nmo-Nsb-Nsb | Compound 62 |
| Nsb-Nsb-Ntf-Ntf-Nsb-Nsb-Ntf-Ntf-Nsb-Nsb | Compound 63 |
| Nme-Nme-Nhp-Nhp-Nme-Nme-Nhp-Nhp-Nme-Nme | Compound 64 |
| Nbr-Nbr-Nhe-Nhe-Nbr-Nbr-Nhe-Nhe-Nbr-Nbr | Compound 65 |
| Npr-Npr-Nrh-Nrh-Npr-Npr-Nrh-Nrh-Npr-Npr | Compound 66 |
| Nsb-Nsb-N3p-N3p-Nsb-Nsb-N3p-N3p-Nsb-Nsb | Compound 67 |
| Nsb-Nsb-Ndh-Ndh-Nsb-Nsb-Ndh-Ndh-Nsb-Nsb | Compound 68 |
| Nsb-Nsb-Nhp-Nhp-Nsb-Nsb-Nhp-Nsb-Nsb | Compound 69 |
| Nsb-Nsb-Nhp-Nhp-Nsb-Nsb-Nsb-Nhp-Nsb-Nsb | Compound 70 |
| Nsb-Nsb-Nhp-Nsb-Nsb-Nsb-Nhp-Nhp-Nsb-Nsb | Compound 71 |
| Nsb-Nsb-Nsb-Nhp-Nsb-Nsb-Nhp-Nhp-Nsb-Nsb | Compound 72 |
| Nsb-Nsb-Nff-Nff-Nsb-Nsb-Nff-Nff-Nsb-Nsb | Compound 73 |
| Nsb-Nsb-Nhe-Nhe-Nsb-Nsb-Nhe-Nhe-Nsb-Nsb | Compound 74 |
| Nsb-Nsb-Nyp-Nyp-Nsb-Nsb-Nyp-Nyp-Nsb-Nsb | Compound 75 |
| Nsb-Nsb-Nop-Nop-Nsb-Nsb-Nop-Nop-Nsb-Nsb | Compound 76 |
| Nbr-Nbr-Nrh-Nrh-Nbr-Nbr-Nrh-Nrh-Nbr-Nbr | Compound 77 |
| Nbr-Nbr-Nsh-Nsh-Nbr-Nbr-Nsh-Nsh-Nbr-Nbr | Compound 78 |
| Nsb-Nsb-Ndp-Ndp-Nsb-Nsb-Ndp-Ndp-Nsb-Nsb | Compound 79 |
| Nrh-Nrh-Nrh-Nrh-Nrh-Nrh-Nrh-Nrh-Nrh-Nrh | Compound 80 |
| Nsb-Nsb-Nhp-Nhp-Nsb-Nsb | Compound 81 |
| Nhp-Nhp-Nsb-Nsb-Nhp-Nhp-Nsb-Nsb | Compound 82 |
| Nsb-Nsb-Nhp-Nhp-Nsb-Nsb-Nhp-Nhp-Nsb-Nsb-Nhp-Nhp-Nsb-Nsb | Compound 83 |
| Nsb-Nsb-Nhp-Nhp-Nsb-Nsb-Nhp-Nhp-Nsb-Nsb-Nhp-Nhp-Nsb-Nsb-Nhp-Nhp-Nsb-Nsb | Compound 84 |
| Nsb-Nsb-Nhp-Nhp-Nsb-Nsb-Nhp-Nhp-Nsb-Nsb-Nhp-Nhp-Nsb-Nsb-Nhp-Nhp-Nsb-Nsb-Nhp-Nhp-Nsb-Nsb | Compound 85 |
| Nbr-Nbr-Nop-Nop-Nbr-Nbr-Nop-Nop-Nbr-Nbr | Compound 86 |
| Nbs-Nbs-Nop-Nop-Nbs-Nbs-Nop-Nop-Nbs-Nbs | Compound 87 |
| Nbs-Nbs-Nrh-Nrh-Nbs-Nbs-Nrh-Nrh-Nbs-Nbs | Compound 88 |
| Nbs-Nbs-Nsh-Nsh-Nbs-Nbs-Nsh-Nsh-Nbs-Nbs | Compound 89 |
| Nbr-Nbs-Nrh-Nrh-Nbr-Nbs-Nrh-Nrh-Nbr-Nbs | Compound 90 |
| Nbs-Nbr-Nrh-Nrh-Nbs-Nbr-Nrh-Nrh-Nbs-Nbr | Compound 91 |
| Nbr-Nbs-Nsh-Nsh-Nbr-Nbs-Nsh-Nsh-Nbr-Nbs | Compound 92 |
| Nbs-Nbr-Nsh-Nsh-Nbs-Nbr-Nsh-Nsh-Nbs-Nbr | Compound 93 |
| Nbr-Nbr-Nrh-Nsh-Nbr-Nbr-Nrh-Nsh-Nbr-Nbr | Compound 94 |
| Nbr-Nbr-Nsh-Nrh-Nbr-Nbr-Nsh-Nrh-Nbr-Nbr | Compound 95 |
| Nbs-Nbs-Nrh-Nsh-Nbs-Nbs-Nrh-Nsh-Nbs-Nbs | Compound 96 |
| Nbs-Nbs-Nsh-Nrh-Nbs-Nbs-Nsh-Nrh-Nbs-Nbs | Compound 97 |
| Nbr-Nbs-Nrh-Nsh-Nbr-Nbs-Nrh-Nsh-Nbr-Nbs | Compound 98 |

| Informal Sequence Listing | |
|---|---|
| Sequence | Notes |
| Nbr-Nbs-Nsh-Nrh-Nbr-Nbs-Nsh-Nrh-Nbr-Nbs | Compound 99 |
| Nbs-Nbr-Nrh-Nsh-Nbs-Nbr-Nrh-Nsh-Nbs-Nbr | Compound 100 |
| Nbs-Nbr-Nsh-Nrh-Nbs-Nbr-Nsh-Nrh-Nbs-Nbr | Compound 101 |

What is claimed is:

1. A peptoid polymer or salt thereof having the sequence $[H_2P_2]_n$, $[P_2H_2]_n$, X-$[H_2P_2]_n$-Y, X-$[P_2H_2]_n$-Y, $[H_2P_2]_nH_2$, $[P_2H_2]_nH_2$, $[H_2P_2]_nP_2$, or $[P_2H_2]_nP_2$, wherein the subscript n is between 2 and 5;

wherein H is a hydrophobic peptoid monomer selected from the group consisting of

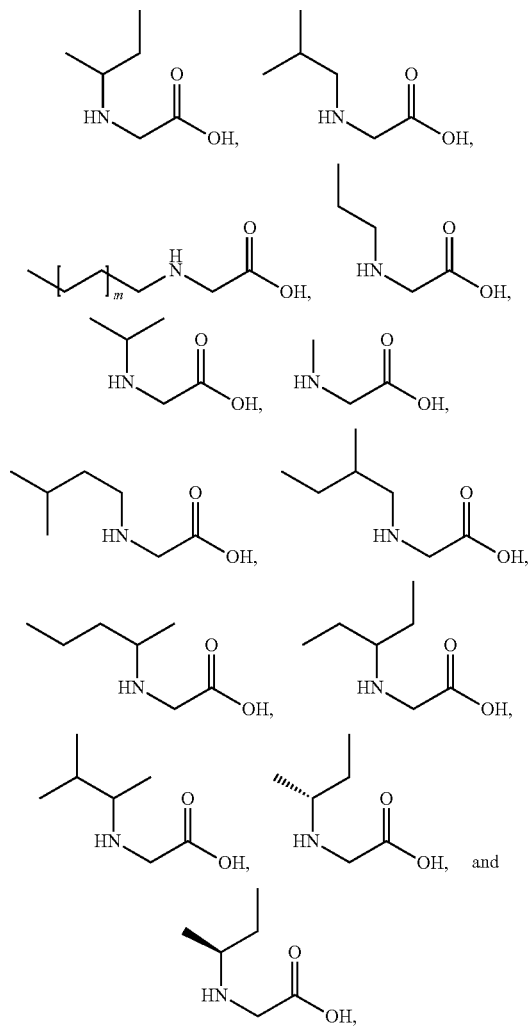

wherein the subscript m is the number of repeat units and is between 1 and 10, wherein P is a polar peptoid monomer selected from the group consisting of

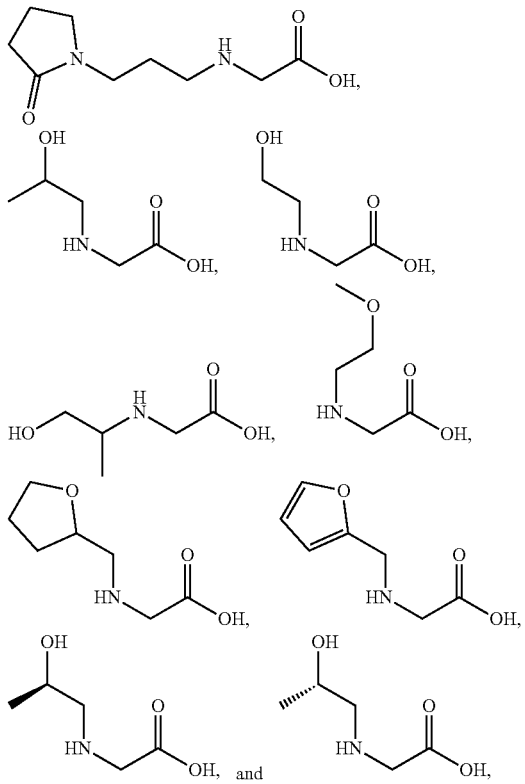

and wherein X and Y are independently selected from the group consisting of H, optionally substituted $C_{1-8}$ alkyl, optionally substituted $C_{1-8}$ acyl, optionally substituted $C_{1-8}$ alkylamino, -OH, -SH, -NH$_2$, secondary amine, tertiary amine, carboxy, optionally substituted $C_{1-8}$ hydroxyalkyl, optionally substituted $C_{1-8}$ alkylamino, optionally substituted $C_{2-8}$ alkylthio, optionally substituted $C_{1-8}$ carboxyalkyl, and halogen.

2. The peptoid polymer or salt thereof of claim 1, wherein the peptoid polymer forms a helical structure.

3. The peptoid polymer or salt thereof of claim 1, wherein the peptoid polymer salt is selected from the group consisting of a hydrochloride salt, acetate salt, sulfate salt, phosphate salt, maleate salt, citrate salt, mesylate salt, nitrate salt, tartrate salt, gluconate salt, and a combination thereof.

4. A peptoid-peptide hybrid or salt thereof comprising a peptoid polymer or salt thereof of claim 1 and one or more amino acids, wherein the one or more amino acids are located at one or both ends of the peptoid polymer.

5. The peptoid-peptide hybrid or salt thereof of claim 4, wherein the one or more amino acids are selected from the group consisting of alanine, cysteine, aspartic acid, glutamic acid, phenylalanine, glycine, histidine, isoleucine, arginine, lysine, leucine, methionine, asparagine, proline, glutamine, serine, threonine, valine, tryptophan, tyrosine, and a combination thereof.

6. The peptoid-peptide hybrid or salt thereof of claim 4, wherein the peptoid-peptide hybrid salt is selected from the group consisting of a hydrochloride salt, acetate salt, sulfate salt, phosphate salt, maleate salt, citrate salt, mesylate salt, nitrate salt, tartrate salt, gluconate salt, and a combination thereof.

7. A cryopreservation solution comprising a peptoid polymer or salt thereof of claim 1.

8. A cosmetic care product comprising a peptoid polymer or salt thereof of claim 1.

9. An antifreeze product comprising a peptoid polymer or salt thereof of claim 1.

10. The antifreeze product of claim 9, wherein the antifreeze product is a deicing or ice-inhibiting product used to prevent, inhibit, or delay the formation of ice on or within an object.

11. The antifreeze product of claim 10, wherein the object is selected from the group consisting of an aircraft or a part thereof, a gas pipeline, a window, electrical equipment, a drone, a cable, a power line, mechanical equipment, a car engine, a gear system, and a brake system.

12. A frozen food product comprising a peptoid polymer or salt thereof of claim 1.

13. The frozen food product of claim 12, wherein the frozen food product is selected from the group consisting of ice cream, yogurt, seafood, fruit, and meat products.

* * * * *